United States Patent
Chen et al.

(10) Patent No.: US 12,325,758 B2
(45) Date of Patent: *Jun. 10, 2025

(54) PROTEASE CLEAVABLE BISPECIFIC ANTIBODIES AND USES THEREOF

(71) Applicant: Zhejiang Shimai Pharmaceutical Co. Ltd., Hangzhou (CN)

(72) Inventors: Weizao Chen, Frederick, MD (US); Yanping Wang, Frederick, MD (US); Zuoxiang Xiao, Frederick, MD (US)

(73) Assignee: Zhejiang Shimai Pharmaceutical Co., Ltd., Hangzhou (CN)

( * ) Notice: Subject to any disclaimer, the term of this patent is extended or adjusted under 35 U.S.C. 154(b) by 804 days.

This patent is subject to a terminal disclaimer.

(21) Appl. No.: 17/458,945

(22) Filed: Aug. 27, 2021

(65) Prior Publication Data

US 2021/0388118 A1    Dec. 16, 2021

Related U.S. Application Data

(63) Continuation of application No. 17/312,258, filed as application No. PCT/US2019/068063 on Dec. 20, 2019.

(60) Provisional application No. 62/815,132, filed on Mar. 7, 2019, provisional application No. 62/783,411, filed on Dec. 21, 2018.

(51) Int. Cl.
    *C07K 16/46*     (2006.01)
    *A61K 39/00*     (2006.01)
    *A61P 35/00*     (2006.01)
    *C07K 14/71*     (2006.01)
    *C07K 14/82*     (2006.01)
    *C07K 16/28*     (2006.01)

(52) U.S. Cl.
    CPC ............ *C07K 16/468* (2013.01); *A61P 35/00* (2018.01); *C07K 14/71* (2013.01); *C07K 14/82* (2013.01); *C07K 16/2809* (2013.01); *C07K 16/2863* (2013.01); *A61K 2039/505* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/565* (2013.01); *C07K 2317/73* (2013.01); *C07K 2317/92* (2013.01); *C07K 2319/03* (2013.01); *C07K 2319/30* (2013.01); *C07K 2319/50* (2013.01)

(58) Field of Classification Search
    None
    See application file for complete search history.

(56) References Cited

U.S. PATENT DOCUMENTS

| | | | |
|---|---|---|---|
| 2010/0008929 | A1 | 1/2010 | Van de Winkel et al. |
| 2012/0237507 | A1 | 9/2012 | Bossenmaier et al. |
| 2013/0266568 | A1 | 10/2013 | Brinkmann et al. |
| 2013/0315911 | A1 | 11/2013 | Stevens et al. |
| 2017/0218091 | A1 | 8/2017 | Ambrosi |
| 2017/0247476 | A1 | 8/2017 | Yan et al. |
| 2018/0125972 | A1 | 5/2018 | Igawa et al. |
| 2021/0388118 | A1 | 12/2021 | Chen et al. |
| 2023/0357410 | A1* | 11/2023 | Chen .................. C07K 16/468 |

FOREIGN PATENT DOCUMENTS

| | | | |
|---|---|---|---|
| WO | WO 2005/090407 A1 | 9/2005 | |
| WO | WO 2017/162587 A1 | 9/2017 | |
| WO | WO 2018/144784 A1 | 8/2018 | |
| WO | WO 2019/023097 A1 | 1/2019 | |

OTHER PUBLICATIONS

Rudikoff et al., Proc Natl Acad Sci USA 79: 1979 (Year: 1982).*
Barrios et al., J Molecular Recognition 17: 332-338 (Year: 2004).*
Piatesi et al., ChemBio Chem 5: 460-466 (Year: 2004).*
MacCallum et al., Mol. Biol 262: 732-745 (Year: 1996).*
Pascalis et al., Journal of Immunology 169: 3076-3084 (Year: 2002).*
Wu et al., J. Mol. Biol. 294: 151-162 (Year: 1999).*
Brinkmann et al., The making of bispecific antibodies. MAbs. Feb./Mar. 2017;9(2):182-212. doi: 10.1080/19420862.2016. 1268307.
Harwood et al., ATTACK, a novel bispecific T cell-recruiting antibody with trivalent EGFR binding and monovalent CD3 binding for cancer immunotherapy. Oncoimmunology. Sep. 27, 2017;7(1):e1377874. doi: 10.1080/2162402X.2017.1377874. eCollection 2017.
Knuth et al., Induction of tumour cell lysis by a bispecific antibody recognising epidermal growth factor receptor (EGFR) and CD3. Eur J Cancer. 1994;30A(8):1103-7. doi: 10.1016/0959-8049(94)90466-9.

(Continued)

*Primary Examiner* — Phuong Huynh
(74) *Attorney, Agent, or Firm* — Wolf, Greenfield & Sacks, P.C.

(57) ABSTRACT

The present invention provides recombinant bispecific antibodies designed to bind to a surface antigen on target cells and to an activating component on immune cells such as T cells. The bispecific antibodies comprise two polypeptide chains that contain Fv and Fab as antigen-binding fragments and a modified Fc region to facilitate heterodimer formation. In one embodiment, the bispecific antibodies further comprise protease cleavage sites and/or motifs that would cause steric occlusion of the antigen binding sites so that the antibodies would be activated only in a specific environment, e.g. in the vicinity of a tumor. In another embodiment, the bispecific antibodies comprise modified sequences that confer reduced binding affinity to CDS and/or cross-reactive binding to CDS on cells from different species.

15 Claims, 52 Drawing Sheets

Specification includes a Sequence Listing.

(56) References Cited

OTHER PUBLICATIONS

Laporte et al., CD3-EGFR Probody(TM) T Cell-engaging Bispecific Therapeutic Induces Tumor Regressions and Substantially Increases Safety Window in Preclinical Studies. Cytomx Therapeutics, Inc. Jan. 1, 2015. 1 page.
Ma et al., Anti-CD3 x EGFR bispecific antibody redirects cytokine-induced killer cells to glioblastoma in vitro and in vivo. Oncol Rep. Nov. 2015;34(5):2567-75. doi: 10.3892/or.2015.4233. Epub Aug. 28, 2015.
Metz et al., Bispecific antibody derivatives with restricted binding functionalities that are activated by proteolytic processing. Protein Eng Des Sel. Oct. 2012;25(10):571-80. doi: 10.1093/protein/gzs064. Epub Sep. 13, 2012.
Reusch et al., Anti-CD3 x anti-epidermal growth factor receptor (EGFR) bispecific antibody redirects T-cell cytolytic activity to EGFR-positive cancers in vitro and in an animal model. Clin Cancer Res. Jan. 1, 2006;12(1):183-90. doi: 10.1158/1078-0432.CCR-05-1855.
Extended European Search Report for Application No. 21179046.4, mailed Jan. 12, 2022.
Moradi-Kalbolandi et al., Monoclonal antibody-based therapeutics, targeting the epidermal growth factor receptor family: from herceptin to Pan HER. J Pharm Pharmacol. Jul. 2018;70(7):841-854. doi: 10.1111/jphp.12911. Epub Mar. 25, 2018.
International Search Report and Written Opinion for Application No. PCT/US2019/068063, mailed May 13, 2020.
International Preliminary Report on Patentability for Application No. PCT/US2019/068063, mailed Jul. 1, 2021.
U.S. Appl. No. 17/312,258, filed Jun. 9, 2021, Chen et al.
PCT/US2019/068063, May 13, 2020, International Search Report and Written Opinion.
PCT/US2019/068063, Jul. 1, 2021, International Preliminary Report on Patentability.
Edwards et al., The remarkable flexibility of the human antibody repertoire; isolation of over one thousand different antibodies to a single protein, BlyS. J Mol Biol. Nov. 14, 2003;334(1):103-18. doi: 10.1016/j.jmb.2003.09.054.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

\* cited by examiner

Figure 41 hSP34 HCDR3

| Germline | V region | N1 | D region | P | N2 | J region |
|---|---|---|---|---|---|---|
| | tgtgtga....gacacggaaacttc....gggaactcctac | | gt | gtcttacttcgca....tactgg | | |
| IGHV3-23*04 | tgtgcga | | | | | |
| IGHD1-26*01 | | | gggagctactac | | | |
| IGHJ4*03 | | | | | | tactgg |

| | IMGT numbering |
|---|---|
| hSP34 HCDR3 | C V R H G N F G N S Y Y V S Y F A Y W |
| Germline | C A R H G N F G S Y Y V S Y F A Y W |

PROTEASE CLEAVABLE BISPECIFIC ANTIBODIES AND USES THEREOF

CROSS REFERENCE TO RELATED APPLICATIONS

This application is a Continuation application of application Ser. No. 17/312,258, filed Jun. 9, 2021, which is a national stage filing under 35 U.S.C. § 371 of International PCT Application PCT/US2019/068063, filed on Dec. 20, 2019, which claims priority to U.S. Provisional Patent Application No. 62/783,411, filed on Dec. 21, 2018, and U.S. Provisional Patent Application No. 62/815,132, filed on Mar. 7, 2019, the contents of which are incorporated herein by reference.

BACKGROUND OF THE INVENTION

Antibodies are gammaglobulin proteins, predominantly referred to as immunoglobulins (Ig). A monomeric antibody is composed of two heavy chains and two light chains. The amino terminal ends of the polypeptide chains show considerable variation in amino acid composition and are referred to as the variable (V) domains/regions to distinguish them from the relatively constant (C) domains/regions. Each light chain has a variable domain and a constant domain. Each heavy chain has four domains: a variable domain, and constant domains 1, 2, and 3. The antigen binding site is located in the Fab (Fragment antigen binding) region which includes a light chain variable domain (VL), a heavy chain variable domain (VH), a light chain constant domain (CL) and a heavy chain constant domain 1 (CH1). The combination of a light chain variable domain (VL) and a heavy chain variable domain (VH) is called a Fv (Fragment variable) region. The Fc (Fragment, Crystallizable) region of an antibody includes heavy chain constant domains 2 and 3 (CH2 and CH3).

Each variable domain contains three hypervariable loops, known as complementarity determining regions (CDRs), evenly distributed between four less variable framework (FR) regions. It is the CDRs that provide a specific antigen recognition site on the surface of the antibody and the hypervariability of these regions enables antibodies to recognize an almost unlimited number of antigens. The heavy and light chains are held together by a combination of non-covalent interactions and covalent interchain disulfide bonds, forming a bilaterally symmetric structure. The hinge region is the area of the heavy chains between the first and second constant domains (CH1 and CH2) and is held together by disulfide bonds. This flexible hinge region allows the distance between the two antigen-binding sites to vary.

Selective destruction of an individual target cell or a specific target cell type is often desirable in a variety of clinical settings such as cancer therapy. One way of achieving this is by inducing an immune response against the tumor, for example, by making immune effector cells such as natural killer (NK) cells or cytotoxic T lymphocytes (CTLs) attack and destroy tumor cells. In this regard, bispecific antibodies designed to bind to a surface antigen on target cells and to an activating, invariant component of the T cell receptor (TCR) complex have become of interest in recent years. Simultaneous binding of such an antibody to both of its targets will force a temporary interaction between target cells and T cells, causing activation of cytotoxic T cells and subsequent lysis of the target cells. Hence, the immune response is re-directed to the target cells and is independent of peptide antigen presentation by the target cell or the specificity of the T cell as in normal MHC-restricted activation of CTLs.

With the recent advance of genetic and protein engineering technologies, bispecific antibodies (BsAb) such as BiTE has emerged to show promising applications. BiTE (Bispecific T cell engager) is a type of fusion proteins with two single-chain antibody variable fragments (scFvs), one of which targets CD3 and the other targets a tumor antigen, joined by a (G4S)3 polypeptide linker. In the absence of Fc, these antibodies cannot be purified with protein A and G, and have short in vivo half-lives. Consequently, continuous infusion is required in clinical use. Also, bispecific antibodies in single-chain format (scFvs) and variants thereof have the problem of becoming aggregated easily.

There are other bispecific antibody technologies. Roche CrossMab contains Fc and therefore has much longer half-life in vivo than BiTE. CrossMab uses the knob-in-hole technology for Fc heterodimerization, but it could not yield 100% heterodimeric antibodies. In CrossMab, a wild-type IgG1 Fc and hinge are used which enable CrossMab to bind to all Fc receptor (FcR)-expressing cells such as macrophages. As a consequence, T cells will not only kill cancer cells but also kill the FcR-expressing cells leading to a side effect called lymphopenia.

Bispecific antibodies from Xencor Inc. and Synimmune GMBH comprise two antigen-binding domains linked to the N terminals and C terminals of Fc polypeptides respectively. The long distance between the two binding sites at the N terminals and C terminals is less favorable for inducing an immune synapse like those formed in the course of natural cytotoxic T cell recognition.

Protease-activatable bispecific proteins developed by Amgen (U.S. patent application publication No. 2017/0247476) use two scFvs as antigen-binding fragments, CDR domain to mask CD3 binding, CH1-CL for heterodimerization, and wild-type IgG Fc or Fc with heterodimerizing alterations such as knob-in-hole mutations to extend half-lives. The use of scFvs, however, could cause aggregation and instability of the proteins. Although CH1-CL had been used as a heterodimerization scaffold to generate bispecific antibodies or multivalent fusion proteins, cooperation between the VH-VL and CH1-CL interface is required for mutual stabilization. In the absence of VH-VL, it has been reported that CH1-CL is insufficient to yield heterodimeric products. Furthermore, Fc with currently known heterodimerizing alterations has failed to form heterodimers completely.

The protease-activated T cell bispecific molecules developed by Roche (international application publication No. WO2017/162587) are based on the above-mentioned CrossMab platform and uses an idiotype-specific scFv as a masking moiety to block binding of the CD3 antibody. This design inherits the shortcomings associated with CrossMab platform and scFv fragments described above.

International Application No. PCT/US18/43232 disclosed a bispecific antibody targeting both FLT3 and CD3, wherein the bispecific antibody includes a single chain variable fragment (scFv) of an anti-CD3 antibody fused to the Fab of an anti-FLT3 antibody. However, the binding domains to CD3 and FLT3 are not masked and no protease-sensitive polypeptide linkers are incorporated.

Bispecific antibodies with improved pharmacokinetic properties would be desirable to eliminate the need for continuous dosing. However, longer half-life could cause prolonged or poorly localized T cell activation, leading to undesirable side effects. Hence, there is a need in the art for bispecific antibody formats that have reasonably long half-life, but are activated specifically in a disease microenvironment, for example, in the vicinity of a tumor.

SUMMARY OF THE INVENTION

The present invention provides recombinant bispecific antibodies designed to bind to a surface antigen on target cells and to an activating component on immune cells such as T cells. In one embodiment, the bispecific antibodies of the present invention comprise Fv and Fab as antigen-binding fragments and a modified Fc region which result in excellent properties of final products including 100% heterodimer, high yield, high stability, low aggregation propensities and extended half-lives. In another embodiment, the present bispecific antibodies may also comprise protease cleavage sites and/or motifs that would cause steric occlusion of the antigen binding site so that the antibodies would be activated only in a specific environment, e.g. in the vicinity of a tumor.

In one embodiment, the present invention provides a recombinant bispecific antibody, comprising
 (i) a first polypeptide comprising from N- to C-terminus a first light chain variable domain, a human light chain constant region (CL), a human heavy chain constant region 2 (CH2) and a human heavy chain constant region 3 (CH3);
 (ii) a second polypeptide comprising from N- to C-terminus a first heavy chain variable domain, a human heavy chain constant region 1 (CH1), a human heavy chain constant region 2 (CH2) and a human heavy chain constant region 3 (CH3); and
 (iii) a second light chain variable domain connected to the first light chain variable domain by a first linker, and a second heavy chain variable domain connected to the first heavy chain variable domain by a second linker; or
 a second light chain variable domain connected to the C-terminus of the CH3 of the first polypeptide by a first linker, and a second heavy chain variable domain connected to the C-terminus of the CH3 of the second polypeptide by a second linker,
 wherein the first light chain variable domain and the first heavy chain variable domain confer binding specificity to a first antigen, the second light chain variable domain and the second heavy chain variable domain confer binding specificity to a second antigen.

In one embodiment, the recombinant bispecific antibody of the present invention further comprises a heterodimerization motif or a long flexible motif, wherein the heterodimerization motif or long flexible motif is connected to the N terminus of the second light chain variable domain and the second heavy chain variable domain via one or more linkers.

In one embodiment, the recombinant bispecific antibody of the present invention further comprises modified sequences that confer reduced binding affinity to CD3 on T cells. In another embodiment, the recombinant bispecific antibody disclosed herein possesses cross-reactive binding to CD3, e.g. binding to human and cynomolgus CD3.

The present invention also provides polynucleotides encoding one or both polypeptides of the recombinant bispecific antibody disclosed herein. In another embodiment, the present invention also includes expression vectors comprising the above polynucleotides. In yet another embodiment, the present invention also includes host cells comprising the above expression vectors.

The present invention also provides a method of using the above polynucleotides or expression vectors to prepare the recombinant bispecific antibody disclosed herein.

BRIEF DESCRIPTION OF THE DRAWINGS

FIG. 20A shows macroscopic appearance of tumor tissues. FIG. 20B shows average tumor weight.

FIG. 28A shows intact dproBiTE, whereas FIG. 28B shows protease-cleaved dproBiTE. Molecular masses of standards are shown on the left.

FIG. 41 shows an analysis of hSP34 heavy chain CDR3 (HCDR3) sequence using IMGT/V-QUEST. The upper panel shows alignment of the nucleotide sequences of hSP34 HCDR3 V, D and J regions with the sequences of the closest germline human antibody sequences. The lower panel shows alignment of the amino acid sequence of hSP34 HCDR3 with that of the germline human antibody. Mutated nucleotide and amino acid sequences compared to the corresponding germlines sequences are underlined.

DETAILED DESCRIPTION OF THE INVENTION

Distinctive Features of the Present Invention

Figure 1A:
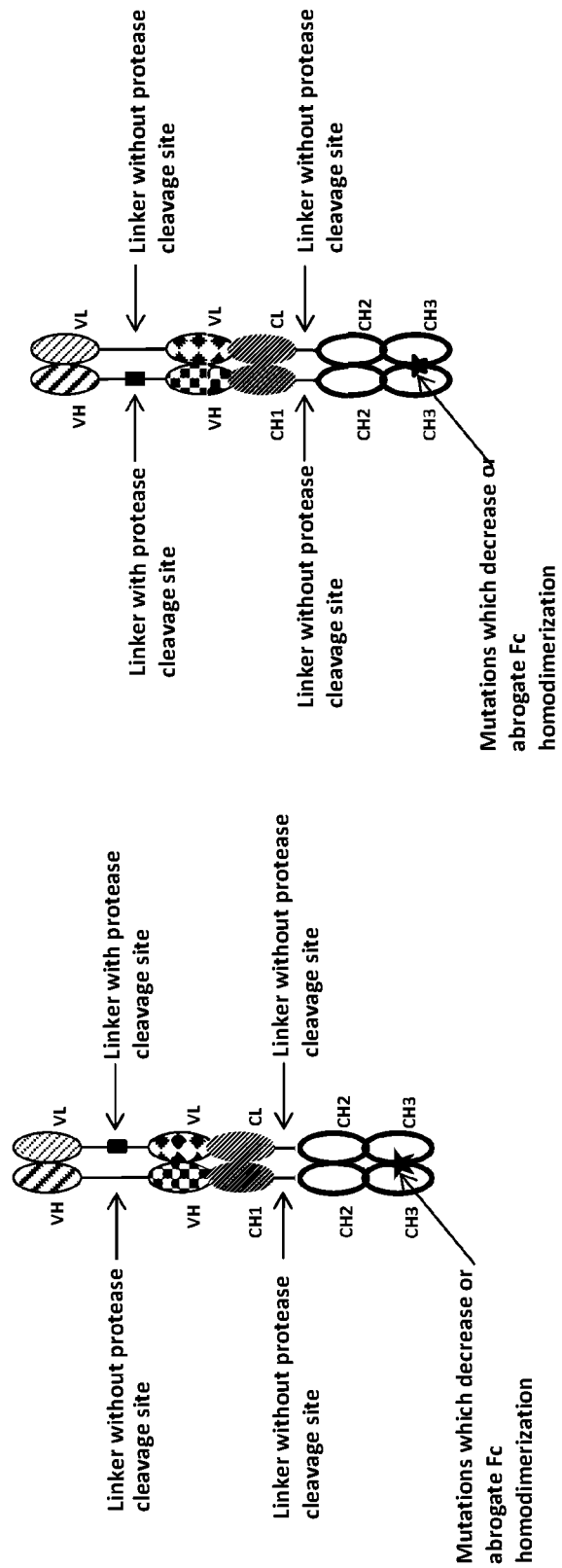
FIG. 1A shows schematic representation of examples of one embodiment of protease cleavable bispecific antibodies of the present invention.

Compared to published monovalent bispecific antibodies developed by others, the bispecific antibodies of the present invention have the following advantageous and distinctive features. Firstly, in one embodiment, the bispecific antibodies of the present invention use monomeric human IgG1 Fc (mFc) to extend in vivo half-life. In addition, the present bispecific antibodies contain only two polypeptide chains and employ both Fab and Fv for heterodimerization and antigen recognition. The present mFc exists as a monomer at low concentrations but tends to form a dimer at high concentrations. Therefore, when the heavy and light chains of the present bispecific antibodies are assembled, the mFc forms a dimer due to high local concentrations and further stabilize the bispecific antibodies in cooperation with the heterodimerization strength from Fab and Fv. A combination of the features mentioned above results in excellent properties for the bispecific antibodies such as 100% heterodimer, high yield, high stability and low aggregation propensities.

In contrast, many bispecific antibodies in the art have problems in yield and homodimerization. For example, many bispecific antibodies in the art contain three or four polypeptide chains, thereby resulting in low yield of antibodies. Moreover, a number of bispecific antibodies in the art use the knob-in-hole technology in the Fc region to prevent Fc homodimerization. However, the knob-in-hole technique cannot completely prevent Fc homodimerization; there still remains 5-10% homodimers that could cause toxic side effects in humans. It should be noted that the bispecific antibodies of the present invention can be made to have 100% heterodimer due to the use of monomeric Fc (mFc) domains disclosed herein.

In some embodiments of the current bispecific antibodies in the art, a single-chain Fv (scFv), which is a single polypeptide chain containing a light chain variable domain (VL) and a heavy chain variable domain (VH), is used as the antigen binding domain. A problem in the uses of scFv is that it would typically lead to instability of the bispecific antibodies. It should be noted that the bispecific antibodies of the present invention do not contain any scFv, thereby avoiding the instability problem of scFv.

Another distinctive feature of the present bispecific antibodies is that long flexible motifs (e.g., repeats of the G4S motif or naturally occurring short heterodimerization peptides) which have small molecular size and low or no immunogenicity are used to block antigen binding sites by creating steric hindrance. Such steric hindrance can be removed by specific enzymes in certain microenvironment, for example, tumor-associated proteases. Hence, the bispecific antibodies disclosed herein can be configured to be activated specifically in a disease microenvironment, for example, in the vicinity of a tumor. In contrast, other bispecific antibodies in the art use non-human antibody binding peptides or anti-antibodies to create steric hindrance. Non-human antibody binding peptides could be highly immunogenic, whereas anti-antibodies could create problem in the making and uses of the bispecific antibodies due to their relatively large molecular size.

In one embodiment, the present invention provides bispecific antibodies having monomeric Fc (mFc) polypeptides or fusion molecules comprising human CH2 and CH3 domains, wherein the CH3 domain comprises one or two amino acid substitutions. The amino acid substitutions significantly reduce the ability of the mFc polypeptides to form homodimers. In one embodiment, the reduction in dimerization is 40%, 50%, 60%, 70%, 80%, 90% or 100%. For example, the present invention includes compositions comprising the present bispecific antibodies or mFc-fusion molecules wherein the amount of Fc-Fc homodimerization exhibited by the antibodies or mFc-fusion molecule is less than 60%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. Examples of such modified CH3 domains include, but are not limited to, one of SEQ ID NOs:155-171.

In one embodiment, an Fc polypeptide comprising an antibody CH3 domain with one or two amino acid substitutions/mutations has decreased ability to form homodimers compared to a polypeptide comprising a wild-type CH3 domain. In one embodiment, the substitutions are within the CH3-CH3 homodimerization interface. In another embodiment, the substitutions/mutations could also be in other regions that could induce conformational changes of CH3 leading to abrogation of CH3-CH3 homodimerization. In one embodiment, the Fc polypeptides could have less immunogenicity compared to an Fc polypeptide comprising three or more substitutions.

Antibody heavy chain is a polypeptide composed of VH-CH1-CH2-CH3 fragments from N- to C-terminus, and the amino acid positions are numbered according to the Kabat numbering system that is widely used in the antibody area. Various substitutions or mutations to the Fc portion of an antibody are contemplated. Such variations are designated by the amino acid at that position in the wild-type antibody heavy chain based on the EU numbering scheme of Kabat followed by the amino acid substituted at that position. For example, when the tyrosine at EU position 407 is substituted with methionine, it is designated "Y407M." By "Fc," it is meant a wild-type sequence of amino acids that occurs naturally within a species of animals, e.g., humans. Wild-type sequence may vary slightly between individuals within a population, e.g., different alleles for the various immunoglobulin chains are known in the art.

It is also contemplated that the creation of monomeric Fc-containing polypeptides is not limited to those based on IgG1 Fc but are also applicable to the Fc region of IgG3, IgG4 and other immunoglobulin subclasses including IgA, IgE, IgD, and IgM Unless defined otherwise, all technical and scientific terms used herein have the meaning commonly understood by one of ordinary skill in the art to which this invention belongs.

As used herein, the term "antibody" refers to a protein or polypeptide containing at least one VH or VL region, in many cases a heavy and a light chain variable region. Thus, the term "antibody" encompasses molecules having a variety of formats, including single chain Fv antibodies (scFv, which contain VH and VL regions joined by a linker), Fab, F(ab)2', Fab', scFv:Fc antibodies etc (as described in Carayannopoulos and Capra, Ch.9 in FUNDAMENTAL IMMUNOLOGY, 3rd ed., Paul, ed., Raven Press, New York, 1993, pp. 284-286). The terms "antibody" and "immunoglobulin" can be used synonymously throughout the specification.

As used herein, the term "cross-reactive binding" of an antibody refers to antibody binding to the same antigen from various species, e.g. cross-reactive binding to antigen X refers to antibody binding to antigen X in various species such as humans, monkeys, mice and rats etc.

In one embodiment, the bispecific antibodies disclosed herein having cross-reactive binding to CD3, e.g. binding to human and cynomolgus CD3, which enables toxicology studies in commonly used pharmacologically relevant species such as cynomolgus monkeys in preclinical development of the bispecific antibodies. In another embodiment, amino acid mutations can be introduced to both the light and heavy chains of the anti-CD3 antibody to reduce binding to CD3, thus minimizing localization of the bispecific antibodies to T cells before engagement with antigen-expressing target cells. Bispecific antibodies with decreased affinity for CD3 could potentially diminish unwanted side effects in vivo. These side effects include, but are not limited to, nonspecific activation of T cells, interference with normal immune responses of T cells, and Fc receptor (FcR)-mediated killing of T cells by other cytotoxic cells such as macrophage and NK cells if the bispecific antibodies contain Fc.

The bispecific antibodies of the present invention, whether attached to other sequences or not, can also include insertions, deletions, substitutions, or other selected modifications of particular regions or specific amino acids residues, provided the activity of the bispecific antibodies is not significantly altered or impaired compared to non-modified antibodies. These modifications can provide some additional properties, such as to remove/add amino acids capable of disulfide bonding, to increase its bio-longevity, to alter its secretory characteristics, etc. Methods for generating amino acid sequence variants are readily apparent to one of ordinary skill in the art and can include, for example, site-specific mutagenesis or random mutagenesis. Both naturally occurring and non-naturally occurring amino acids (e.g., artificially-derivatized amino acids) may be used to generate amino acid sequence variants.

Abbreviations

As used herein, "proBiTE" refers to protease cleavable bispecific T cell engager. proBiTE-1, proBiTE-2, and proBiTE-12 are three variants of proBiTE. proBiTE-1 contains a cleavable polypeptide linker comprising the sequence (SEQ ID NO: 58)
GGGGS<u>LSGRSDNH</u>GGGGS (underlined is the substrate of uPA, matriptase and legumain). proBiTE-2 contains a cleavable linker comprising the sequence (SEQ ID NO: 59)
GGGGS<u>GPLGLARK</u>GGGGS (underlined is the substrate of MMP-7). The substrate sequences for both classes of proteases were combined in proBiTE-12, resulting in a dual cleavable linker comprising the GGGGSLSGRSDNHGPLGLARK sequence (SEQ ID NO:60).

As used herein, "proBiTE-1s", "proBiTE-1s1", "proBiTE-1s2" are three proBiTE-1 variants. proBiTE-1s contains a shortened cleavable polypeptide linker comprising the sequence (SEQ ID NO: 61)
G<u>SLSGRSDNH</u>GGGGS (underlined is the substrate of uPA, matriptase and legumain). proBiTE-1s1 contains linker sequence GSGSGRSDNHGGGGS (SEQ ID NO:62). proBiTE-1s2 contains linker sequence GSGGSRSDNHGGGGS (SEQ ID NO:63).

As used herein, "proBiTE-1s1 sp" refers to a bispecific antibody in which the VH and VL domains of anti-EGFR antibody SMET5.2 were fused to the N terminus of the VH and VL domains of anti-CD3 antibody hSP34 Fab. As used herein, bispecific antibody "proBiTE-1s1spg" was derived from proBiTE-1s1sp.

As used herein, "HBiTE" refers to H-shaped bispecific T cell engager; "iBiTE" refers to I-shaped bispecific T cell engager. "iBiTE-sp" refers to a bispecific antibody in which the scFv of anti-EGFR antibody was fused via a G4S linker to the N terminus of the VH-CH1 of hSP34 and therefore, binding to CD3 is not sterically restricted by the linker. As used herein, "HBiTE-spg" was derived from proBiTE- 1s1spg, in which a protease cleavable linker in proBiTE-1s1spg was replaced by a protease non-cleavable linker.

As used herein, "dproBiTE" refers to protease cleavable bispecific T cell engager in which an antigen binding site is sterically restricted by flexible motifs or heterodimerization motifs. "dproBiTE-HE" and "dproBiTE-GS" are two variants of dproBiTE.

Polynucleotides, Vectors, Host Cells

Also provided herein are nucleic acid sequences that encode the bispecific antibodies described herein. Nucleic acids include single stranded and double stranded nucleic acids of any type (e.g., DNA, RNA, DNA/RNA hybrid). Such nucleic acids can be used therapeutically or in methods of producing the present bispecific antibodies.

The nucleic acid sequences encoding the present bispecific antibodies can be part of a vector. Vectors include nucleic acid vectors, such as naked DNA and plasmids, and various viral vectors and hybrid or chimeric viral vectors generally known in the art (see, e.g., Sambrook et al., Molecular Cloning: A Laboratory Manual, 2nd edition, Cold Spring Harbor Laboratory, NY (1989). The vectors can comprise any suitable promoter and other regulatory sequences (e.g., transcription and translation initiation and termination codons which are specific to the type of host cells) to control the expression of the nucleic acid sequence encoding the polypeptides. The promoter can be a native or normative promoter operably linked to the nucleic acid sequences described herein. The selection and construction of promoters, including various constitutive and regulatable promoters, is within the skill of an ordinary artisan.

The present invention also encompasses amino acid or nucleic acid sequences that are functionally equivalent to the amino acid or nucleic acid sequences disclosed herein. Functionally equivalent sequences refer to sequences that are the results of spontaneous or induced modifications, e.g. substitution, deletion, and/or insertion of nucleotides or amino acids. In other words, sequences functionally equivalent are sequences that are "substantially the same" or "substantially identical" to the amino acid or nucleic acid sequences disclosed herein. As it is generally understood in the art, two sequences are generally considered to be "substantially identical" if they contain identical residues in corresponding positions. Amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. In addition to identifying identical sequences, these and other similar programs typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. The relevant stretch can be a complete or full-length sequence, or a partial sequence thereof.

Also provided herein are cells (e.g., isolated host cells) comprising the above nucleic acid sequences. Such cells are useful, for example, as therapeutic agents or for producing the present bispecific antibodies. A person of ordinary skill in the art would readily use any suitable host cells, including prokaryotic and eukaryotic cells. Alternatively, cells from a mammal, such as a human, to be treated in accordance with the methods described herein can be used as host cells. Methods of introducing nucleic acids and vectors into isolated host cells and the culture and selection of transformed host cells in vitro are generally known in the art. In one embodiment, the nucleic acid sequence is transcribed and translated efficiently by the host cells.

In one embodiment, the bispecific antibodies described herein can be produced by a method comprising (a) transforming host cells with a nucleic acid or vector encoding the bispecific antibodies; (b) culturing the cells in culture medium under conditions sufficient to express the bispecific antibodies; and (c) harvesting the bispecific antibodies from the cells or culture medium. The bispecific antibodies can be expressed in prokaryotic cells (e.g., bacteria) or eukaryotic cells (e.g., yeast, insect, or mammalian cells), and subsequently harvested and purified, as necessary, using well-known methods (see, e.g., Sambrook et al. Molecular Cloning: a Laboratory Manual, Cold Spring Elarbor Laboratory Press (1989). Techniques for transforming, culturing, and harvesting polypeptides expressed by a nucleic acid sequence are generally known in the art. For example, one of ordinary skill in the art could readily express the bispecific antibodies of the present invention in a bacterial system, such as E. coli, or fungal systems, such as yeast. Alternatively, the bispecific antibodies can be produced in mammalian, avian, or plant systems. If the bispecific antibodies have poor solubility, the antibodies can be expressed in the form of insoluble inclusion bodies and refolded in vitro using methods generally known in the art.

Pharmaceutical Composition and Methods of Administration

The present bispecific antibodies, nucleic acid molecules, vectors, or host cells can be administered to a mammal alone, or in combination with a carrier (i.e., a pharmaceutically acceptable carrier). By pharmaceutically acceptable is meant a material that is not biologically or otherwise undesirable, i.e., the material can be administered to a mammal without causing any undesirable biological effects or interacting in a deleterious manner with any of the other components of the pharmaceutical composition in which it is contained. As would be well-known to one of ordinary skill in the art, the carrier is selected to minimize any degradation of the bispecific antibodies or polynucleotides and to minimize any adverse side effects in the mammal. For example, suitable carriers and their formulations are described in Remington: The Science and Practice of Pharmacy ($19^{th}$ ed.) ed. A. R. Gennaro, Mack Publishing Company, Easton, Pa. (1995).

The above pharmaceutical compositions comprising the bispecific antibodies, polynucleotides, vectors, or host cells can be administered (e.g., to a mammal, a cell, a tissue, or a tumor) in any suitable manner depending on whether local or systemic treatment is desired. For example, the composition can be administered topically (e.g. ophthalmically, vaginally, rectally, intranasally, transdermally, and the like), orally, by inhalation, or parenterally (including by intravenous drip or subcutaneous, intracavity, intraperitoneal, intradermal, or intramuscular injection). Topical intranasal administration refers to delivery of the compositions into the nose and nasal passages through one or both of the nares. The composition can be delivered by a spraying mechanism or droplet mechanism, or through aerosolization of the nucleic acid or vector. Delivery can also be directed to any area of the respiratory system (e.g., lungs) via intubation. Alternatively, administration can be intratumoral, e.g. local or intravenous injection.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve preparation of a slow-release or sustained-release system so as to maintain a constant dosage.

In one embodiment, the present bispecific antibodies, polynucleotides, vectors, or host cells can be delivered to a mammal in vivo and/or ex vivo by a variety of mechanisms well-known in the art. If ex vivo methods are employed, cells or tissues can be removed from the mammal and maintained outside the body according to standard protocols known in the art. The nucleic acid molecules or vectors can be introduced into the cells or tissue via any gene transfer mechanism well-known in the art. The transduced cells are then infused or homotopically transplanted back into the mammal according to standard methods.

The bispecific antibodies disclosed herein may be used in therapeutic methods. In one embodiment, the bispecific antibodies of the present invention can be used as immunotherapeutic agents, for example in the treatment of cancers. In one embodiment, the bispecific antibodies of the present invention can be used alone or in combination with other anti-cancer therapies, such as chemotherapy and radiotherapy. The present bispecific antibodies can be administered to the mammal directly, or by administering to the mammal a nucleic acid sequence encoding the bispecific antibodies, such nucleic acid sequence may be carried by a vector.

The exact amount of the bispecific antibodies, polynucleotides, vectors, or host cells or compositions thereof required to elicit the desired effects will vary from mammal to mammal, depending on the species, age, gender, weight, and general condition of the mammal, the particular bispecific antibodies, nucleic acid molecules, vectors, or cells used, the route of administration, and whether other drugs are included in the regimen. Thus, it is not possible to specify an exact amount for every composition. However, an appropriate amount can be determined by one of ordinary skill in the art using routine experimentation. Dosages can vary, and the antibodies can be administered in one or more (e.g., two or more, three or more, four or more, or five or more) doses daily, for one or more days. Guidance in selecting appropriate doses for antibodies can be readily found in the literature.

The present invention also provides kits comprising the bispecific antibodies, polynucleotides, vectors, or host cells, or compositions thereof. The kit can include a separate container containing a suitable carrier, diluent, or excipient. The kit also can include an adjuvant, cytokine, active agent, immunoassay reagents, PCR reagents, radiolabels, and the like. Additionally, the kit can include instructions for mixing or combining ingredients and/or methods of administration.

In one embodiment, the present invention provides a recombinant bispecific antibody, comprising
(i) a first polypeptide comprising from N- to C-terminus a first light chain variable domain, a human light chain constant region (CL), a human heavy chain constant region 2 (CH2) and a human heavy chain constant region 3 (CH3);
(ii) a second polypeptide comprising from N- to C-terminus a first heavy chain variable domain, a human heavy chain constant region 1 (CH1), a human heavy chain constant region 2 (CH2) and a human heavy chain constant region 3 (CH3); and
(iii) a second light chain variable domain connected to the first light chain variable domain by a first linker, and a second heavy chain variable domain connected to the first heavy chain variable domain by a second linker,
wherein the first light chain variable domain and the first heavy chain variable domain confer binding specificity to a first antigen, the second light chain variable domain and the second heavy chain variable domain confer binding specificity to a second antigen.

In one embodiment, the present invention provides a recombinant bispecific antibody, comprising
(i) a first polypeptide comprising from N- to C-terminus a first light chain variable domain, a human light chain constant region (CL), a human heavy chain constant region 2 (CH2) and a human heavy chain constant region 3 (CH3);
(ii) a second polypeptide comprising from N- to C-terminus a first heavy chain variable domain, a human heavy chain constant region 1 (CH1), a human heavy chain constant region 2 (CH2) and a human heavy chain constant region 3 (CH3); and
(iii) a second light chain variable domain connected to the C-terminus of the CH3 of the first polypeptide by a first linker, and a second heavy chain variable domain connected to the C-terminus of the CH3 of the second polypeptide by a second linker,
wherein the first light chain variable domain and the first heavy chain variable domain confer binding specificity to a first antigen, the second light chain variable domain and the second heavy chain variable domain confer binding specificity to a second antigen.

In one embodiment, the amino acid sequences of the heavy or light chain variable domains of the present bispecific antibody are derived from human. Alternatively, the heavy or light chain variable domains are derived from non-human species. In yet another embodiment, the heavy or light chain variable domains can be derived from humanized antibodies. As used herein, "humanized antibody" refer to a type of recombinant antibody resulted from combining a human antibody with a small part of a mouse or rat monoclonal antibody. The mouse or rat part of the antibody binds to the target antigen, whereas the human part makes it less likely to be destroyed by the body's immune system. One of ordinary skill in the art would readily construct humanized antibodies using standard techniques in the art.

In one embodiment, the present bispecific antibodies are designed to bind to a first antigen on target cells and to a second antigen on immune cells such as T cells. Examples of the first antigen on target cells include, but are not limited to, EpCAM, HER2, PSMA, gpA33, CD276, EGFR, CEA, CD19, CD20, CD22, CD30, CD33, CD123, FLT3 and BCMA. Examples of the second antigen on immune cells include, but are not limited to, CD3, FcγRI, and FcγRIIIa.

In one embodiment, one or both of the human CH3 domains of the present bispecific antibodies comprise one or more amino acid substitutions that confer decreased or abrogated homodimerization between the first and second polypeptides. For example, amino acid T366 of the one or both CH3 is substituted with D (Aspartic Acid), L (Leucine), W (Tryptophan) or N (Asparagine). In another embodiment, amino acid Y407 of the one or both CH3 is substituted with I (Isoleucine), F (Phenylalanine), L (Leucine), M (Methionine), H (Histidine), K (Lysine), S (Serine), Q (Glutamine), T (Threonine), W (Tryptophan), A (Alanine), G (Glycine) or N (Asparagine). In one embodiment, one or both of the CH3 domains of the present bispecific antibodies comprise an amino acid sequence of one of SEQ ID NOs:155-171.

In one embodiment, the first or second linker of the present bispecific antibodies comprises amino acid sequence of SEQ ID NO:125, 126 or 127. One of ordinary skill in the art would readily understand that the linkers need to have length, flexibility and orientations to a degree that allows stable interactions between the VH and VL domains that bind to a first antigen, and simultaneously, efficient blockade of binding to a second antigen.

In another embodiment, the first or second linker of the present bispecific antibodies comprises a protease cleavage site. For example, the protease cleavage site comprises amino acid sequence of one of SEQ ID NOs:58-63. Further examples of protease cleavage sites include, but are not limited to, for matrix metalloproteases (MMP): PLGLWA (SEQ ID NO:128), GPLGLWA (SEQ ID NO:129), GPLGL-WAQ (SEQ ID NO:130), GVPDLGRFQTFE (SEQ ID NO:131), GVPDVGHFSLFP (SEQ ID NO:132), GVPDVGEFSLFP (SEQ ID NO:133), GVPDVGNFSLFP (SEQ ID NO:134), GVPDVGRFSLFP (SEQ ID NO:135), GVPDVGHYSLFP (SEQ ID NO:136), GVPDVGEYSLFP (SEQ ID NO:137), GVPDVGNYSLFP (SEQ ID NO:138), GVPDVGRYSLFP (SEQ ID NO:139); for urokinase (uPA): PRFKIIGG (SEQ ID NO:140), PRFRIIGG (SEQ ID NO:141); for TGFβ: SSRHRRALD (SEQ ID NO:142); for plasminogen: RKSSIIIRMRDVVL (SEQ ID NO:143); for staphylokinase: SSSFDKGKYKKGDDA (SEQ ID NO:144); for factor Xa: IEGR (SEQ ID NO:145), IDGR (SEQ ID NO:146), GGSIDGR (SEQ ID NO:147); for human liver collagen: GPLGIAGI (SEQ ID NO:148); for human α2M: GPEGLRVG (SEQ ID NO:149); for human PZP: YGAGLGVV (SEQ ID NO:150), AGLGVVER (SEQ ID NO:151), AGLGISST (SEQ ID NO:152).

In one embodiment, the CH1 and CL of the present bispecific antibodies are connected to the CH2 of the first and second polypeptides via a linker that comprises a shortened hinge sequence as compared to a hinge sequence in normal human IgG.

In one embodiment, the recombinant bispecific antibody of the present invention comprises a polypeptide comprising amino acid sequence of one of SEQ ID NOs: 1-16. In another embodiment, the recombinant bispecific antibody of the present invention comprises a polypeptide that is at least 85%, 90%, 92%, 94%, 96%, 98% or 99% identical to one of the amino acid sequences of SEQ ID NOs: 1-16.

In one embodiment, the recombinant bispecific antibody of the present invention further comprise a heterodimerization motif or a long flexible motif, wherein the heterodimerization motif or long flexible motif is connected to the N terminus of the second light chain variable domain and the second heavy chain variable domain via one or more linkers. In one embodiment, such one or more linkers comprise a protease cleavage site. In one embodiment, the heterodimerization motif comprises a N-terminal heterodimerization motif of human HER2 transmembrane domain or a N terminal heterodimerization motif of human EGFR transmembrane domain. In another embodiment, the heterodimerization motifs must have fully human sequences for minimized immunogenicity, are short for small molecular size, and have sufficient heterodimerization strength to ensure efficient blockade of antigen binding activity. One of ordinary skill in the art would readily recognize heterodimerization motifs from human proteins other than EGFR and HER2.

In one embodiment, the long flexible motif comprises an amino acid sequence GGGGSGGGGS (SEQ ID NO:153). One of ordinary skill in the art would understand that the long flexible motifs must have length, flexibility and orientations to a degree that allows efficient interruption of antigen binding activity. Further examples of such flexible motifs include, but are not limited to, any repeats of the G4S sequence or other unstructured recombinant polypeptide such as XTEN (Schellenberger et al., Nature Biotechnology 2009, 27: 1186-1190).

In one embodiment, the recombinant bispecific antibody comprising such heterodimerization motif or long flexible motif contains a polypeptide comprising amino acid sequence of one of SEQ ID NOs: 17-20. In another embodiment, the recombinant bispecific antibody of the present invention comprises a polypeptide that is at least 85%, 90%, 92%, 94%, 96%, 98% or 99% identical to one of the amino acid sequences of SEQ ID NOs: 17-20.

Bispecific Antibodies with Modified Binding to CD3

In one embodiment, a light chain variable domain and a heavy chain variable domain of the recombinant bispecific antibody comprise modified sequences that confer reduced binding affinity to CD3 as compared to that mediated by unmodified sequences. In another embodiment, a light chain variable domain and a heavy chain variable domain of the recombinant bispecific antibody confer binding specificity to human CD3 and cynomolgus CD3. In one embodiment, such bispecific antibody comprises a polypeptide comprising amino acid sequence of one of SEQ ID NOs:50-57.

In one embodiment, the present invention also provides a polynucleotide encoding one or more polypeptides disclosed above. In another embodiment, the present invention also provides an expression vector comprising one or more of the above polynucleotides. In another embodiment, the present invention also provides a host cell comprising such expression vector.

In one embodiment, the present invention also provides a method of preparing the recombinant bispecific antibody disclosed herein, the method comprises the steps of: (a) culturing host cells comprising one or more polynucleotides encoding the present recombinant bispecific antibody under conditions wherein such recombinant bispecific antibody is expressed; and (b) recovering the recombinant bispecific antibody from the host cells.

Anti-EGFR Antibodies

In one embodiment, the present invention also provides an isolated anti-human EGFR (epidermal growth factor receptor) antibody comprising a heavy chain and a light chain. In one embodiment, the heavy chain comprises a complementarity determining region 1 (CDR1) comprising amino acid sequence SEQ ID NO:22, a CDR2 comprising amino acid sequence SEQ ID NO:23, and a CDR3 comprising amino acid sequence SEQ ID NO:24. In one embodiment, the heavy chain comprises amino acid sequence SEQ ID NO:21 (the VH domain). In another embodiment, the heavy chain comprises amino acid sequence SEQ ID NO:44 (a full length heavy chain). The above sequences are derived from antibody designated as SMET5.

In another embodiment, the light chain of the anti-human EGFR antibody comprises a CDR1 comprising amino acid sequence SEQ ID NO:26, a CDR2 comprising amino acid sequence SEQ ID NO:27, and a CDR3 comprising amino acid sequence SEQ ID NO:28. In one embodiment, the light chain comprises amino acid sequence SEQ ID NO:25 (the VL domain). In another embodiment, the light chain comprises amino acid sequence SEQ ID NO:45 (a full length light chain). The above sequences are derived from antibody designated as SMET5.

In another embodiment, the light chain of the anti-human EGFR antibody comprises a CDR1 comprising amino acid sequence SEQ ID NO:31, a CDR2 comprising amino acid sequence SEQ ID NO:32, and a CDR3 comprising amino acid sequence SEQ ID NO:33. In one embodiment, the light chain comprises amino acid sequence SEQ ID NO:30 (the VL domain). In another embodiment, the light chain comprises amino acid sequence SEQ ID NO:47 (a full length light chain). The above sequences are derived from antibody designated as SMET5.2.

In another embodiment, the light chain of the anti-human EGFR antibody comprises a CDR1 comprising amino acid sequence SEQ ID NO:36, a CDR2 comprising amino acid sequence SEQ ID NO:37, and a CDR3 comprising amino acid sequence SEQ ID NO:38. In one embodiment, the light chain comprises amino acid sequence SEQ ID NO:35 (the VL domain). In another embodiment, the light chain comprises amino acid sequence SEQ ID NO:49 (a full length light chain). The above sequences are derived from antibody designated as SMET5.3.

In another embodiment, the light chain of the anti-human EGFR antibody comprises a CDR1 comprising amino acid sequence SEQ ID NO:41, a CDR2 comprising amino acid sequence SEQ ID NO:42, and a CDR3 comprising amino acid sequence SEQ ID NO:43. In one embodiment, the light chain comprises amino acid sequence SEQ ID NO:40 (the VL domain). The above sequences are derived from antibody designated as SMET5.4.

In another embodiment, the present invention also provides a composition comprising a physiologically acceptable carrier and a therapeutically effective amount of any one of the anti-human EGFR antibodies described above.

The invention being generally described will be more readily understood by reference to the following examples that are included merely for purposes of illustration of certain aspects and embodiments of the present invention, and are not intended to limit the invention.

Throughout this application, various references or publications are cited. Disclosures of these references or publications in their entireties are hereby incorporated by reference into this application in order to more fully describe the state of the art to which this invention pertains.

Example 1

Materials and Methods

Cells, Proteins, Plasmids and Other Reagents 293 free style (293FS) cells and protein A agarose were purchased from ThermoFisher Scientific. HCT116, HT29 and SW480 colon cancer cell lines were purchased from Sigma. Other cell lines were purchased from ATCC. Recombinant human EGFR, Fc gamma receptor (FcγR), and urokinase (uPA) were products of Sino Biological and recombinant human MMP-7 protease was a product of Biolegend. The pDin1 vector used for mammalian expression was synthesized and assembled by overlapping PCR and ligation. The vector contains two transcription units and a built-in human IgG1 Fc gene fragment without introns that facilitates cloning of IgG1 or Fc-fusion proteins. Horseradish peroxidase (HRP)-conjugated goat anti-human IgG (Fc-specific) antibody was a product of Sigma. Goat anti-human IgG (Fc-specific)-FITC conjugate was purchased from ThermoFisher Scientific.

Cloning of EGFR×CD3 Bispecific Antibodies

The following primers were used:
OKTVLF, (sense) (SEQ ID NO:68); OKTVLR, (antisense) (SEQ ID NO:69)
CKF1, (sense) (SEQ ID NO:70); CKR1, (antisense) (SEQ ID NO:71)
MFCPAF, (sense) (SEQ ID NO:72); AAAR, (antisense) (SEQ ID NO:73)
OKT3 VHF, (sense) (SEQ ID NO:74); OKT3VHR, (antisense) (SEQ ID NO:75)
CHMFCF, (sense) (SEQ ID NO:76); CHMFCR, (antisense) (SEQ ID NO:77)
bnIgG20H1, (sense) (SEQ ID NO:78)
12VHF, (sense) (SEQ ID NO:79); 12VHR, (antisense) (SEQ ID NO:80)
12VLF, (sense) (SEQ ID NO:81); 12VLR, (antisense) (SEQ ID NO:82)
bnIgG20L1, (sense) (SEQ ID NO:83)
CHF, (sense) (SEQ ID NO:84); CHF1, (sense) (SEQ ID NO:85); CHF2, (sense) (SEQ ID NO:86)
H12LR, (antisense) (SEQ ID NO:87)
ISIF, (sense) (SEQ ID NO:88); 1 S2F, (antisense) (SEQ ID NO:89)
HEHR, (antisense) (SEQ ID NO:90); HEHF, (sense) (SEQ ID NO:91)
HEHR1, (antisense) (SEQ ID NO:92); HELR, (antisense) (SEQ ID NO:93)
HELF, (sense) (SEQ ID NO:94); HELR1, (antisense) (SEQ ID NO:95)
GSHR, (antisense) (SEQ ID NO:96); GSHF, (sense) (SEQ ID NO:97)
GSLR, (antisense) (SEQ ID NO:98); GSLF: (sense) (SEQ ID NO:99)

Cloning of iBiTE iBiTE was cloned as follows. To clone the light chain of iBiTE, the VL domain of humanized anti-CD3 antibody OKT3 (hOKT3), the human antibody kappa light chain constant domain (CK), and a monomeric human IgG1 Fc (mFc7.2)-poly A signal sequence were PCR amplified with primer pairs OKTVLF/OKTVLR, CKF1/CKR1 and MFCPAF/AAAR, and their encoding plasmids as templates, respectively. hOKT3 VL was joined to the 5' end of CK gene fragment by using overlapping PCR with the two gene fragments in the same molarities for 7 cycles in the absence of primers and 15 additional cycles in the presence of primers OKTVLF and CKR1. In the same way, a gene fragment (Hleader) encoding a leader peptide was fused to the 5' end of the hOKT3 VL-CK fragment by overlapping PCR with primers bnIgG20H1 and CKR1. The Hleader-hOKT3 VL-CK was further linked to the 5' end of the mFc7.2-poly A by overlapping PCR with primers bnIgG20H1 and AAAR. The final PCR product was digested with XbaI and SalI and cloned into pDin1.

To clone the heavy chain of iBiTE, the hOKT3 VH and human IgG1 CH1-mFc7.2 gene fragments were PCR amplified with primer pairs OKT3VHF/OKT3VHR and CHMFCF/CHMFCR, respectively. The OKT3VHF primer carries the HindIII and SacI restriction sites which will be used for subcloning. The hOKT3 VH gene fragment was fused to the 5' end of CH1-mFc7.2 by overlapping PCR with primers OKT3VHF and CHMFCR. The product was digested with HindIII and EcoRI and cloned into the pDin1 construct containg iBiTE light chain. A gene fragment encoding a leader peptide (Lleader) and an anti-EGFR scFv was obtained by digestion of a previously constructed plasmid with HindIII and SacI, and then cloned into the plasmid containing the full-length light chain and partial heavy chain of iBiTE, leading to the final iBiTE construct.

Cloning of HBiTE

To clone HBiTE, the VH and VL domains of anti-EGFR antibody were PCR amplified with primer pairs 12VHF/12VHR and 12VLF/12VLR, respectively. The PCR products were fused to the 3' end of Lleader and Hleader by overlapping PCR with primer pairs bnIgG20L1/12VHR and bnIgG20H1/12VLR, respectively. The Hleader-VL gene fragment was digested with XbaI and BamHI and cloned into an iBiTE-derived vector with HindIII and BamHI restriction sites introduced into the 5' end of the hOKT3 VL domain. The Lleader-VH gene fragment was then further cloned into the construct containing the Hleader-VL insert via the HindIII and SacI restriction sites.

Cloning of proBiTE Variants

The proBiTE variants were cloned by using HBiTE as a template. For cloning of proBiTE-1, proBiTE-2 and proBiTE-12, the hOKT3 VL-CK-mFc7.2-poly A gene fragments were PCR amplified with HBiTE as a template and primer pairs CHF/AAAR, CHF1/AAAR and CHF2/AAAR, respectively. The PCR products were digested with BamHI and SalI and cloned into HBiTE.

Cloning of proBiTE-1s

For cloning of proBiTE-1 s, the Hleader-VL fragment was PCR amplified with primers bnIgG20H1 and H12LR. The PCR product was digested with XbaI and BamHI and cloned into proBiTE-1 linearized with the same restriction enzymes. proBiTE-1s1 and proBiTE-1s2 were cloned the same way as proBiTE-1 was generated except that primer pairs 1S1F/AAAR and 1S2F/AAAR were used for PCR amplification of the hOKT3 VL-CK-mFc7.2-poly A gene fragments.

Cloning of dproBiTE-HE

To clone dproBiTE-HE, Lleader and anti-EGFR VH domain were PCR amplified with primer pairs bnIgG20L1/HEHR and HEHF/HEHR1, respectively. Lleader gene fragment was then fused to the 5' end of anti-EGFR VH by overlapping PCR with primers bnIgG20L1 and HEHR1. The full-length Lleader-anti-EGFR VH gene fragment was digested with HindIII and SacI and cloned into proBiTE-1s1. The Hleader-anti-EGFR VL gene fragment was obtained and cloned in the same way except the use of bnIgG20H1/HELR and HELF/HELR1 primer pairs for primary amplification and XbaI and BamHI restriction sites for cloning.

Cloning of dproBiTE-GS

To clone dproBiTE-GS, Lleader and anti-EGFR VH domain were PCR amplified with primer pairs bnIgG20L1/GSHR and GSHF/HEHR1, respectively. Lleader gene fragment was then fused to the 5' end of anti-EGFR VH by overlapping PCR with primers bnIgG20L1 and HEHR1. The full-length Lleader-anti-EGFR VH gene fragment was digested with HindIII and SacI and cloned into proBiTE-1s1. The Hleader-anti-EGFR VL gene fragment was obtained and cloned in the same way except the use of bnIgG20H1/GSLR and GSLF/HELR1 primer pairs for primary amplification and XbaI and BamHI restriction sites for cloning.

Protein Expression And Purification

All bispecific antibodies were expressed in 293FS cells as described previously (Chen et al., Proc Natl Acad Sci USA 2008, 105: 17121-17126) and purified from the 293FS culture supernatant using Protein A Sepharose 4 Fast Flow column chromatography (GE Healthcare) according to the manufacturer's instructions.

Protease Cleavage

For cleavage with urokinase (uPA), five μg antibodies were mixed with or without 1 μg recombinant human uPA (Sino Biological) in 15 μl PBS (pH7.4) and incubated at room temperature for 1 h. For cleavage with MMP-7, recombinant human MMP-7 (Biolegend) was diluted in the assay buffer (50 mM Tris, 10 mM CaCl2, 150 mM NaCl, 0.05% Brij-35, pH7.5) and activated by adding 4-aminophenylmercuric acetate (APMA) to a final concentration of 1 mM and incubating the mixture for 30 min at 37° C. Then, 4 μg antibodies were mixed with or without 0.5 μg is activated MMP-7 in 20 μl assay buffer and incubated at 37° C. for 1 h.

ELISA

ELISA was performed according to standard protocols. Briefly, recombinant human FcγRs (Sino Biological) were coated on Corning EIA/RIA high-binding 96-well plates (Corning Inc.) at 50 ng per well overnight at 4° C. and blocked with 3% nonfat milk in PBS (pH7.4). Fivefold serially diluted biotinylated antibodies were added and incubated at room temperature for 2 h. The plates were washed with PBS containing 0.05% Tween 20. Bound antibodies were detected by HRP-conjugated streptavidin (ThermoFisher Scientific). The assay was developed at room temperature with TMB substrate (Sigma-Aldrich) and monitored at 450 nm with a microplate reader. The half-maximal binding ($EC_{50}$) was calculated by fitting the data to the Langmuir adsorption isotherm.

Flow Cytometry

About $5 \times 10^5$ cells were incubated with antibodies on ice for 1 h. The cells were washed once with PBS containing 0.1% bovine serum albumin (PBSA) and resuspended in 100 μl PBSA. Then 1 μl goat anti-human IgG (Fc-specific)-FITC conjugate (Invitrogen) was added and incubated for 30 min. The cells were washed once with PBSA and then used for flow cytometry analysis.

Size-Exclusion Chromatography

A Superdex200 10/300 GL column (GE Healthcare) was calibrated with protein molecular mass standards of carbonic anhydrase (29 kDa), ovalbumin (44 kDa), conalbumin (75 kDa), aldolase (158 kDa) and ferritin (440 kDa). Purified proteins at a concentration of 1 mg $mL^{-1}$ in PBS (pH7.4) were loaded onto the pre-equilibrated column and eluted with PBS (pH7.4) at 0.5 mL/min.

T Cell Activation Assay

Target cells were plated on 96-well plates at a density of $2 \times 10^4$ cells in 25 μl RPMI1640 complete medium per well. Fifty μl antibodies 5-fold serially diluted were added into each well. Then effector cells (Jurkat NFAT-Luc2, Promega) were added at a density of $1 \times 10^5$ cells in 25 μl RPMI1640 complete medium per well to make a target:effector cell ratio of 1:5. The assay was developed after 5-h incubation by using the Promega Bio-Glo Luciferase Assay System according to the manufacture's instructions.

In Vitro Killing Assay

Target cells ($2 \times 10^4$) stably transfected with red firefly luciferase gene were seeded in 100 μl RPMI 1640 complete medium overnight. Meanwhile, $2.5 \times 10^7$ frozen PBMC purchased from STEMCELL Technologies were revived and inoculated in 10 mL RPMI 1640 complete medium containing 50 U/mL IL-2 (Sigma) overnight. The second day, the medium was removed from target cells and $2 \times 10^5$ PBMC in 50 μl RPMI 1640 complete medium (actual target:effector ratio=1:5 because target cells duplicate overnight) were added. Then, 50 μl antibodies 5-fold serially diluted from 10 nM were added into each well. 72 h after incubation, cell killing activity was measured by using the Promega Bio-Glo Luciferase Assay System according to the manufacture's instructions.

Pharmacokinetic Measurement in Mice

NOD/SCID mice were administered intravenously with 500 μg antibody on day 0. Plasma samples were collected on day 1, 3, 5 and 6 or 7 or 8 and used for measurement of antibody serum concentrations by ELISA with standard curves generated using the original antibody stocks.

In-Vivo Tumor Growth Inhibition

SCID mice were inoculated with a mixture of $2 \times 10^6$ HCT116 cells and $10^7$ freshly isolated human PBMC subcutaneously into the left flank of the mice. The mice were dosed intravenously with PBS (control) or 20 μg antibody 6 h later and then every other day for 6 doses. After two weeks of treatment, mice were sacrificed and tumor weights were measured. Tumor growth inhibition rates were calculated by using the following formula: average weight of PBS group—average weight of antibody treated group/average weight of PBS group.

Example 2

Rational Design of Protease Cleavable Bispecific T Cell Engagers (proBiTE) with Sterically Restricted Access of One Antigen Binding Site Bispecific T cell engager (BiTE) is a novel class of bispecific antibodies that can guide cytotoxic T cells to kill cancer cells by simultaneously binding to a tumor antigen and the CD3 molecule on T cell surface. However, expression of some tumor antigens in normal tissues manifests dose-limiting on-target toxicity. Off-target toxicity such as cytokine release syndrome also limits their clinical use. It is hypothesized that multiple strategies aimed at increasing tumor selectivity could be combined to minimize such toxicities and enlarge therapeutic windows of this class of bispecific antibodies. These strategies include optimization of antibody affinity for both tumor antigen and CD3, introduction of second tumor specificity, and minimization of FcR binding activity when Fc is included in BiTE for long half-life in vivo.

Some of the above goals could be accomplished by rational design of molecular structures of bispecific antibodies. For example, some proteases are highly up-regulated in a variety of tumors and play a critical role in cancer invasion and metastasis. Expression of these proteases and their proteolytic activities in healthy tissues are minimal. Therefore, employing tumor-associated proteases in the design of BiTE could be helpful to increase tumor selectivity leading to the generation of prodrugs for cancer therapy.

To test this possibility, a novel class of proBiTE with sterically restricted access of one antigen binding site was designed, in which the VH and VL domains of the first antibody are fused to the N terminus of the VH and VL domains of a second antibody Fab via a protease non-cleavable polypeptide linker or a protease cleavable polypeptide linker. The second antibody Fab is further fused to the N terminus of a human antibody Fc region which contains mutations capable of decreasing or abrogating Fc homodimerization via a polypeptide linker without protease cleavage site (FIG. 1A).

Figure 1B:
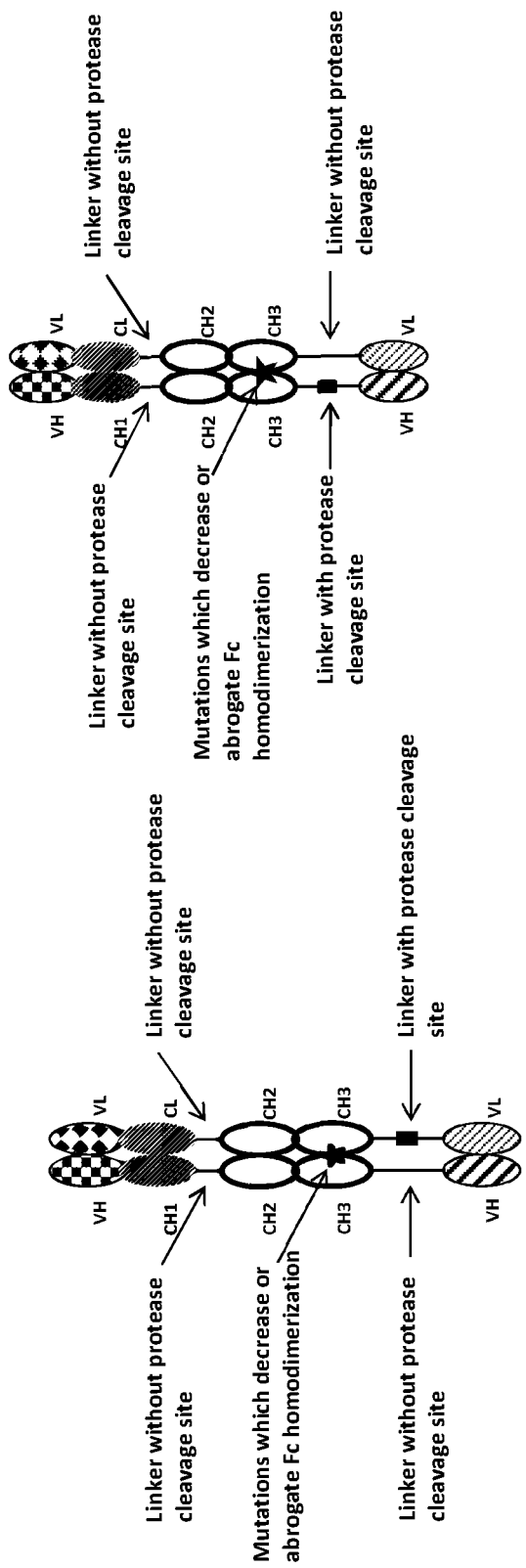
FIG. 1B shows schematic representation of examples of another embodiment of protease cleavable bispecific antibodies of the present invention.

In another embodiment of proBiTE, the VH and VL domains of the first antibody are fused to the C teminus of a human antibody Fc region which contains mutations capable of decreasing or abrogating Fc homodimerization via a polypeptide linker with or without protease cleavage site. The human Fc region is further fused to the C terminus of a second antibody Fab via a polypeptide linker without protease cleavage site (FIG. 1B). proBiTE exhibits monovalent binding for each antibody and therefore, should not nonspecifically activate T cells before engagement with tumor cells.

Figure 2A:
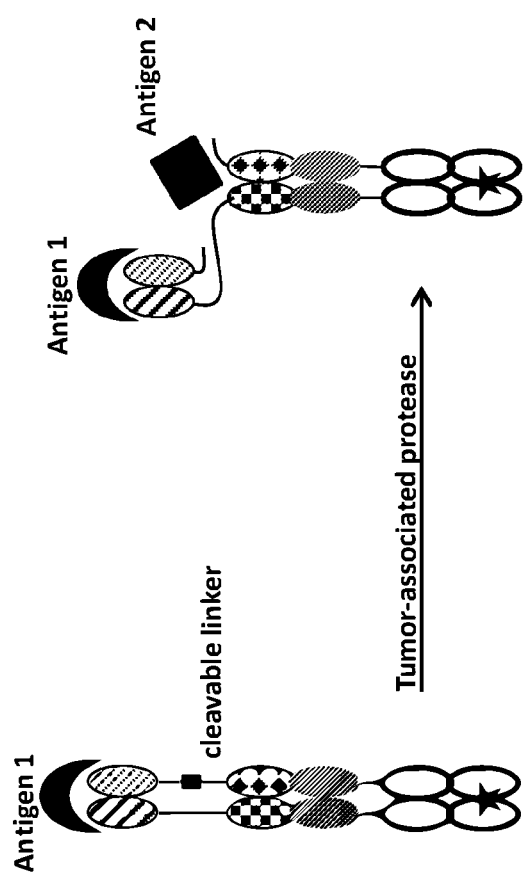
FIG. 2A shows a mechanism of action of the bispecific antibodies of the present invention in the absence or presence of tumor-associated proteases. Stars denote mutations which decrease or abrogate Fc homodimerization. All unlabeled modules have the same meanings as in FIGS. 1A-B.
Figure 2B:
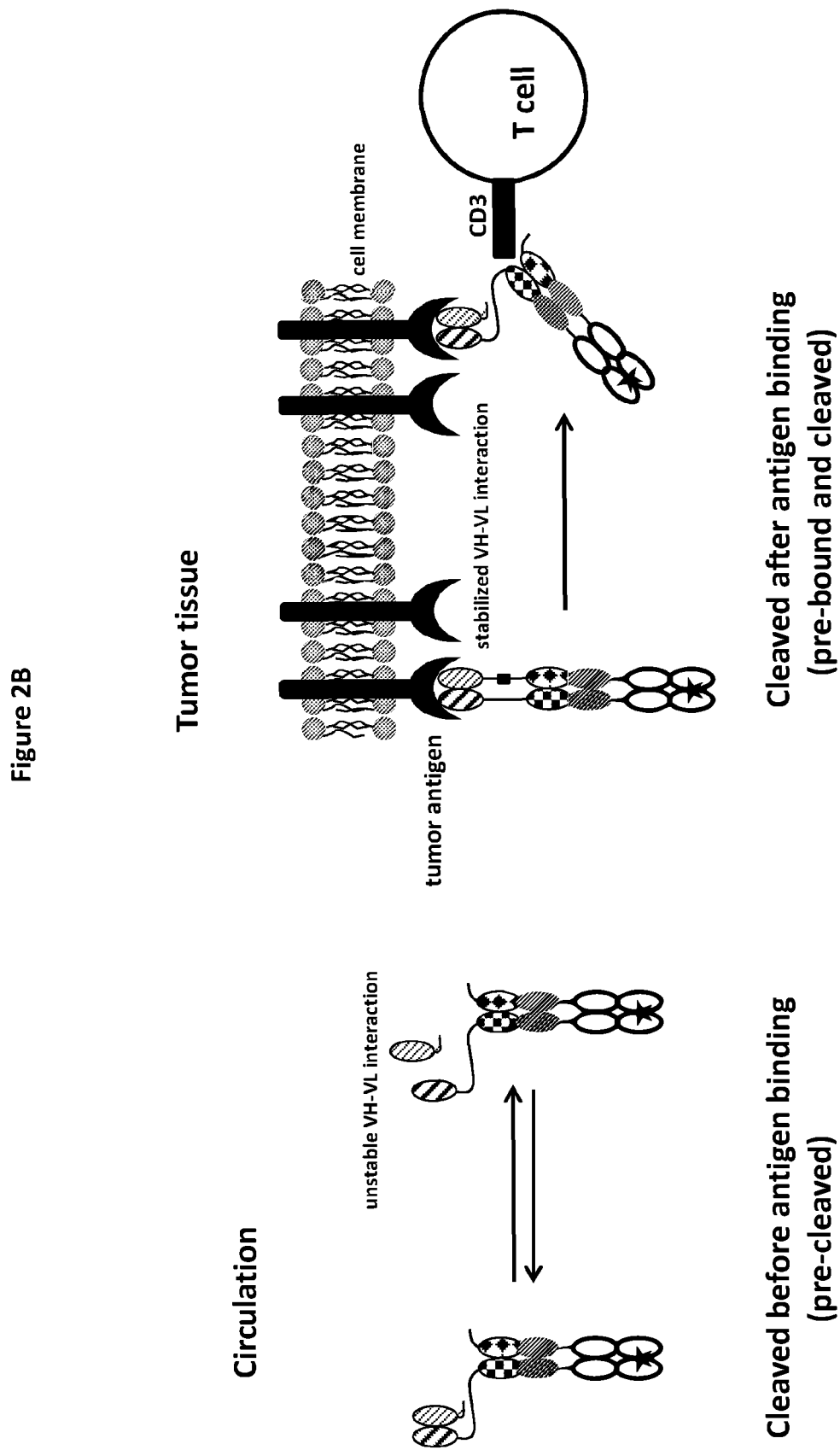
FIG. 2B shows mechanisms of action of the bispecific antibodies of the present invention in circulation (left panel) and in tumor tissue (right panel). Stars denote mutations which decrease or abrogate Fc homodimerization. All unlabeled modules have the same meanings as in FIGS. 1A-B.

A mechanism of action of the proBiTE is proposed as follows: in the absence of tumor-associated proteases, proBiTE binds to one antigen (antigen 1) but not or only weakly to the other antigen (antigen 2) due to steric hindrance caused by the polypeptide linkers connecting the two antibodies (FIG. 2A). In the tumor microenvironment where protease expression is up-regulated, efficient cleavage of the polypeptide linker by the proteases resolves the steric hindrance allowing proBiTE to bind to the other antigen (antigen 2) and exert its functions. Some tumor-associated proteases are secreted into the circulation as active soluble proteins. In one design of proBiTE, the VH and VL domains of the tumor antigen-binding antibody are fused to the N terminus of the VH and VL domains of the Fab of a CD3 antibody via a protease non-cleavable and cleavable polypeptide linker, respectively. Because cooperation between VH-VL and CH1-CL interface is required for mutual stabilization of the domains, the integrity and activity of proBiTE should be compromised when the antibody is cleaved in the circulation due to unstable VH-VL interaction of the tumor antigen-binding antibody (FIG. 2B, left panel). In tumor tissues, however, proBiTE bound to tumor antigens could be stabilized due to cooperation between the VH-VL and antibody-antigen interface, leading to retained full function of the bispecific antibodies even after cleavage by proteases (FIG. 2B, right panel). It is therefore hypothesized that this unique proBiTE design could further decrease on-target toxicity of this class of bispecific antibodies.

In summary, as compared to published monovalent bispecific antibodies developed by others, the bispecific antibodies of the present invention have the distinctive features of using (i) monomeric Fc domain, for example, human IgG1 Fc, to extend in vivo half-life, and (ii) only two polypeptide chains and employ both Fab and Fv for heterodimerization and antigen recognition. A combination of the features mentioned herein results in excellent properties for the present bispecific antibodies such as 100% heterodimer, high yield, high stability and low aggregation propensities.

Example 3

Generation and Initial Characterization of EGFR×CD3 Bispecific Antibody

To provide a proof-of-concept and test the above hypothesis, a proBiTE targeting EGFR and CD3 was generated. EGFR and CD3 were used as examples here and below. One of ordinary skill in the art would recognize that other T and non-T cell target antigens can be readily employed as described herein.

In one embodiment, the VH and VL domains of an anti-EGFR antibody were fused to the N terminus of the VH and VL domains of an anti-CD3 antibody Fab via a protease non-cleavable (G4S)3 linker and a protease cleavable linker, respectively. The anti-CD3 Fab was further fused to the N terminus of a monomeric human IgG1 Fc (mFc7.2) (SEQ ID NO:172) which contained two amino acid mutations (T366L/Y407H) capable of decreasing Fc homodimerization (FIG. 3). mFc7.2 exists as a monomer at low concentrations (<0.5 mg/mL) but tends to form a dimer at higher concentrations. It is therefore conceivable that when the heavy and light chains of proBiTE are assembled, mFc7.2 could form a dimer due to high local concentrations and further stabilize the bispecific antibodies.

In one embodiment, three proBiTE variants were generated. proBiTE-1 contains a cleavable polypeptide linker composed of the sequence
(SEQ ID NO: 58)
GGGGSLSGRSDNHGGGGS (underlined is the substrate of uPA, matriptase and legumain). proBiTE-2 contains a cleavable linker composed of the sequence
(SEQ ID NO: 59)
GGGGSGPLGLARKGGGGS (underlined is the substrate of MMP-7). The substrate sequences for both classes of proteases were combined in proBiTE-12, resulting in a dual cleavable linker composed of the GGGGSLSGRSDNHGPLGLARK sequence (SEQ ID NO:60).

Figure 3:
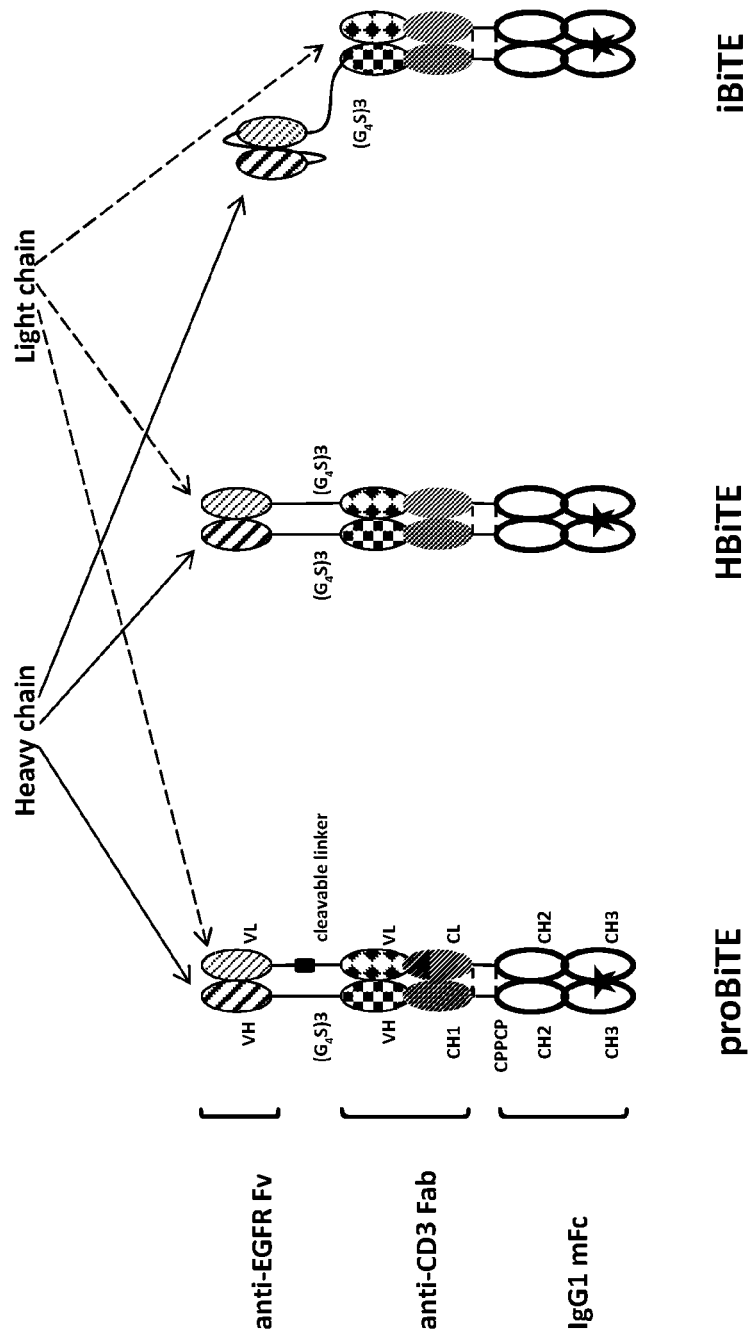
FIG. 3 shows schematic representation of bispecific antibodies of the present invention that can bind to EGFR and CD3. The antibody polypeptide chain containing anti-CD3 VH-CH1 sequence is designated heavy chain and the one with anti-CD3 VL-CL sequence is designated light chain, regardless of their molecular weights. Stars denote mutations which decrease or abrogate Fc homodimerization. proBiTE: protease cleavable bispecific T cell engagers; HBiTE: H-shaped bispecific T cell engagers; iBiTE: I-shaped bispecific T cell engagers.

As a negative control, an H-shaped BiTE (HBiTE) was generated, in which the cleavable linker was replaced with the non-cleavable (G45)3 linker (see FIG. 3). For positive control, an i-shaped BiTE (iBiTE) was designed where the scFv of anti-EGFR antibody was fused via the (G45)3 linker to the N terminus of the VH-CH1 of anti-CD3 antibody (FIG. 3). In this configuration, binding to CD3 is not sterically restricted by the linker.

Figure 4:
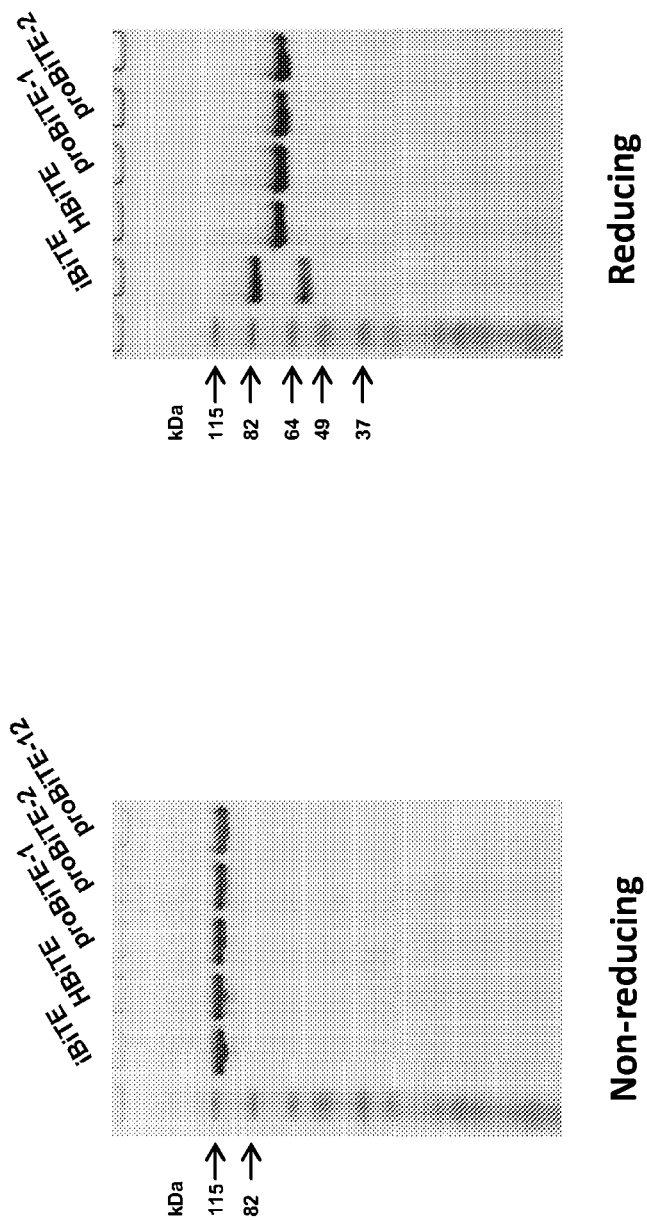
FIG. 4 shows expression and purification of bispecific antibody EGFR×CD3 proBiTE. Molecular masses of standards are shown on the left.
Figure 5:
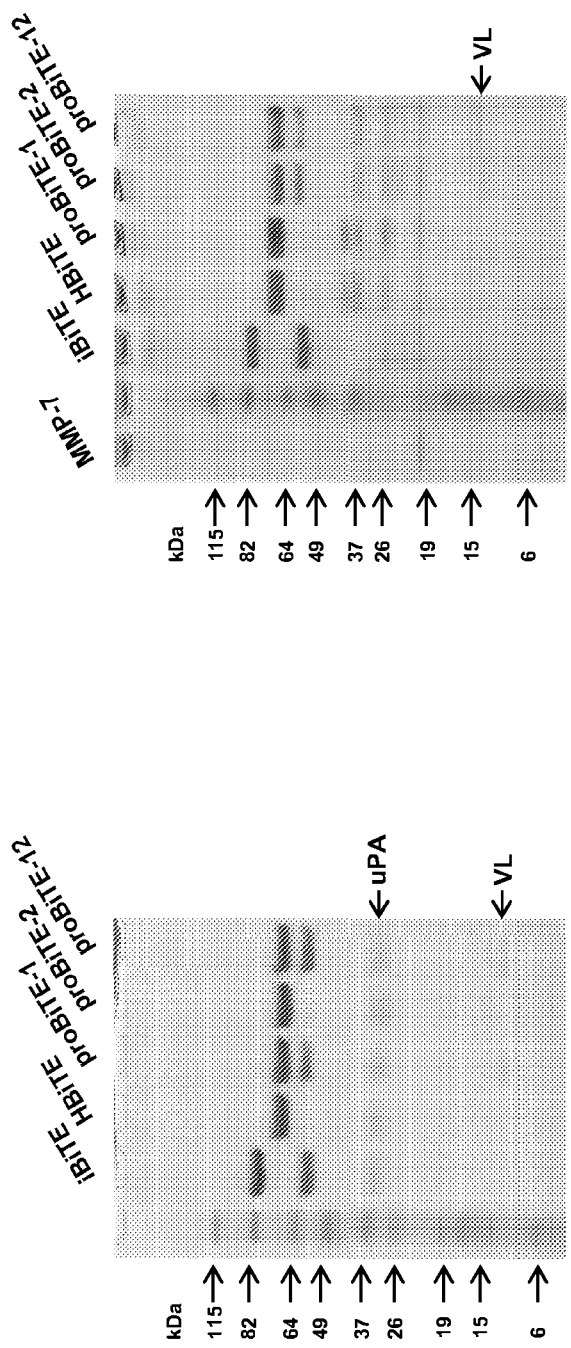
FIG. 5 shows cleavage of proBiTE with tumor-associated proteases. Molecular masses of standards are shown on the left. uPA and the isolated VL domain of anti-EGFR antibody are indicated by arrows on the right.
Figure 6:
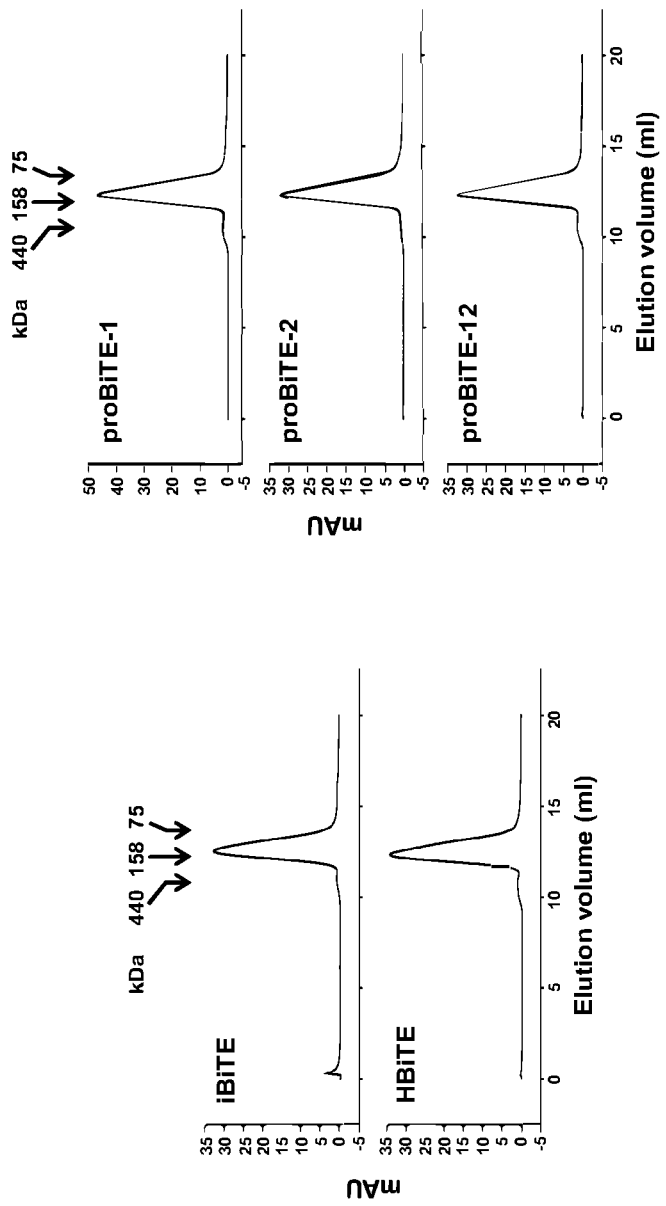
FIG. 6 shows size-exclusion chromatography of proBiTE. The arrows at the top indicate the elution volumes of the molecular mass standards in PBS (pH7.4): ferritin (440 kDa), aldolase (158 kDa) and conalbumin (75 kDa).

All the bispecific antibodies were well expressed in transiently transfected 293 free style (293FS) cells and secreted into the culture supernatants. On a non-reducing SDS-PAGE, a vast majority of the purified antibodies migrated as a heterodimer with apparent molecular weight (aMW) of approximately 115 kDa (FIG. 4). On a reducing SDS-PAGE, the two polypeptide chains of iBiTE were well separated while those of other bispecific antibodies overlapped with each other with apparent molecular weight of approximately 70 kDa.

proBiTE-1 and proBiTE-12 were efficiently cleaved by uPA, resulting in an isolated VL domain of the anti-EGFR antibody while other bispecific antibodies were not sensitive to the protease (FIG. 5, left panel). Similarly, proBiTE-2 and proBiTE-12 were cleavable when incubated with MMP-7 while others did not appear to be specifically cleaved at the linker position (FIG. 5, right panel). Several unexpected products were observed on the reducing SDS-PAGE, suggesting there could be other cleavage sites for MMP-7 in the antibodies. Size-exclusion chromatography analysis showed that the vast majority of purified bispecific antibodies migrated as a monomer with aMW of approximately 120 kDa, similar to their calculated molecular weight (cMW) (FIG. 6).

Example 4

Binding Affinity of Bispecific Antibody for Cell Surface-Associated EGFR and CD3

Figure 7:
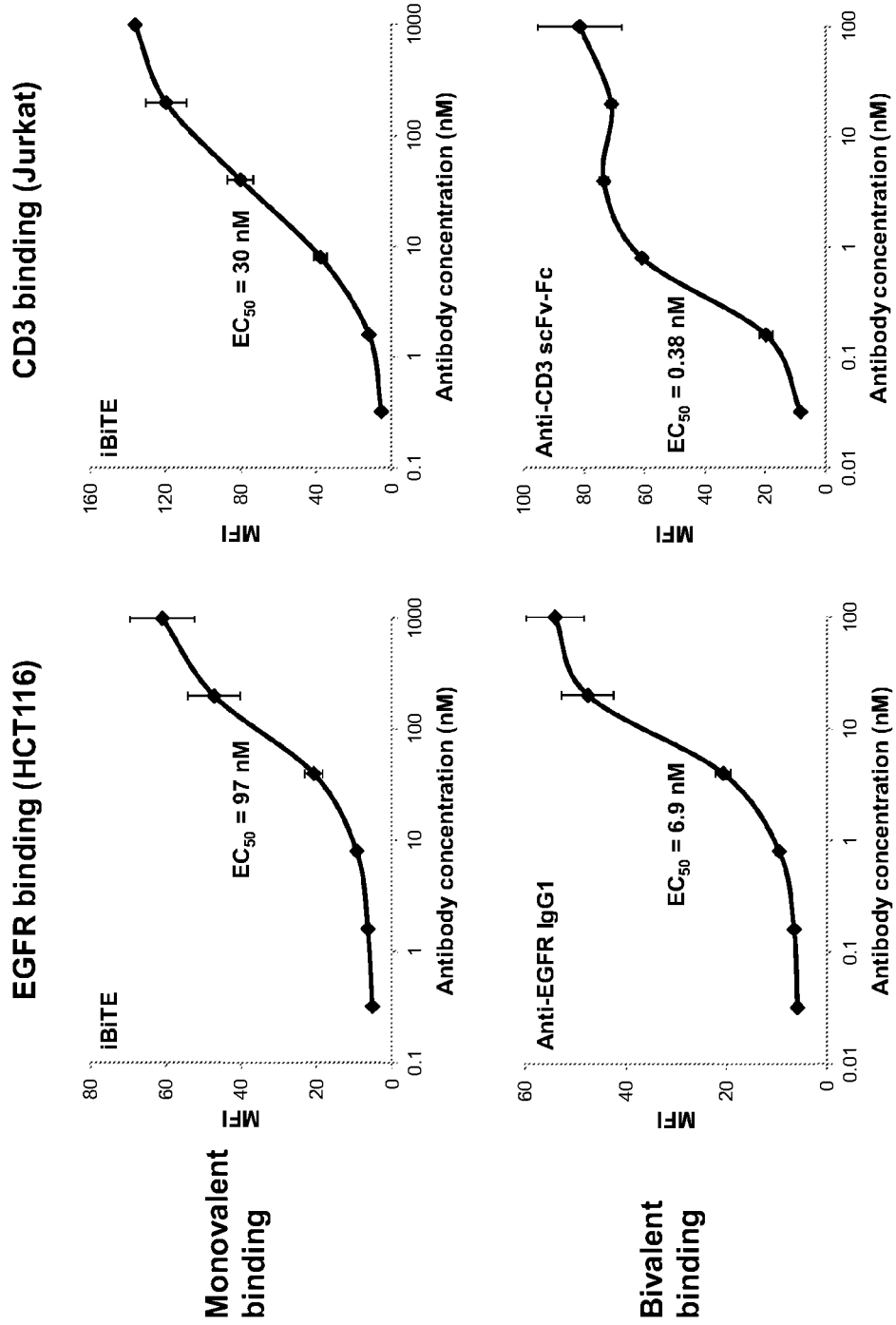
FIG. 7 shows binding affinity of bispecific antibodies for cell surface-associated EGFR and CD3 as measured by flow cytometry. WI, mean fluorescence intensity.

The monovalent and bivalent cell-binding affinities of the anti-EGFR and anti-CD3 antibodies were measured. The monovalent bispecific antibody iBiTE bound to an EGFR-expressing human colon cancer cell line HCT116 with $EC_{50}$ of 97 nM and to a CD3-expressing human T cell line Jurkat with $EC_{50}$ of 30 nM, suggesting moderate affinities of the EGFR and CD3 antibodies (FIG. 7). The bivalent monospecific antibodies, anti-EGFR IgG1 and anti-CD3 scFv-Fc, bound much more strongly to HCT116 and Jurkat cell lines with $EC_{50}$s of 6.9 and 0.38 nM, respectively, suggesting high avidity effect of bivalent binding.

Figure 8:
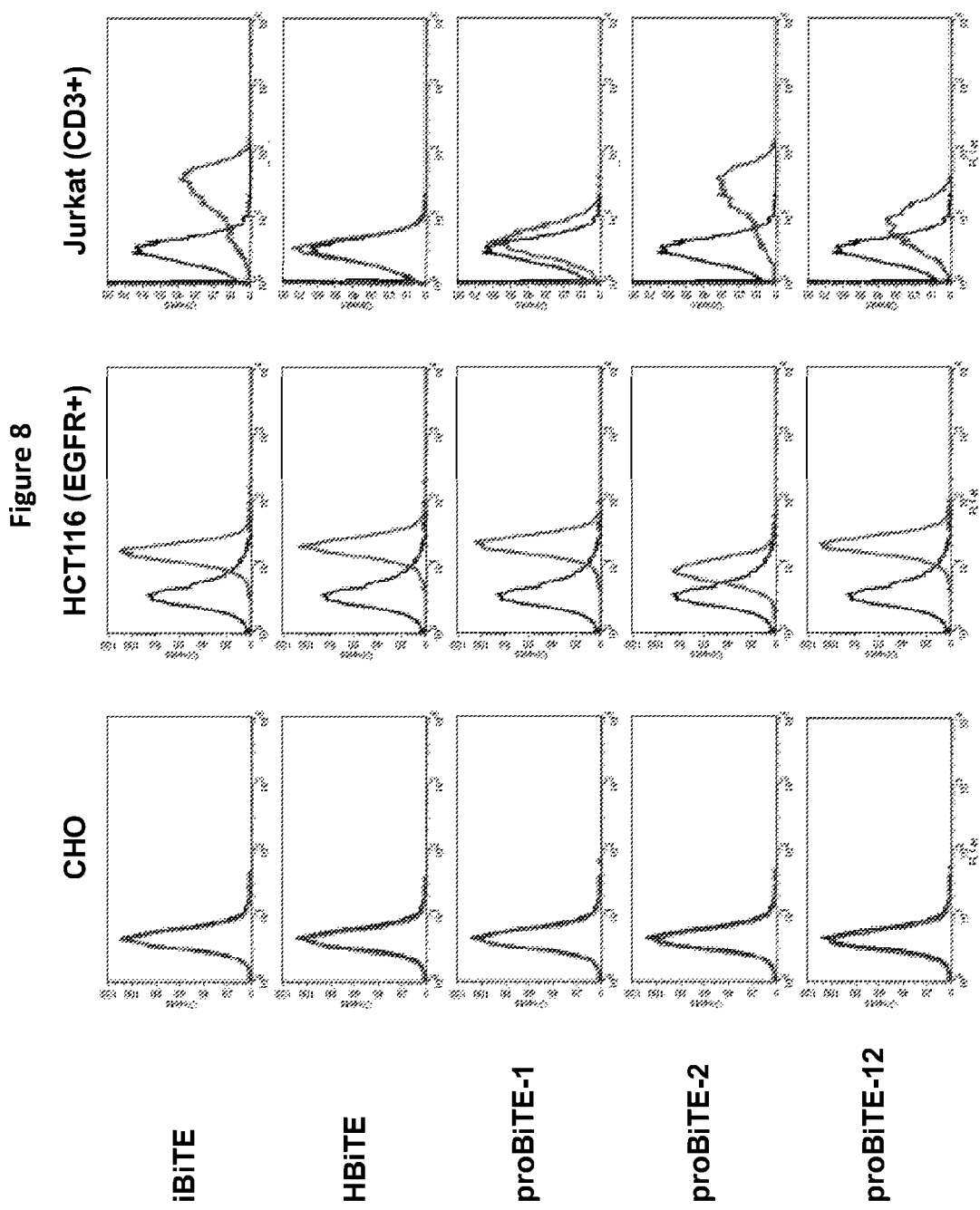
FIG. 8 shows binding of proBiTE to cell-surface EGFR and CD3 as measured by flow cytometry. The tracings on the left in each panel represent reference cells which were incubated with secondary antibody only (FITC-conjugated anti-human IgG (Fc-specific)). The tracings on the right in each panel represent experimental groups, in which the cells were first incubated with bispecific antibodies at a concentration of 2 μg/mL and then with the secondary antibody.

Next, the bindings of bispecific antibodies with different structures and composition of linkers to EGFR and CD3 were examined. At a concentration of 2 µg/mL, none of the bispecific antibodies interacted with CHO cells which do not express human EGFR and CD3, whereas iBiTE bound to both EGFR-expressing HCT116 and CD3-expressing Jurkat cells, suggesting specific binding activity of the anti-EGFR and anti-CD3 antibodies (FIG. 8). In contrast, HBiTE bound to HCT116 cells as well as iBiTE while no binding to Jurkat cells was observed, suggesting that binding activity of the anti-CD3 antibody was completely abrogated at the concentration tested. The three proBiTE variants exhibited various binding activities with both cell lines, probably due to different flexibility and orientations of the cleavable linkers.

Figure 9:
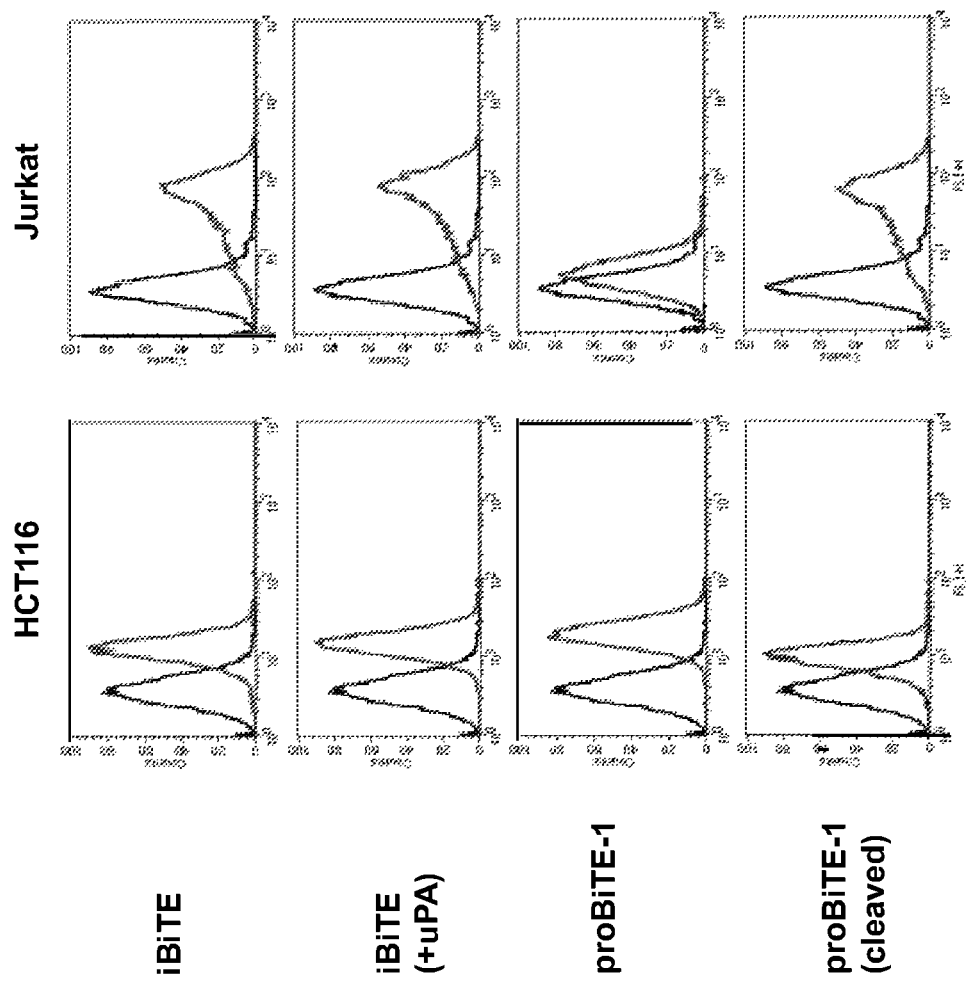
FIG. 9 shows binding of pre-cleaved proBiTE to cell-surface EGFR and CD3 as measured by flow cytometry. The tracings on the left in each panel represent reference cells which were incubated with secondary antibody only (FITC-conjugated anti-human IgG (Fc-specific)). The tracings on the right in each panel represent experimental groups, in which the cells were first incubated with bispecific antibodies at a concentration of 2 μg/mL and then with the secondary antibody.
Figure 10:
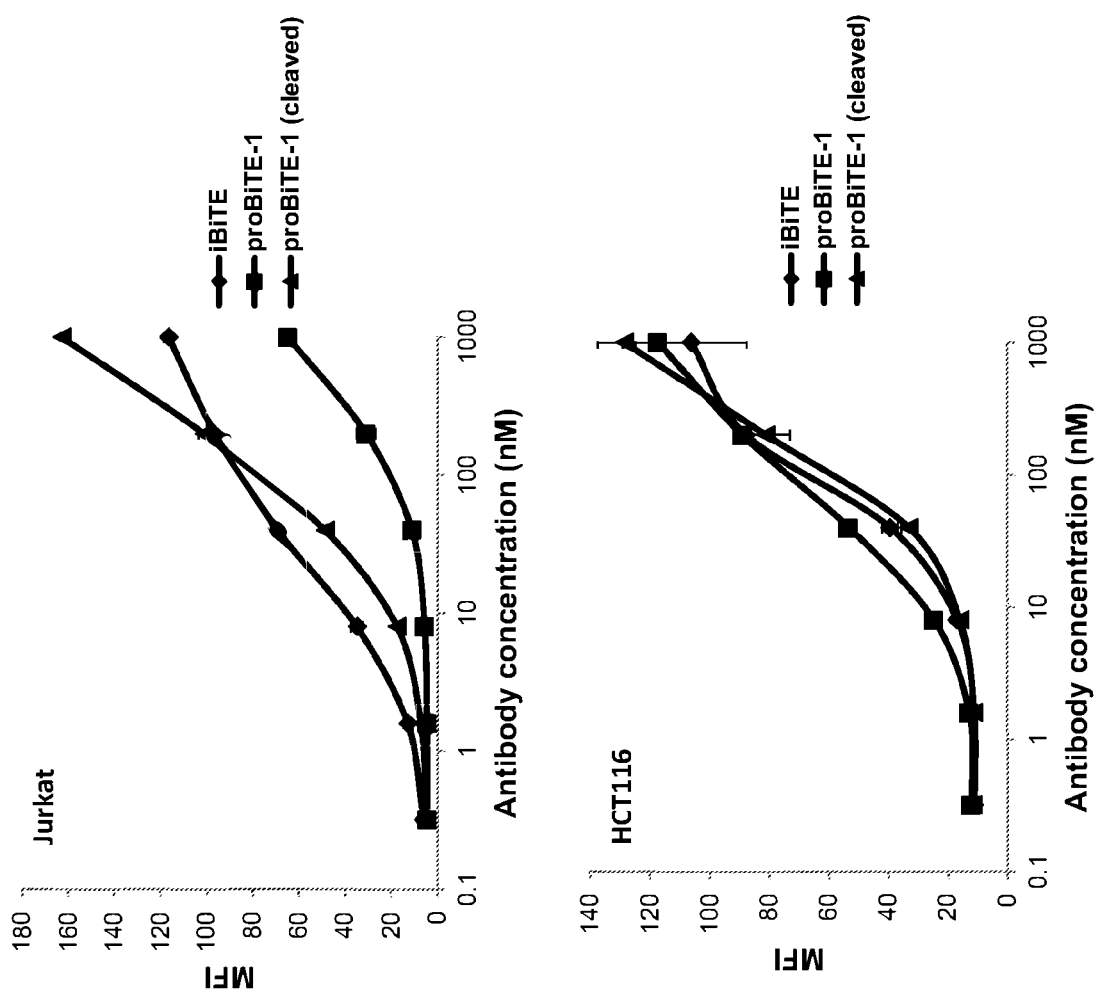
FIG. 10 shows binding of intact and cleaved proBiTE-1 to cell surface EGFR and CD3 as measured by flow cytometry.

The bindings of pre-cleaved proBiTE-1 to EGFR and CD3 were then examined. The results showed that the binding of iBiTE, which has fully open antigen binding sites, to HCT116 and Jurkat cells was not affected by uPA. proBiTE-1 pre-cleaved by uPA exhibited decreased binding to EGFR-expressing HCT116 cells while restored binding activity with CD3-expressing Jurkat cells compared to iBiTE at an antibody concentration of 2 µg/mL (FIG. 9). When different antibody concentrations were tested, proBiTE-1 bound to EGFR-expressing HCT116 cells slightly better than iBiTE at concentrations lower than 200 nM (FIG. 10). After cleavage by uPA, binding of proBiTE-1 to HCT116 cells was decreased by approximately two-fold and was similar to that of iBiTE. In contrast, proBiTE-1 bound to CD3-expressing Jurkat cells about 30-fold more weakly than iBiTE. Protease cleavage restored the binding activity of proBiTE-1 with Jurkat cells.

Figure 11:
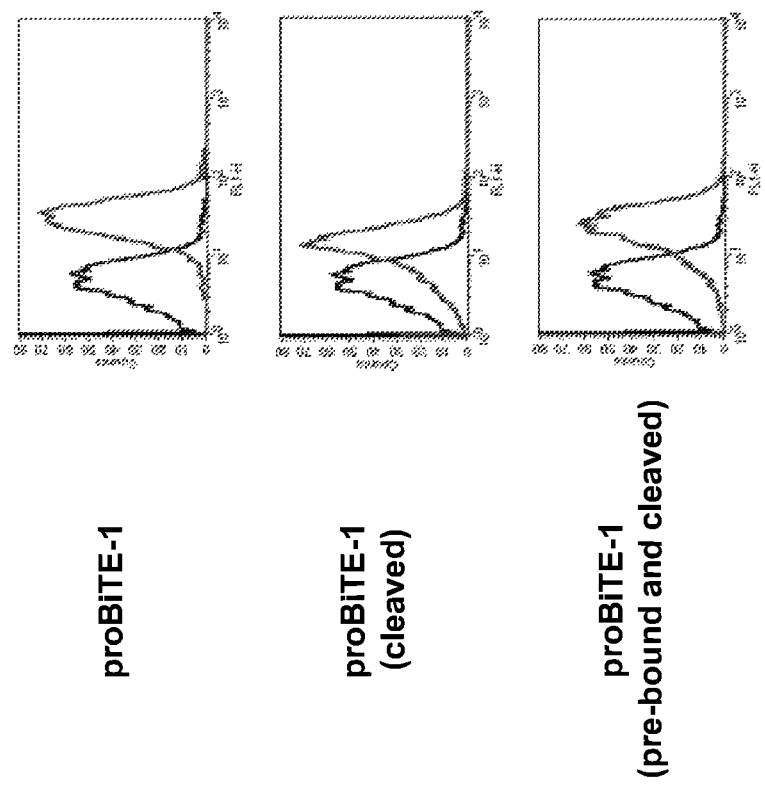
FIG. 11 shows binding of pre-bound and then cleaved proBiTE-1 to cell-surface EGFR as measured by flow cytometry. The tracings on the left in each panel represent reference cells which were incubated with secondary antibody, FITC-conjugated anti-human IgG (Fc-specific), only. The tracings on the right in each panel represent experimental groups, in which the cells were first incubated with intact or pre-cleaved bispecific antibodies at a concentration of 2 µg/mL and then with the secondary antibody in the absence or presence of uPA.

Whether the VH and VL domains of the EGFR antibody in proBiTE-1 pre-bound to cells could be stabilized was tested. As expected, pre-cleaved proBiTE-1 had decreased binding to HCT116 cells compared to the intact proBiTE-1 while proBiTE-1 pre-bound to the cells and then cleaved by uPA restored binding activity at a concentration of 2 µg/mL (FIG. 11). These results are in agreement with the hypothesis that employing naturally unstable VH-VL domains as the tumor antigen binding antibody could further decrease on-target toxicity of this class of bispecific antibodies.

Example 5

Bispecific Antibody-Mediated T Cell Activation

Figure 12:
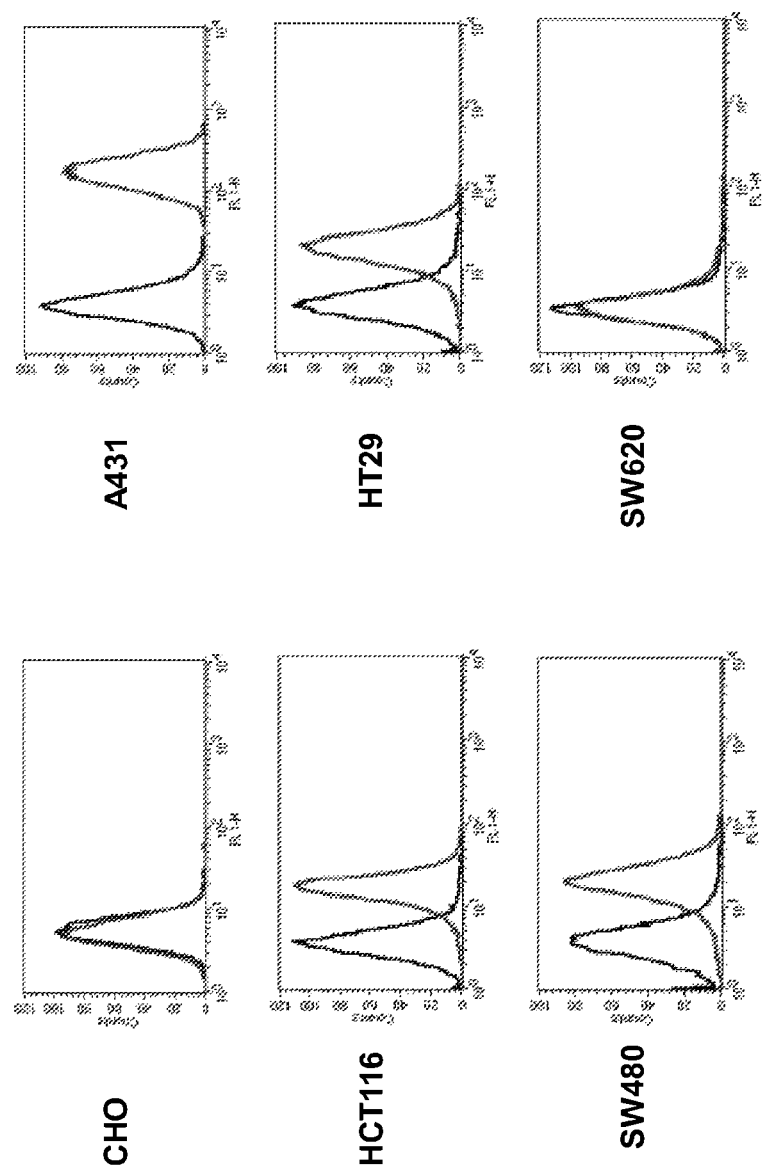
FIG. 12 shows characterization of several human colon cancer cell lines for EGFR expression on cell surface by flow cytometry.

The ability and specificity of proBiTE to activate human T cells in the presence of EGFR-expressing cells were evaluated by using Promega T cell activation bioassay systems. Of the 6 target cell line tested, CHO cells do not express human EGFR while A431 cells has a high level of EGFR expression and has been frequently used as a model human cell line for drug discovery (FIG. 12). The three human colon cell lines, HCT116, HT29 and SW480, express a similar level of EGFR while EGFR expression was not detectable on SW620 cells at an antibody concentration of 2 µg/mL.

Figure 13:
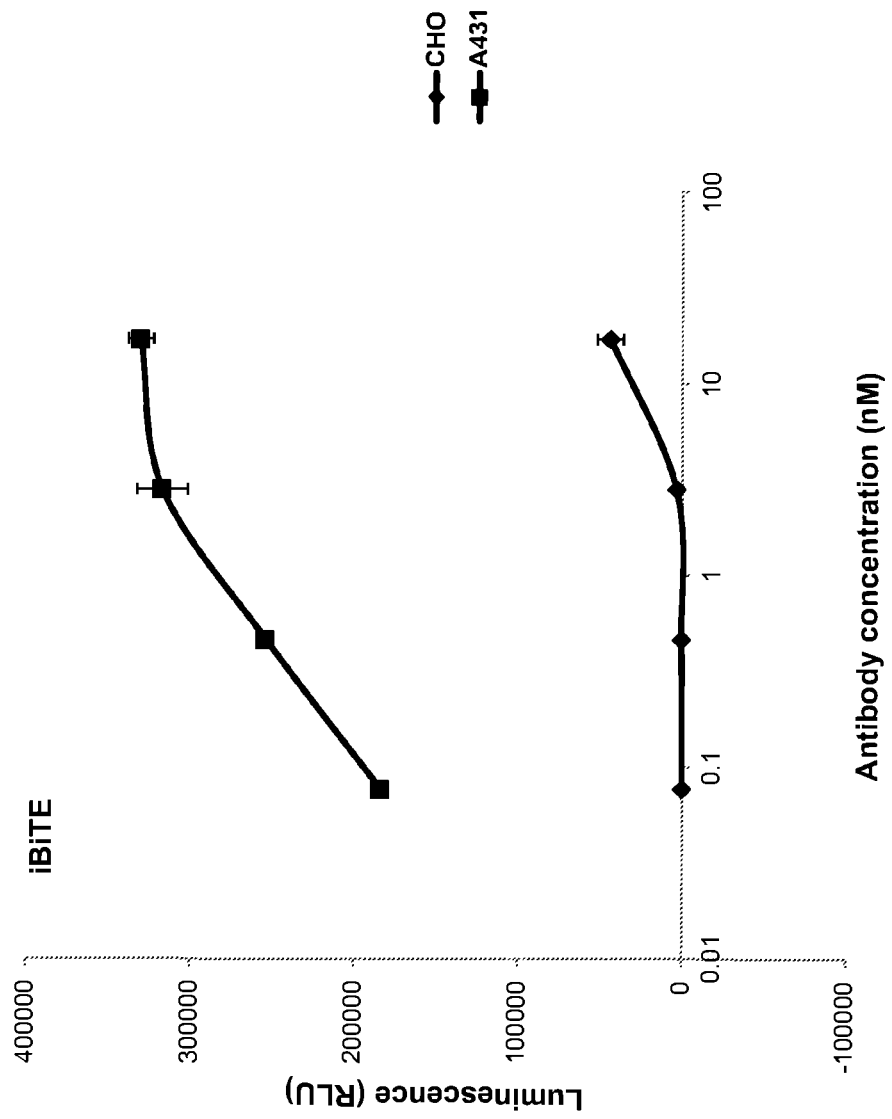
FIG. 13 shows T cell activation by iBiTE. The ability and specificity of iBiTE to activate human T cells in the presence of EGFR-expressing cells were evaluated by Promega T cell activation bioassay systems according to the manufacturer's instructions.
Figure 14:
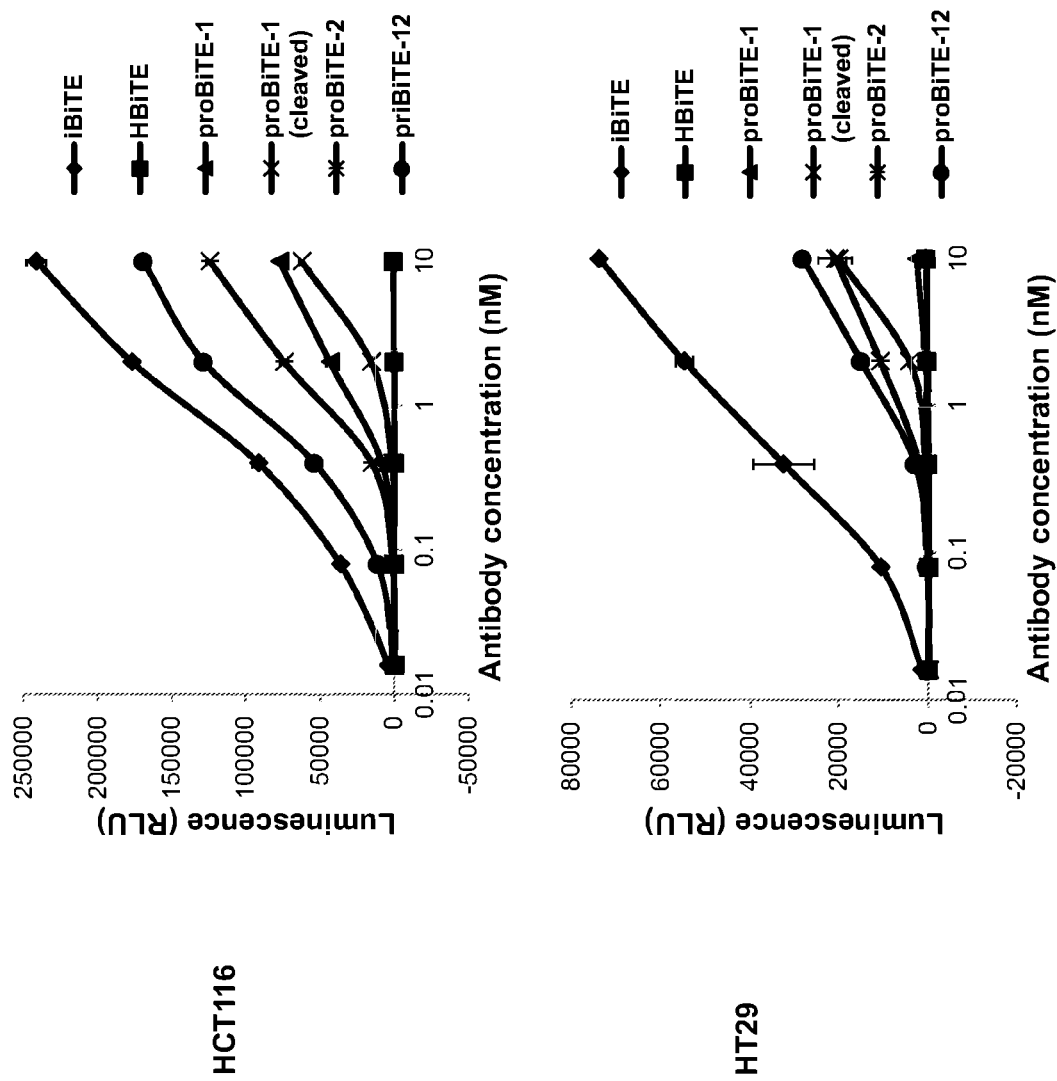
FIG. 14 shows short-term activation of T cells by proBiTE. The ability of proBiTE to activate human T cells during a short period (5 h) of incubation with EGFR-expressing human colon cancer cells were evaluated by Promega T cell activation bioassay systems according to the manufacturer's instructions.

In the presence of EGFR-positive A431 cells, human T cells were efficiently activated by iBiTE with $EC_{50}$ of approximately 80 pM (FIG. 13). With EGFR-negative CHO cells, however, human T cells were not or only marginally activated at high concentrations, suggesting high specificity of the bispecific antibody. In the presence of HCT116 cells, iBiTE efficiently activated human T cells whereas HBiTE did not have an effect on the T cells likely due to blockade of CD3 binding (FIG. 14). proBiTE-1 gave a low level of T cell activation. Surprisingly, protease cleaved proBiTE-1 was less efficient in T cell activation than intact proBiTE-1 likely because of deteriorated interaction between the VH and VL domains of the EGFR-binding antibody in cleaved proBiTE-1. Results with proBiTE-2 and proBiTE-12, for which CD3 binding was not or only partially blocked, showed better T cell activation activity than proBiTE-1. Similar results were observed with HT29 cells except that proBiTE-1 failed to activate the T cells while apparent activation was seen with cleaved proBiTE-1. This is in contrast to the result from HCT116 cells, suggesting that HCT116 cells might express a higher level of proteases than HT29 cells.

Example 6

Bispecific Antibody-Mediated Killing of Human Colon Cancer Cell Lines

Figure 15:
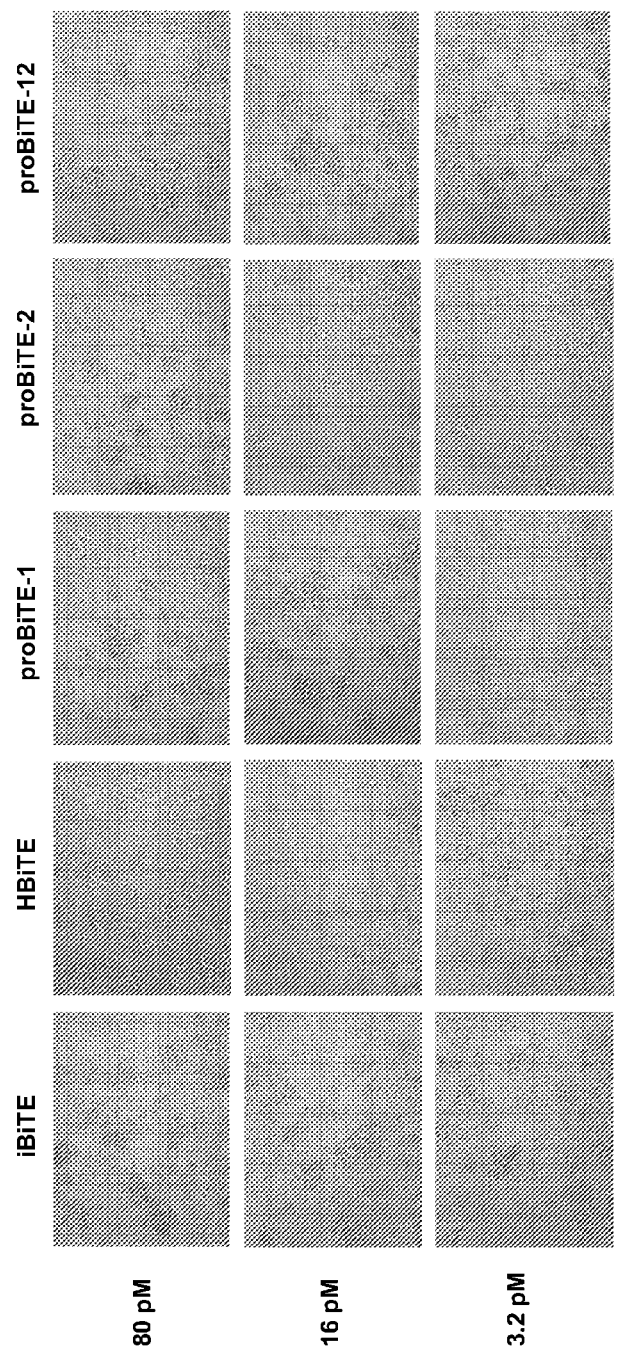
FIG. 15 shows killing of HCT116 cells by the bispecific antibodies in the presence of human PBMC. Target cells (HCT116) and effector cells (PBMC) are at a ratio of 1:5. Representative images were taken after 72 h of incubation.
Figure 16:
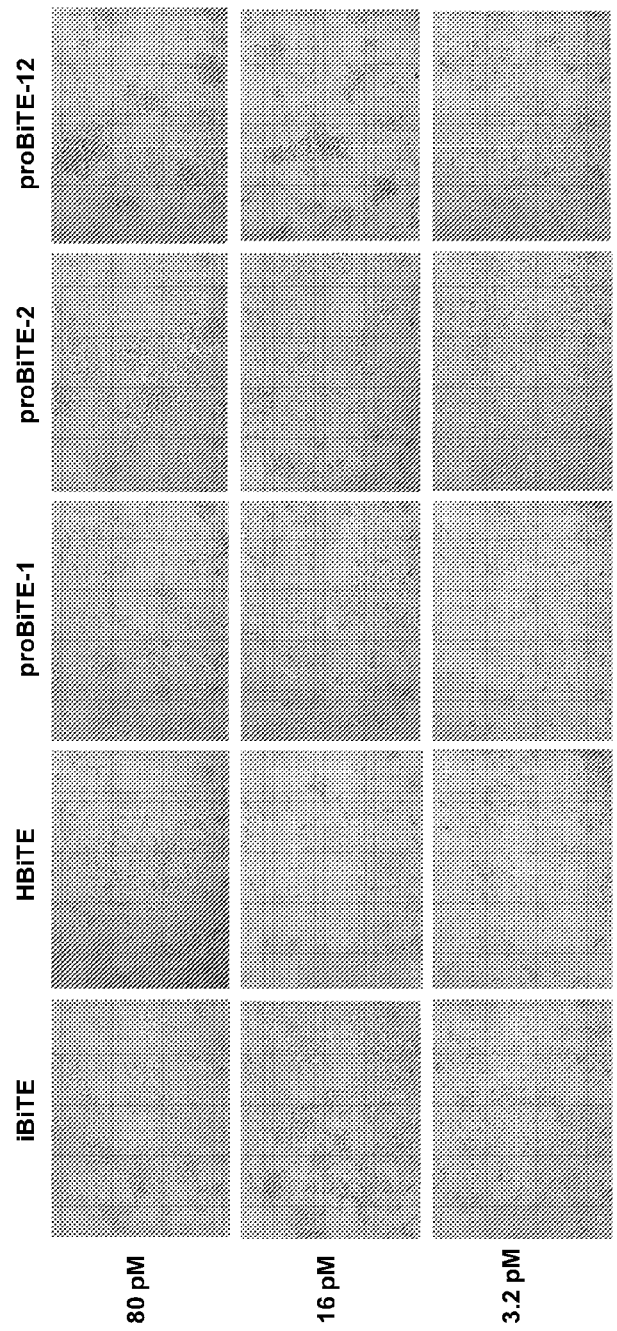
FIG. 16 shows killing of HT29 cells by the bispecific antibodies in the presence of human PBMC. Target cells (HT29) and effector cells (PBMC) are at a ratio of 1:5. Representative images were taken after 72 h of incubation.

HCT116 and HT29 cells are adherent and fibroblastic, and grow in a monolayer in RPMI 1640 medium while PBMC cells are round-shaped and grow in suspension. Engagement with the cancer cells caused aggregation and activation of T cells, eventually leading to killing of the cancer cells. Under a microscope, iBiTE and proBiTE-12 appeared to completely kill HCT116 cells at a concentration of as low as 3.2 pM (FIG. 15). HBiTE was much less potent exhibiting apparent killing only at high concentrations. The killing efficiency of proBiTE-1 and proBiTE-2 was comparable and was about 5-fold lower than that of iBiTE and proBiTE-12. Similar results were obtained with HT29 cells (FIG. 16).

Figure 17:
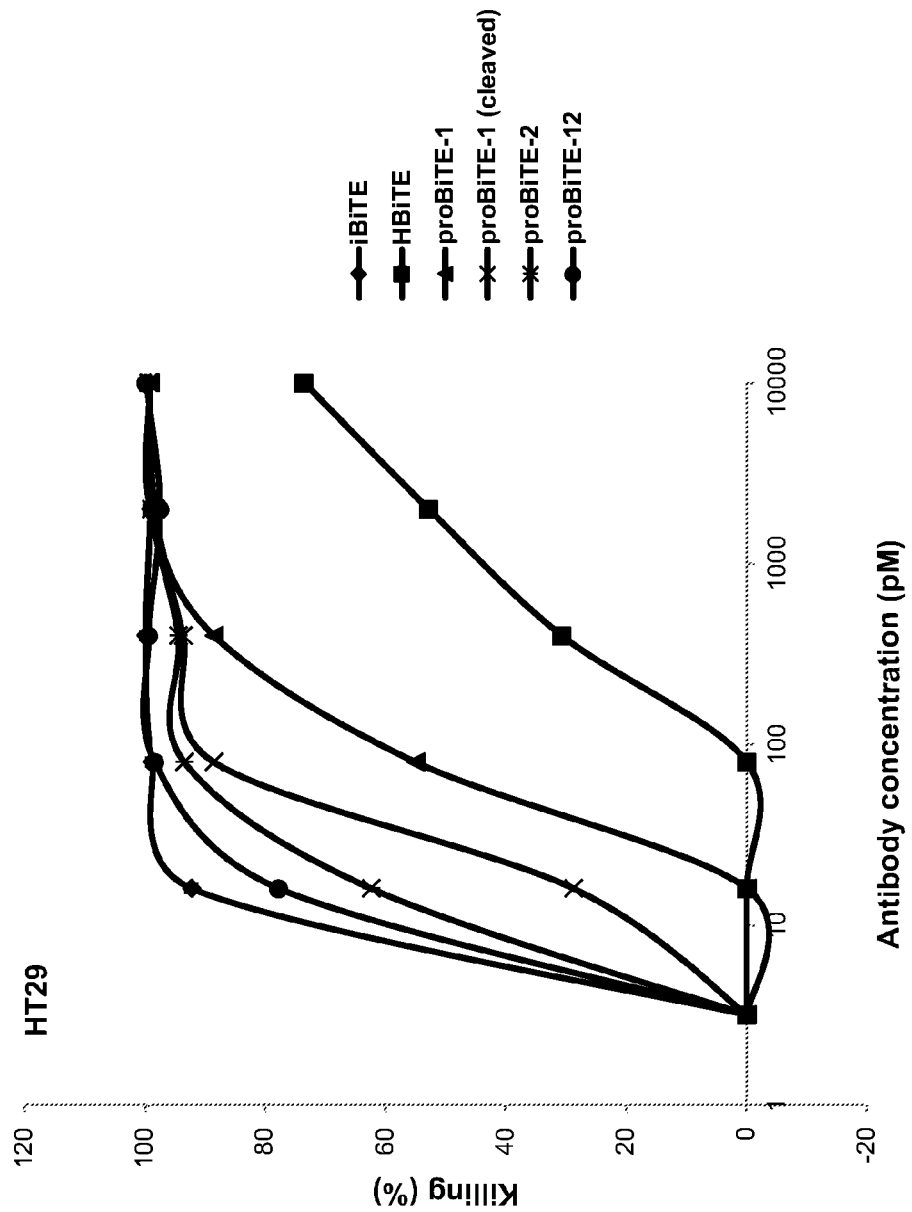
FIG. 17 shows killing of HT29 cells stably transfected with red firefly luciferase by the bispecific antibodies in the presence of human PBMC. Target cells (HT29) and effector cells (PBMC) are at a ratio of 1:5. Luciferase activity was measured after 72 h of incubation.

To quantify cell killing efficiency, HT29 cells stably transfected with red firefly luciferase gene were used as target cells. The results showed that iBiTE and proBiTE-12 exhibited comparably potent killing efficacy with $EC_{50}$ of approximately 6 pM (FIG. 17). HBiTE was able to kill the cancer cells at high concentrations but was about 300-fold less potent ($EC_{50}$, 2000 pM) than iBiTE. With a protease cleavage site in the linker, proBiTE-1 gave an $EC_{50}$ of about 90 pM, 15-fold higher than that of iBiTE likely due to inefficient cleavage and degradation of the former during the long period of incubation. The pre-cleaved proBiTE-1 was more potent than the intact proBiTE-1 but was still several-fold less potent than iBiTE, likely due to deteriorated interaction between the VH and VL domains of the EGFR-binding antibody in pre-cleaved proBiTE-1. None of the bispecific antibodies significantly inhibited the proliferation of SW620 cells at the concentrations tested, suggesting EGFR expression-dependent killing of HT29 cells (data not shown).

Example 7

Binding of Bispecific Antibody to Recombinant Human FcγRs

Figure 18:
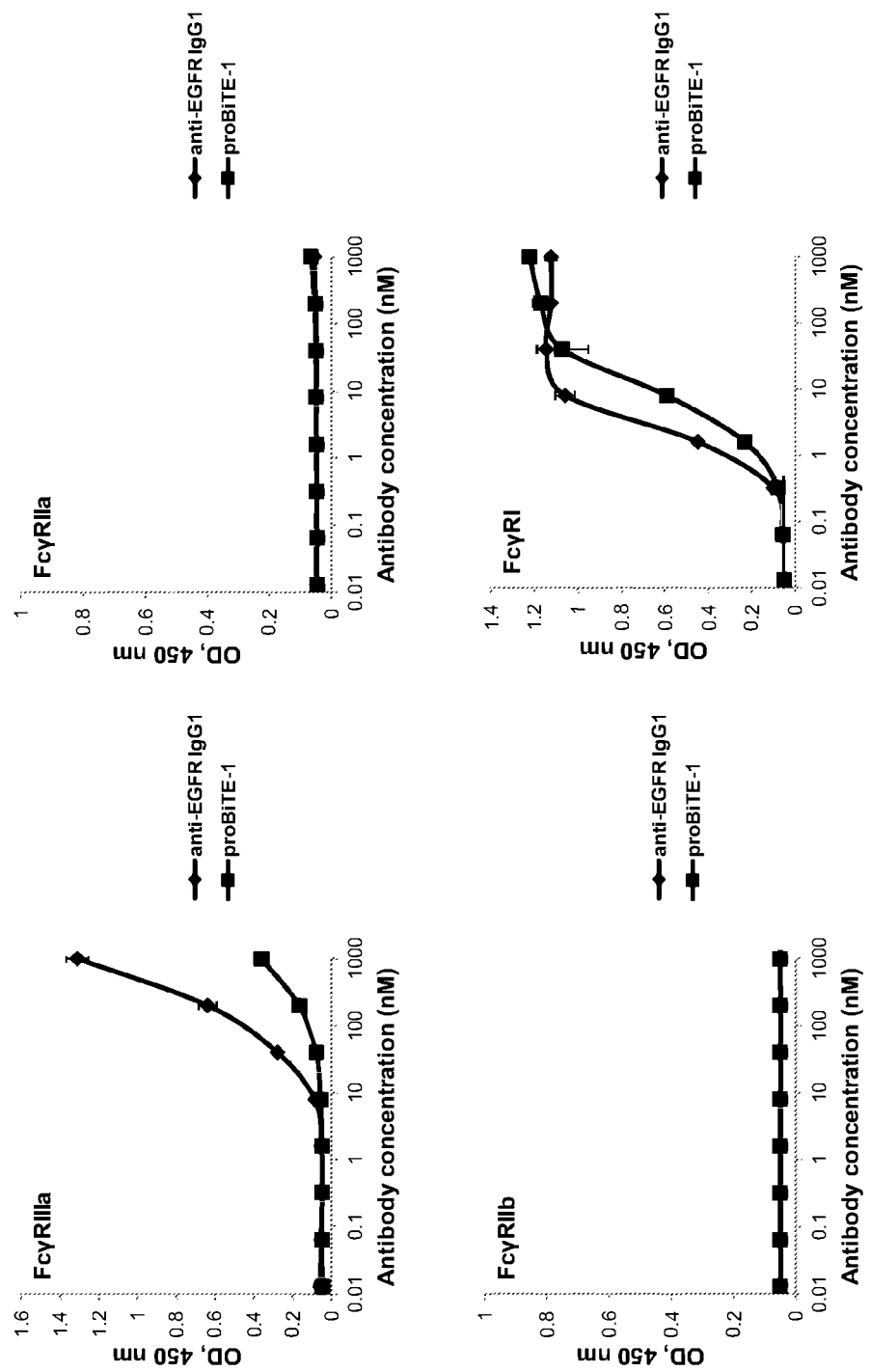
FIG. 18 shows ELISA binding of proBiTE-1 to recombinant human Fc gamma receptors (FcγR).

BiTE containing Fc could cause unwanted cytotoxicity of FcR-expressing cells. Because the hinge region of human IgG1 is directly or indirectly involved in Fc binding to FcγRs, it is hypothesized that the use of a shortened hinge sequence as the linker between the anti-CD3 Fab and mFc could lead to decreased FcγR binding due to steric hindrance and/or other mechanisms. To evaluate such a possibility with proBiTE, part (CPPCP (SEQ ID NO:154)) of the human IgG1 hinge sequence (DKTHTCPPCP) (SEQ ID NO:64) was used as the linker (see FIG. 3) and the resulting proBiTE-1 was compared with anti-EGFR IgG1 for binding to different FcγRs. The former showed decreased interactions with FcγRIIIa (by 10-fold) and FcγRI (by 3-fold) (FIG. 18). Neither anti-EGFR IgG1 nor proBiTE-1 bound to FcγRIIa and FcγRIIb as measured by ELISA. These results indicate that proBiTE could be less toxic against FcγRIIIa- and FcγRI-expressing cells than those BiTEs which use conventional IgG1 Fc and full-length hinge sequence.

Example 8

Inhibition of Tumor Growth in NOD/SCID Mice Engrafted with Human PBMC

Figure 19:
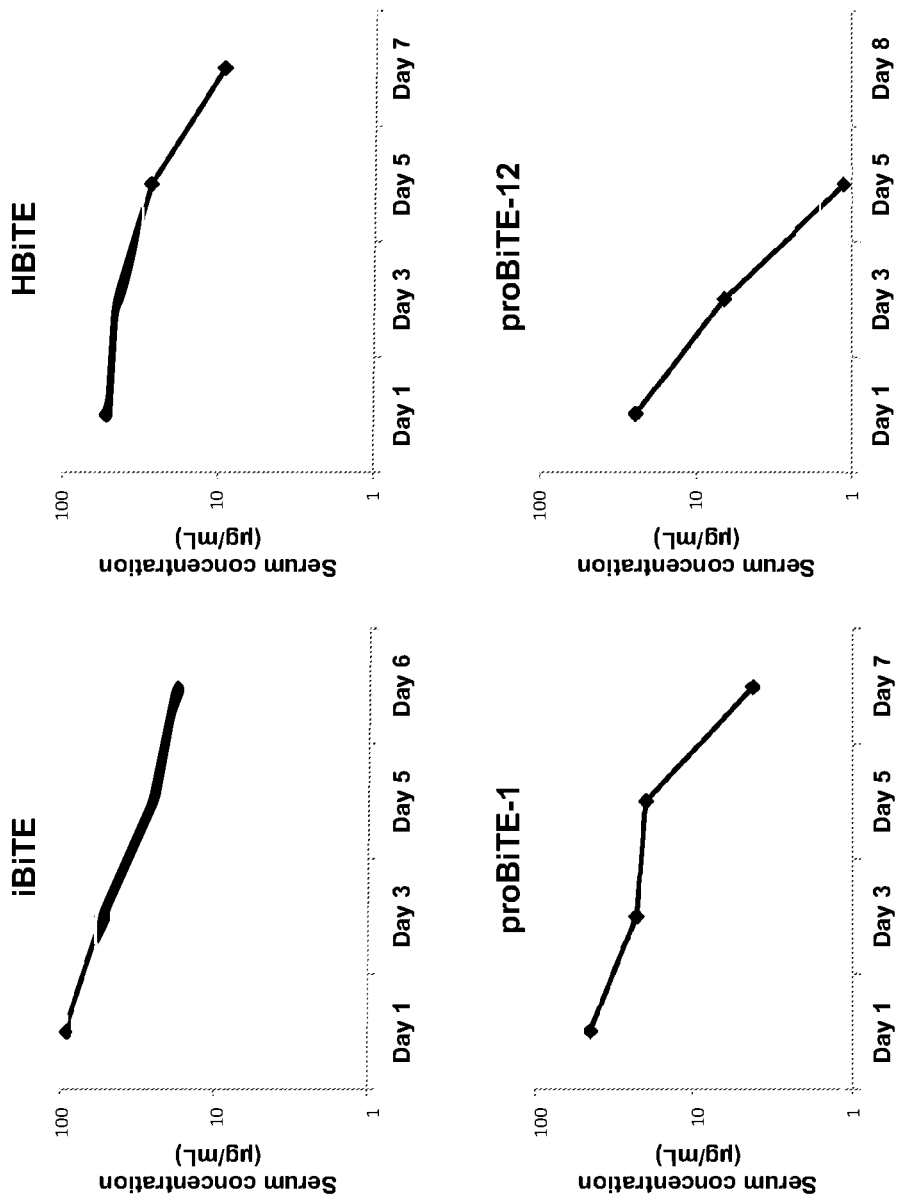
FIG. 19 shows pharmacokinetics of the bispecific antibodies in NOD/SCID mice.
Figure 20:
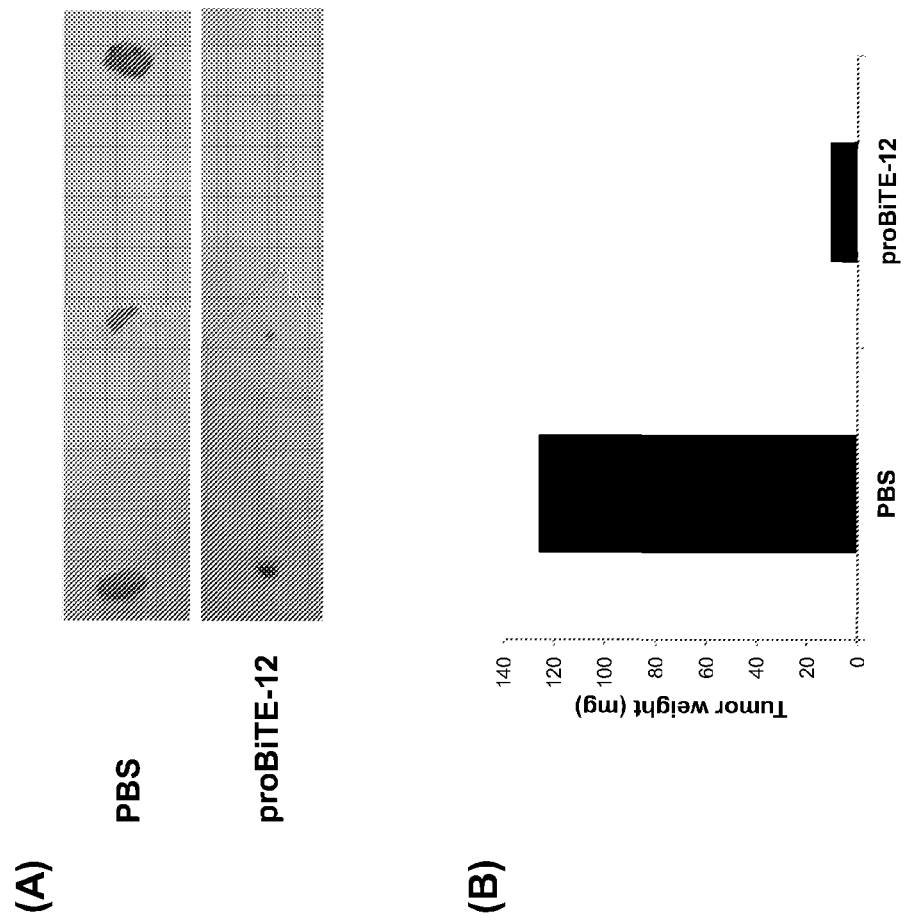
FIGS. 20A-B show anti-tumor activity of proBiTE-12 in NOD/SCID mice engrafted with human PBMC and colon cancer cell line HCT116.

To test how proBiTE could inhibit tumor growth in vivo, NOD/SCID mice engrafted with human PBMC were used as a model. Pharmacokinetics analysis showed that iBiTE and HBiTE had relatively higher serum concentrations than proBiTE-1 and proBiTE-12 at almost all time points with proBiTE-12 showing the fastest clearance (FIG. 19). The level of proBiTE-12, which has two different protease substrate sequences in the linker, declined at a higher rate than that of proBiTE-1 with only a single protease substrate sequence. These results suggest that introduction of protease cleavable linkers could decrease the stability of the bispecific antibodies in the circulation. In the tumor challenge experiments, proBiTE-12 potently inhibited the growth of HCT116 cells in the animals (FIG. 20).

Example 9

Generation and Characterization of Bispecific Antibody Variants with Altered Length and Composition of Cleavable Linkers To test whether alteration of the length and composition of the cleavable linker could affect the protease cleavage efficiency, cell killing activity and other properties of the bispecific antibodies, three proBiTE-1 variants were generated. proBiTE-1s contains a shortened cleavable polypeptide linker composed of the GSLSGRSDNHGGGS sequence (SEQ ID NO:61) (underlined is the substrate of uPA, matriptase and legumain). Substitution of the L residue in the substrate sequence of proBiTE-1s with the G residue led to the second variant, proBiTE-1s1 (linker sequence, GSGS-GRSDNHGGGS (SEQ ID NO:62)). The SG residues in the substrate sequence of proBiTE-1s can also be substituted by the GS residues, leading to the third variant, proBiTE-1s2 (linker sequence, GSGGSRSDNHGGGS (SEQ ID NO:63)).

Figure 21:
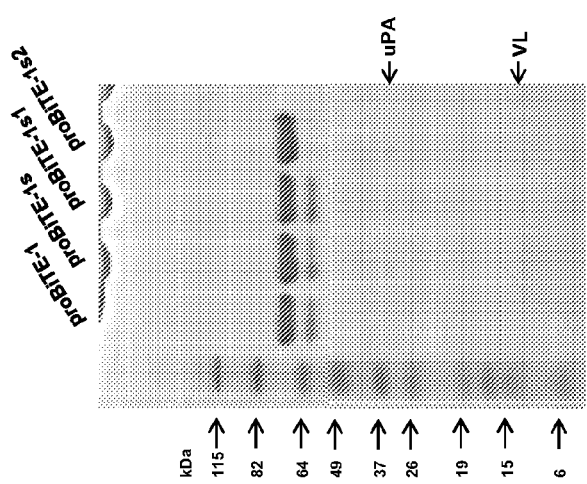
FIG. 21 shows cleavage of proBiTE-1 variants with uPA. Molecular masses of standards are shown on the left. uPA and the isolated VL domain of anti-EGFR antibody are indicated by arrows on the right.
Figure 22:
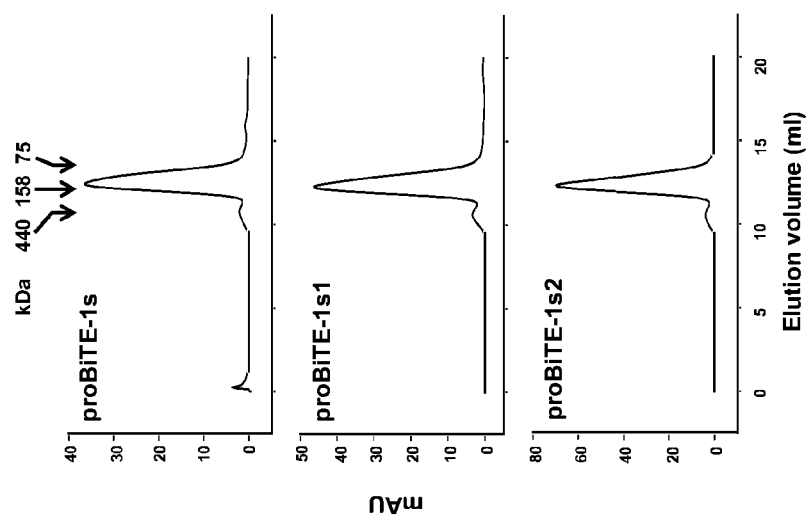
FIG. 22 shows size-exclusion chromatography of proBiTE-1 variants. The arrows at the top indicate the elution volumes of the molecular mass standards in PBS (pH7.4): ferritin (440 kDa), aldolase (158 kDa) and conalbumin (75 kDa).
Figure 23:
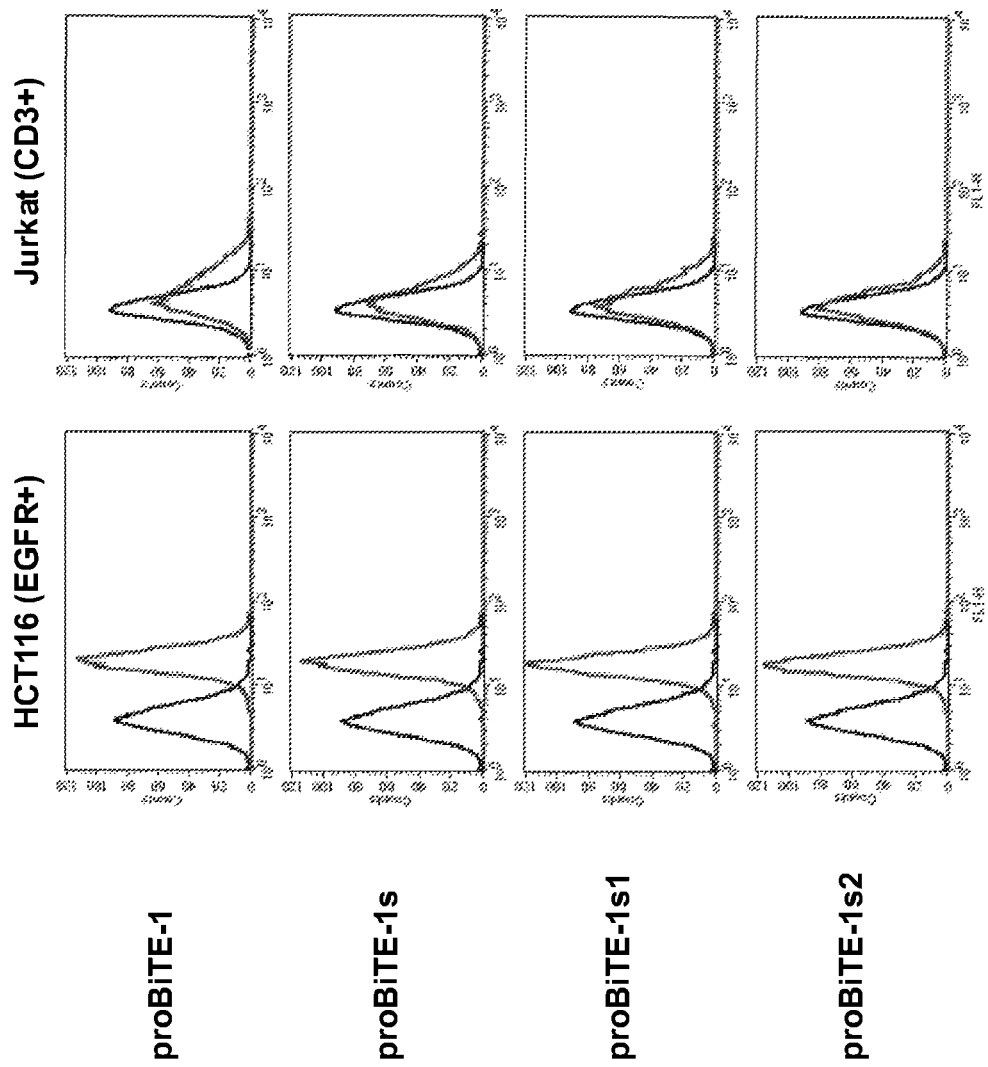
FIG. 23 shows binding of proBiTE-1 variants to cell-surface EGFR and CD3 as measured by flow cytometry. The tracings on the left in each panel represent reference cells which were incubated with secondary antibody, FITC-conjugated anti-human IgG (Fc-specific), only. The tracings on the right in each panel represent experimental groups, in which the cells were first incubated with bispecific antibodies at a concentration of 2 µg/mL and then with the secondary antibody.
Figure 24:
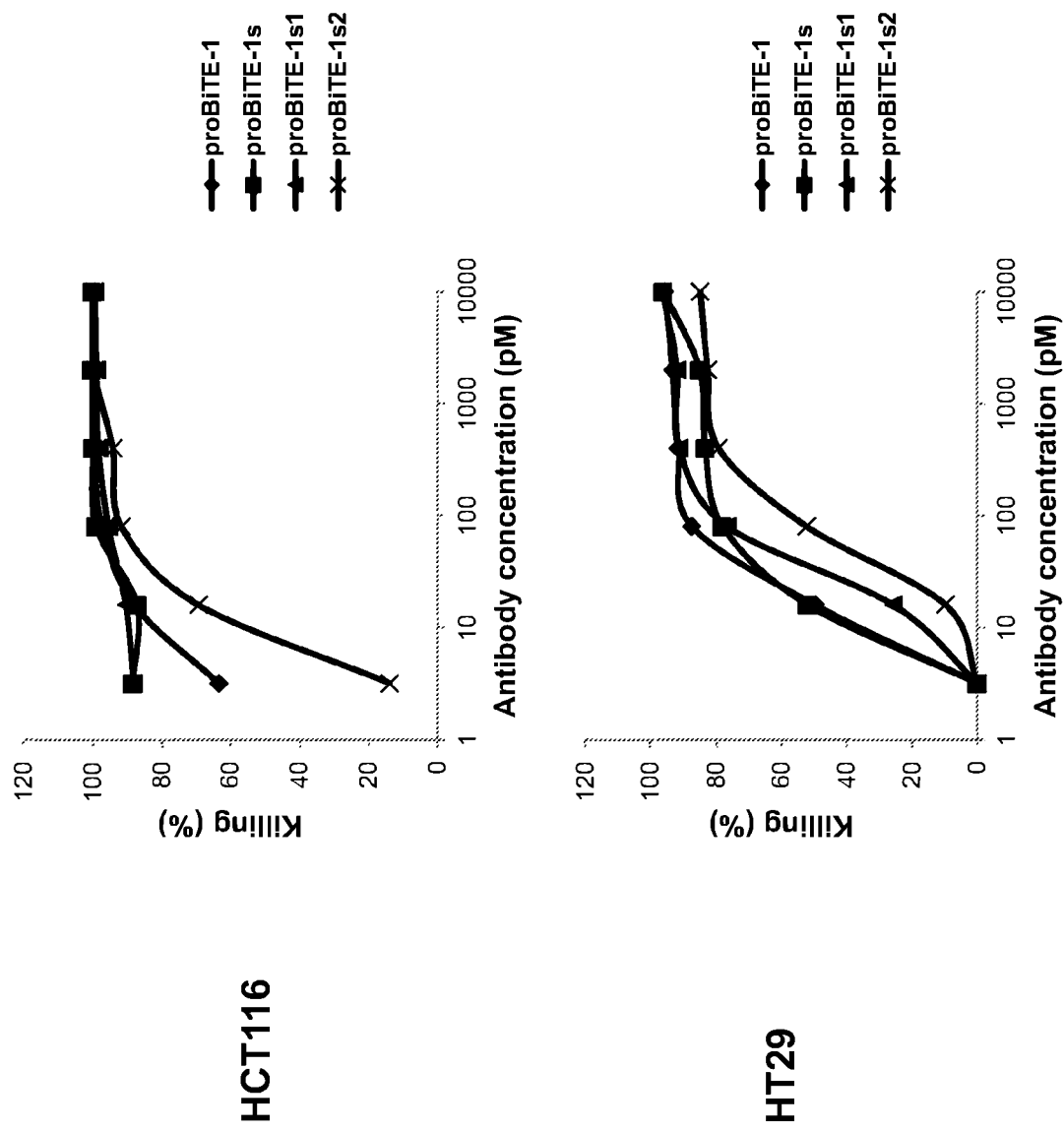
FIG. 24 shows killing of HCT116 and HT29 cells stably transfected with red firefly luciferase by proBiTE-1 variants in the presence of human PBMC. Target cells and effector cells (PBMC) are at a ratio of 1:5. Luciferase activity was measured after 72 h of incubation.

It was found that proBiTE-1s and proBiTE-1s1 were cleaved by uPA as efficiently as proBiTE-1 whereas proBiTE-1s2 was not sensitive to the protease (FIG. 21). These results suggest that the second and third, but not the first, amino acid residues of the substrate sequence were critical for protease sensitivity. Size-exclusion chromatography revealed that the vast majority of the above purified proBiTE-1 variants migrated as a monomer with aMW of approximately 120 kDa, similar to their calculated molecular weight (cMW) (FIG. 22). In flow cytometry analysis, all three proBiTE-1 variants showed slightly decreased binding activity with CD3-expressing Jurkat cells while their interactions with EGFR-expressing HCT116 were not affected (FIG. 23). These results suggest that the length but not the amino acid residue substitutions could have an impact on the flexibility and orientations of the cleavable linker.

proBiTE-1 and proBiTE-1s showed similar killing efficiency, suggesting that shortening the cleavable linker does not have an effect on antibody function (FIG. 24). proBiTE- 1s1 killed HCT116 as efficiently as proBiTE-1s but the former showed slightly decreased (by 2-fold) efficiency with HT29 cells. In both cases, the activity of proBiTE-1s2 was significantly reduced compared to other variants, suggesting that the SG residues in the substrate sequence are crucial to the sensitivity of proteases, in agreement with the results from uPA cleavage (FIG. 21).

Example 10

Rational Design of Bispecific Antibody with Sterically Restricted Access of Dual Antigen Binding Sites (dproBiTE)

Figure 25:
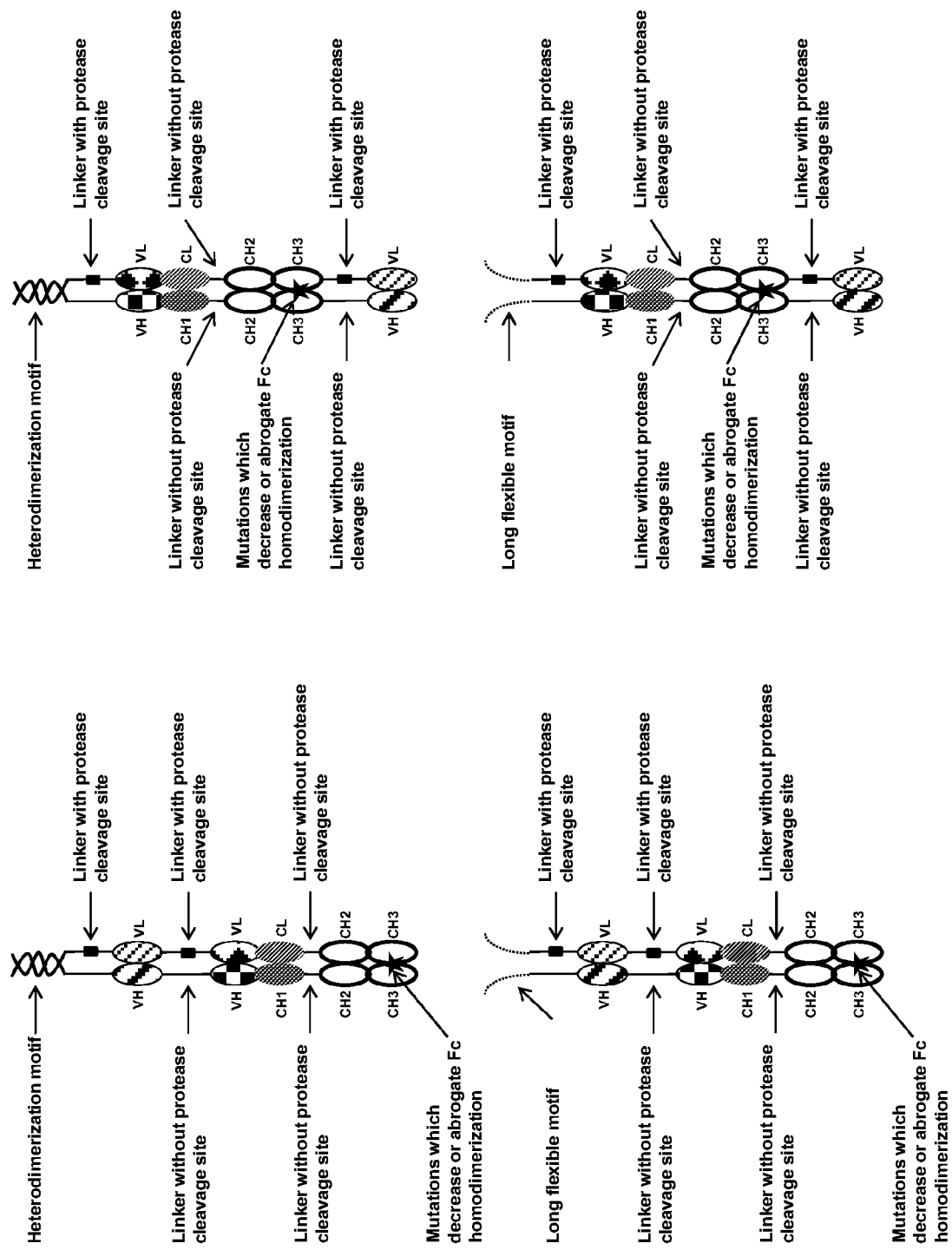
FIG. 25 shows schematic representation of examples of various embodiments of protease cleavable bispecific antibodies with sterically restricted access of dual antigen binding sites (dproBiTE).
Figure 26:
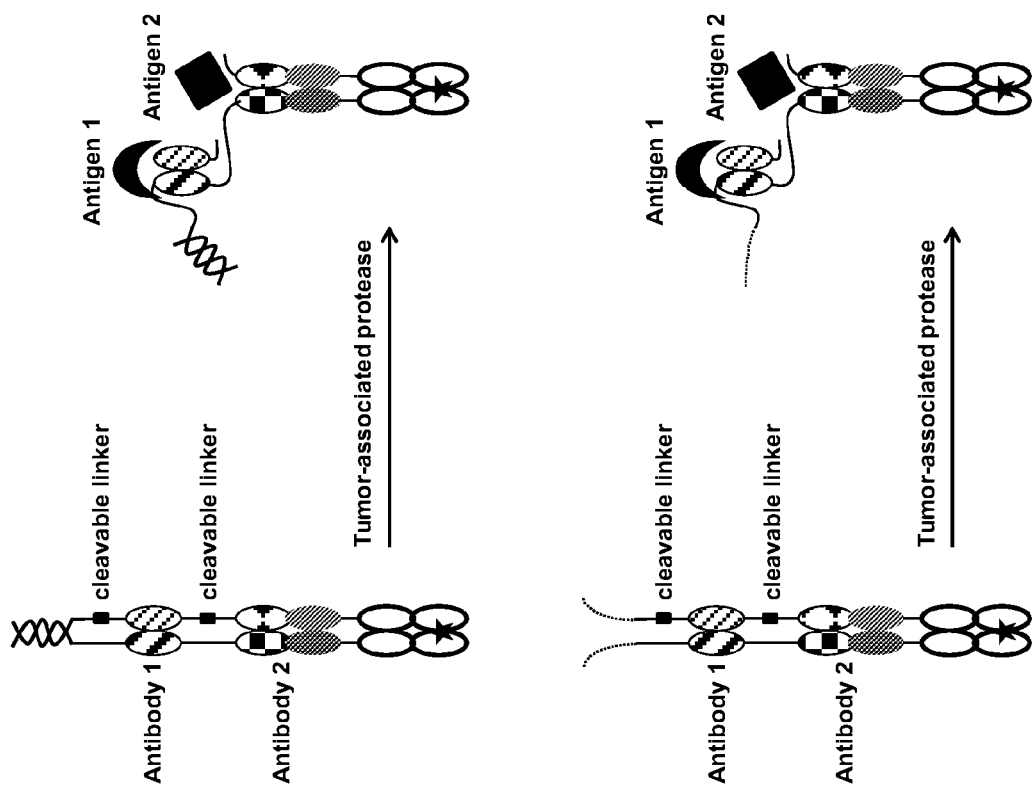
FIG. 26 shows mechanism of action of dproBiTE. All unlabeled modules have the same meanings as in FIGS. 25A-B.

Having demonstrated protease-dependent functionality of proBiTE, dproBiTE with sterically restricted access of dual antigen binding sites was designed and evaluated. It is hypothesized that addition of a long flexible motif, for example, naturally occurring short heterodimerization peptides, to the N terminus of the antigen binding site which is not guarded in proBiTE, could cause steric occlusion of the antigen binding site (FIG. 25). Protease cleavage of the cleavable linkers would reduce or eliminate the steric occlusion, leading to protease-dependent interaction with antigens (FIG. 26).

Example 11

Generation and Characterization of EGFR×CD3 dproBiTE

Figure 27:
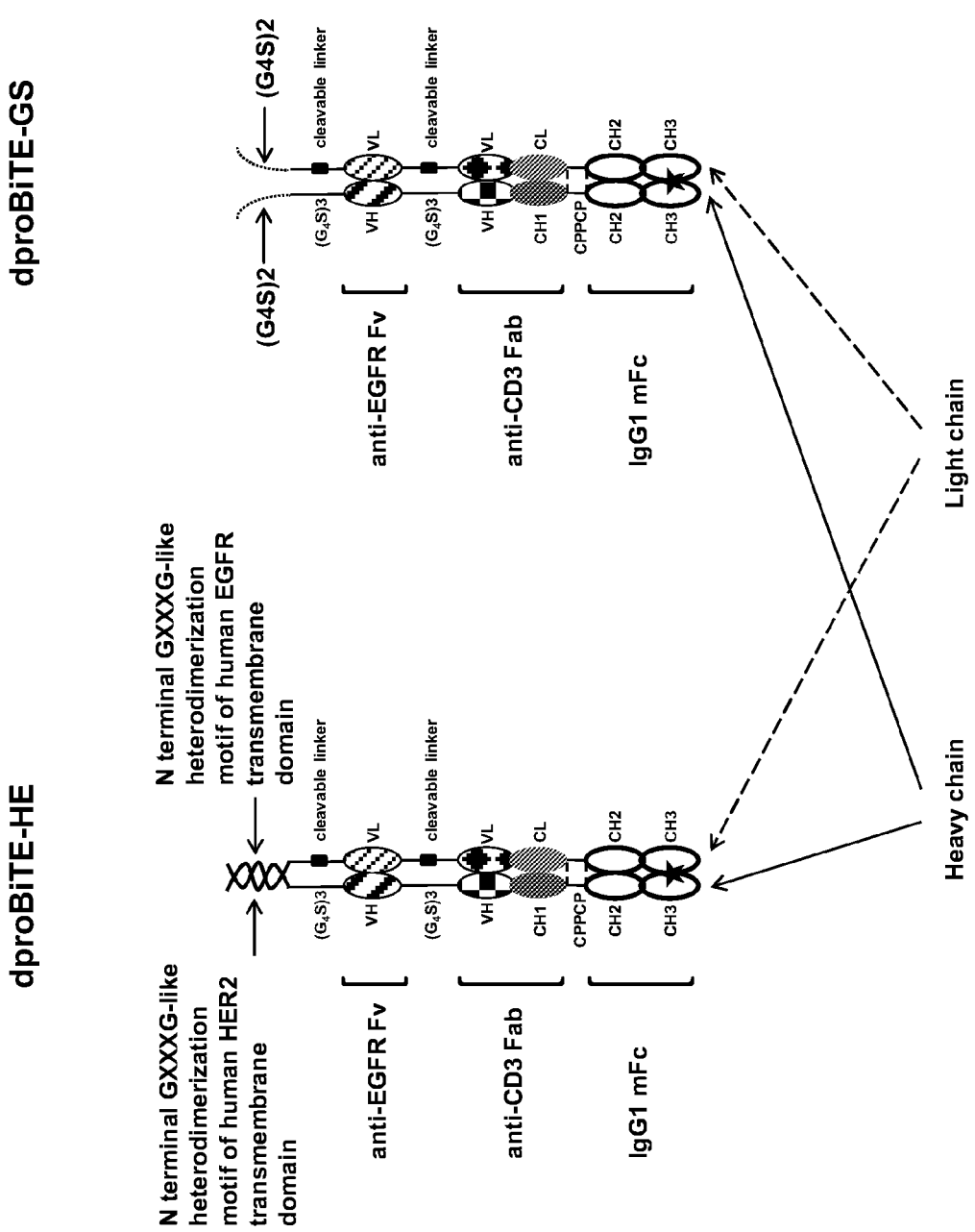
FIG. 27 shows schematic representation of EGFR×CD3 dproBiTE. The antibody polypeptide chain containing anti-CD3 VH-CH1 sequence is designated heavy chain and the one with anti-CD3 VL-CL sequence is designated light chain, regardless of their molecular weights. Stars denote mutations which decrease or abrogate Fc homodimerization.

To test the above hypothesis, two EGFR×CD3 dproBiTE, designated dproBiTE-HE and dproBiTE-GS were generated. dproBiTE-HE carries the N terminal GXXXG-like heterodimerization motif (LTSIISAVVG, (SEQ ID NO:65)) of human HER2 transmembrane domain and the N terminal GXXXG-like heterodimerization motif (SIATGMVG, (SEQ ID NO:66)) of human EGFR transmembrane domain, fused to the VH and VL domains of anti-EGFR antibody in proBiTE-1s1 via a non-cleavable and cleavable linker composed of the (G4S)3 and (SEQ ID NO: 67)
GGGGSGGGGSGRSDNH (underlined is the mutated substrate of uPA, matriptase and legumain) sequences, respectively (FIG. 27). In dproBiTE-GS, the HER2 and EGFR heterodimerization mitifs were replaced with (G4S)2 sequence.

Figure 28:
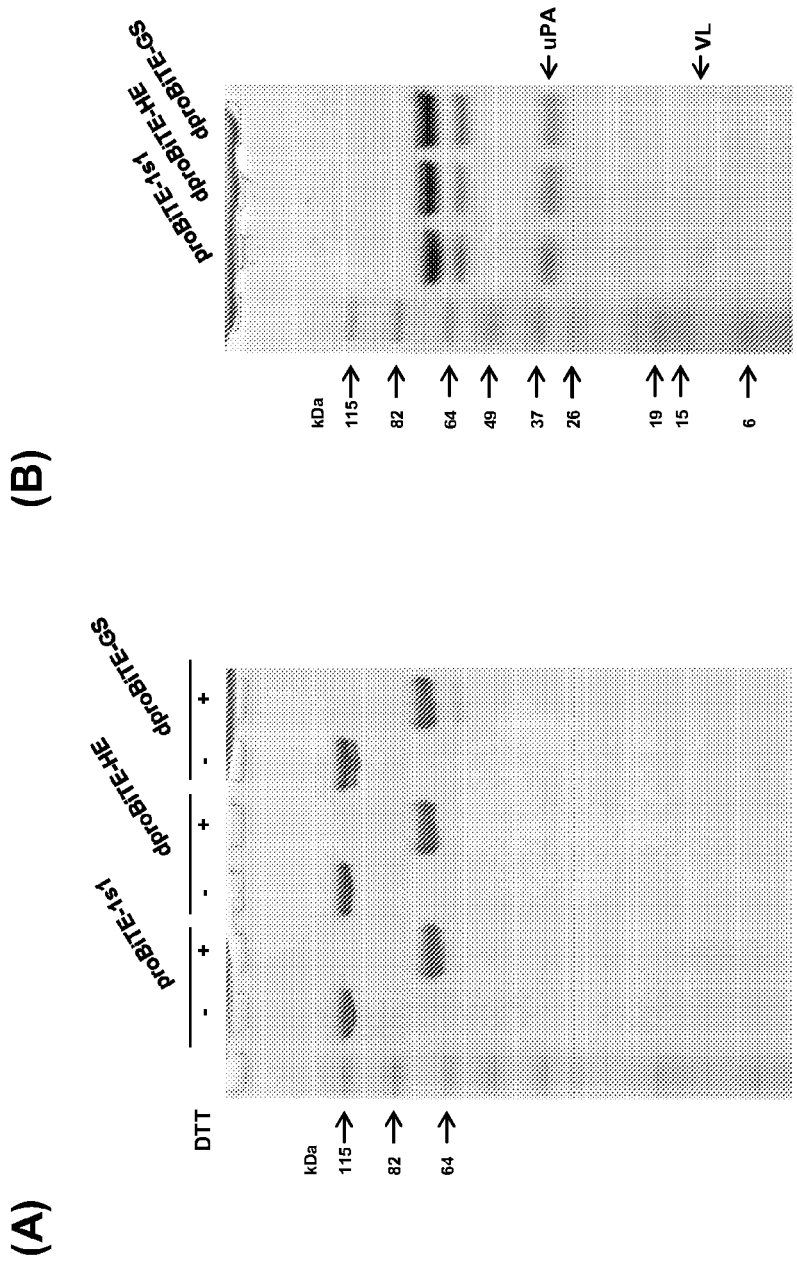
FIGS. 28A-B show results of SDS-PAGE of dproBiTE-HE and dproBiTE-GS.
Figure 29:
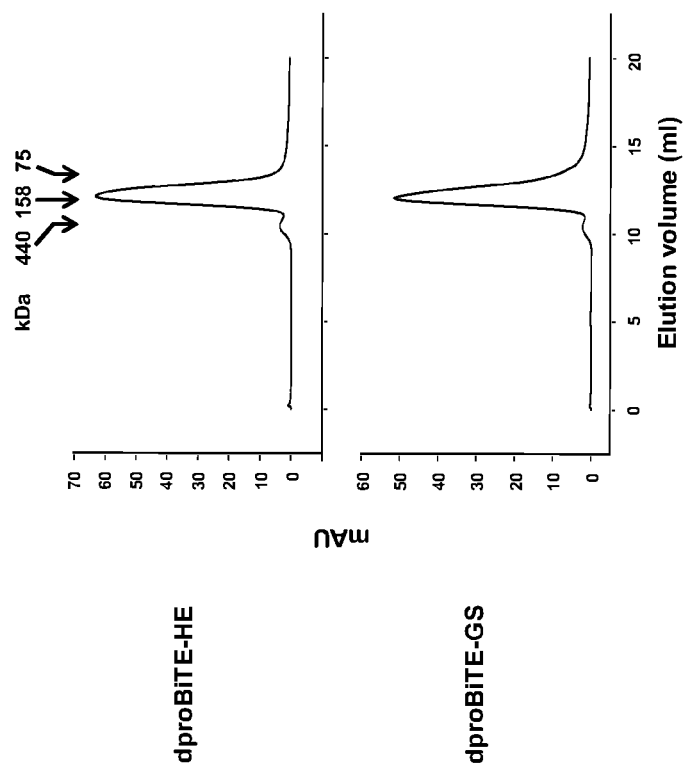
FIG. 29 shows size-exclusion chromatography of dproBiTE-HE and dproBiTE-GS. The arrows at the top indicate the elution volumes of the molecular mass standards in PBS (pH7.4): ferritin (440 kDa), aldolase (158 kDa) and conalbumin (75 kDa).
Figure 30:
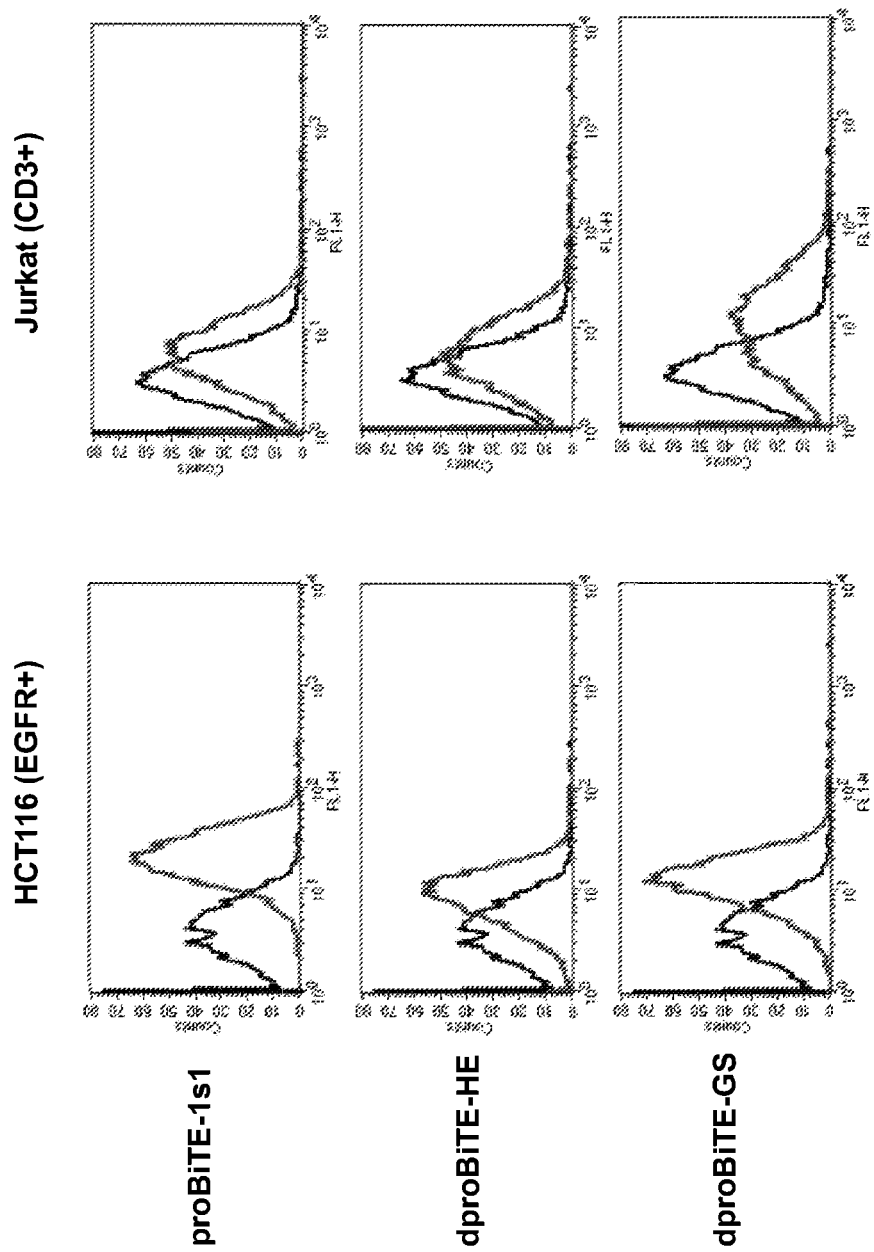
FIG. 30 shows binding of dproBiTE-HE and dproBiTE-GS to cell-surface EGFR and CD3 as measured by flow cytometry. The tracings on the left in each panel represent reference cells which were incubated with secondary antibody, FITC-conjugated anti-human IgG (Fc-specific), only. The tracings on the right in each panel represent experimental groups, in which the cells were first incubated with bispecific antibodies at a concentration of 2 µg/mL and then with the secondary antibody.

The two dproBiTEs were well expressed in transiently transfected 293 free style (293FS) cells and secreted into the culture supernatants. On a non-reducing SDS-PAGE, a vast majority of the purified antibodies migrated as a heterodimer with apparent molecular weight (aMW) of approximately 115 kDa (FIG. 28A). On a reducing SDS-PAGE, the two polypeptide chains of dproBiTE overlapped with each other with apparent molecular weight slightly larger than those of proBiTE-1s1. Similar with proBiTE-1s1, dproBiTE-HE and dproBiTE-GS were efficiently cleaved by uPA, resulting in an isolated VL domain of the anti-EGFR antibody (FIG. 28B). Size-exclusion chromatography showed that the vast majority of the purified antibodies migrated as a monomer with aMW of approximately 120 kDa, similar to their calculated molecular weight (cMW) (FIG. 29). In flow cytometry analysis, dproBiTE-HE bound to EGFR-expressing HCT116 cells less strongly than proBiTE-1s1 and their binding to CD3-expressing Jurkat cells was not affected, as expected (FIG. 30).

Example 12

Generation of Anti-EGFR Antibodies

This example describes one embodiment of generating anti-EGFR (epidermal growth factor receptor) antibodies.

Materials and Methods

Cells, Proteins, Plasmids and Other Reagents 293 free style (293FS) cells and protein A agarose were purchased from ThermoFisher Scientific. CHO and A549 cells were purchased from ATCC. Recombinant human and cynomolgus EGFR were products of Sino Biological. Recombinant human EGF was a product of AcroBiosystems. The pDin1 vector used for mammalian expression was synthesized and assembled by overlapping PCR and ligation. The vector contains two transcription units and a built-in human IgG1 Fc gene fragment without introns that facilitates cloning of IgG1 or Fc-fusion proteins. Horseradish peroxidase (HRP)-conjugated goat anti-human IgG (Fc-specific) antibody and HRP-conjugated anti-FLAG antibody were products of Sigma. Anti-His-PE conjugate was purchased from Miltenyi Biotec. Goat F(ab')2 anti-human IgG (γ)-FITC conjugate was purchased from ThermoFisher Scientific.

Panning and Screening of a Phage-Display Naïve Human Fab Library for Identification of EGFR Antibodies A large size ($10^{11}$) phage-display naïve human Fab library was constructed with peripheral blood B cells from about 100 healthy individuals according to previously published protocols (de Haard et al., J Biol Chem 1999, 274: 18218-18230). This library was used for selection of antibodies against recombinant human EGFR conjugated to magnetic beads (Dynabeads M-270 epoxy; DYNAL Inc.) as described previously (Zhu et al., J Virol 2006, 80:891-899) except 5, 1 and 0.1 μg of antigen were used in the first, second and third round of panning, respectively. Clones that bound to the antigen were identified from the third round of biopanning by using monoclonal phage ELISA as described (Zhu et al., J Virol 2006, 80:891-899).

Affinity Maturation of SMET5

For affinity maturation of SMET5, a phage-display light-chain shuffling Fab library was constructed and panned, and SMET5 variants with higher binding activity were selected according to previously reported protocol (Zhu et al., J Infect Dis 2008, 197: 846-853).

Cloning of Human IgG1 of SMET5 Variants

The following primers were used:
ER1HF, (sense) (SEQ ID NO:100); ER1HR, (antisense) (SEQ ID NO:101)
ER1LF, (sense) (SEQ ID NO:102); ER1LR, (antisense) (SEQ ID NO:103)
ER12LF1, (sense) (SEQ ID NO:104); ER12LR1, (antisense) (SEQ ID NO:105)
ER12LF2, (sense) (SEQ ID NO:106); ER13LF, (sense) (SEQ ID NO:107)
bnIgG20H1, (sense) (SEQ ID NO:108); bnIgG20L1, (sense) (SEQ ID NO:109).

For cloning of SMET5 IgG1, SMET5 VH gene fragment was PCR amplified with primers ER1HF and ER1HR. A gene fragment (Hleader) encoding a leader peptide was fused to the VH by overlapping PCR with the two gene fragments in the same molarities for 7 cycles in the absence of primers and 15 additional cycles in the presence of primers bnIgG20H1 and ER1HR. The overlapping PCR product Hleader-VH was digested with XbaI and SacI and cloned into pDin1 vector with built-in gene sequence encoding the human IgG1 heavy chain constant regions. SMET5 L chain gene fragment was PCR amplified with primers ER1LF and ER1LR. A gene fragment (Lleader) encoding a leader peptide was fused to the L chain by overlapping PCR with primers bnIgG20L1 and ER1LR. The overlapping PCR product Lleader-L was digested with HindIII and EcoRI and cloned into the pDin1 construct containing the heavy chain of SMET5 IgG1.

For cloning of SMET5.2 IgG1, the N and C terminal portions of SMET5.2 L chain gene fragment were PCR amplified with primer pairs ER12LF1/ER12LR1 and ER12LF2/ER1LR, respectively. The whole-length SMET5.2 L chain was assembled by overlapping PCR with primers ER12LF1 and ER1LR. The Lleader gene fragment was then fused to the L chain by overlapping PCR with primers bnIgG20L1 and ER1LR. The overlapping PCR product Lleader-L was digested with HindIII and EcoRI and cloned into the pDin1 construct containing the heavy chain of SMET5 IgG1.

For cloning of SMET5.3 IgG1, the L chain of SMET5.3 was PCR amplified with primers ER13LF and ER1LR. The Lleader gene fragment was then fused to the L chain by overlapping PCR with primers bnIgG20L1 and ER1LR. The overlapping PCR product Lleader-L was digested with HindIII and EcoRI and cloned into the pDin1 construct containing the heavy chain of SMET5 IgG1.

Protein Expression And Purification

Fab antibodies were expressed in *E. coli* HB2151 cells and IgG1s were expressed in 293FS cells as described previously (Chen et al., Proc Natl Acad Sci USA 2008, 105: 17121-17126). His-tagged Fab antibodies were purified from the soluble fraction of HB2151 periplasm by using the Ni-NTA resin (Qiagen) according to the manufacturer's protocol. IgG1s were purified from the 293FS culture supernatant by using Protein A Sepharose 4 Fast Flow column chromatography (GE Healthcare) according to the manufacturer's instructions.

ELISA

ELISA was performed according to standard protocols. Briefly, recombinant human or cynomolgus EGFR was coated on Corning EIA/RIA high-binding 96-well plates (Corning Inc.) at 50 ng per well overnight at 4° C. and blocked with 3% nonfat milk in PBS (pH7.4). Fivefold serially diluted antibodies were added and incubated at room temperature for 2 hours. The plates were washed with PBS containing 0.05% Tween 20. Bound Fab and IgG1s were detected by HRP-conjugated anti-FLAG tag antibody and HRP-conjugated anti-human IgG (Fc-specific) antibody, respectively. The assay was developed at room temperature with TMB substrate (Sigma-Aldrich) and monitored at 450 nm with a microplate reader. The half-maximal binding ($EC_{50}$) was calculated by fitting the data to the Langmuir adsorption isotherm.

Flow Cytometry

To measure the binding of SMET5 Fab to cell surface EGFR, about $5 \times 10^5$ cells were incubated with 100 nM antibody on ice for 1 h. The cells were washed once with PBS containing 0.1% bovine serum albumin (PBSA) and resuspended in 200 µl PBSA. Then 5 µl anti-His-PE conjugate was added and incubated for 30 min. The cells were washed once with PBSA and then used for flow cytometry analysis.

To measure the binding of IgG1 s of SMET5 variants to cell surface EGFR, about $5 \times 10^5$ cells were incubated with 2 µg mL$^{-1}$ antibodies on ice for 1 h. The cells were washed once with PBSA and resuspended in 200 µl PBSA. Then 5 µl goat F(ab')2 anti-human IgG (γ)-FITC conjugate was added and incubated for 30 min. The cells were washed once with PBSA and then used for flow cytometry analysis.

To measure the competitive binding of SMET5.2 IgG1 and EGF to cell surface EGFR, about $5 \times 10^5$ cells were incubated with SMET5.2 IgG1 at 2 µg mL$^{-1}$ in the absence or presence of EGF at 40 µg mL$^{-1}$ on ice for 30 min. The cells were washed with PBSA once and resuspended in 200 µl PBSA. Then 4 µl goat F(ab')2 anti-human IgG (γ)-FITC conjugate were added and incubated for 30 min. The cells were washed once with PBSA and then used for flow cytometry analysis.

Pharmacokinetic Measurement in Mice

NOD/SCID mice were administered intravenously with 500 µg antibody on day 0. Plasma samples were collected on day 1, 3, 5 and 6 and used for measurement of antibody serum concentrations by ELISA with standard curves generated using the original antibody stocks.

In-Vivo Tumor Growth Inhibition

SCID mice were inoculated with $10^6$ A431 cells subcutaneously into the left flank of the mice. Once tumors reached a volume of 100-150 mm$^3$, mice were randomized into groups of 5 mice/group of equal average tumor volume and reconstituted intravenously with $10^7$ human PBMCs. One day later, the mice were dosed intravenously with PBS, 0.5 mg SMET5.2 IgG1, or 0.5 mg control antibody every 3-4 days for 6 doses. After one month of treatment, mice were sacrificed and tumor weights were measured. Tumor growth inhibition rates were calculated by using the following formula: average weight of PBS group−average weight of antibody treated group/average weight of PBS group.

Results and Discussion

Selection and Affinity Maturation of Fully Human Anti-EGFR Antibodies

Figure 31:
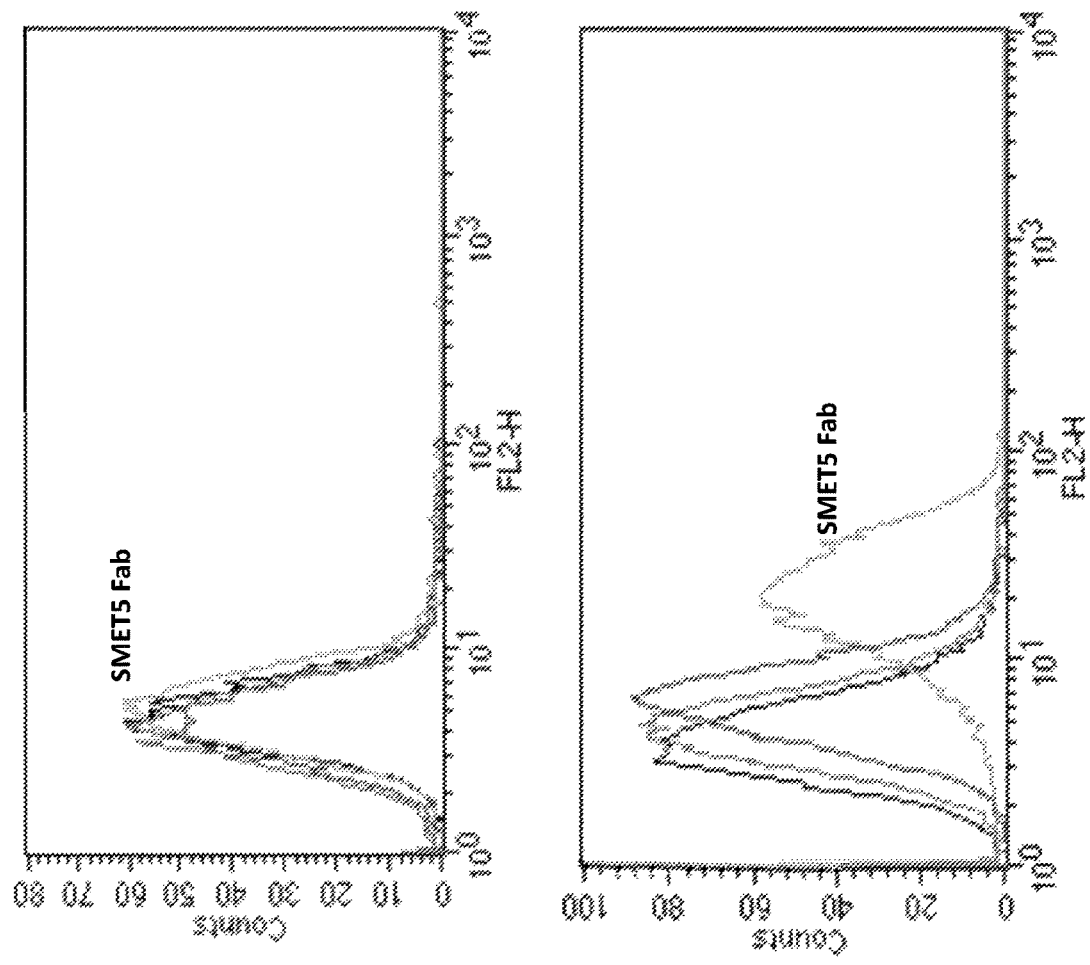
FIG. 31 shows binding of the selected anti-EGFR antibodies (SMET5 Fab) to cell surface EGFR as measured by flow cytometry.
Figure 32:
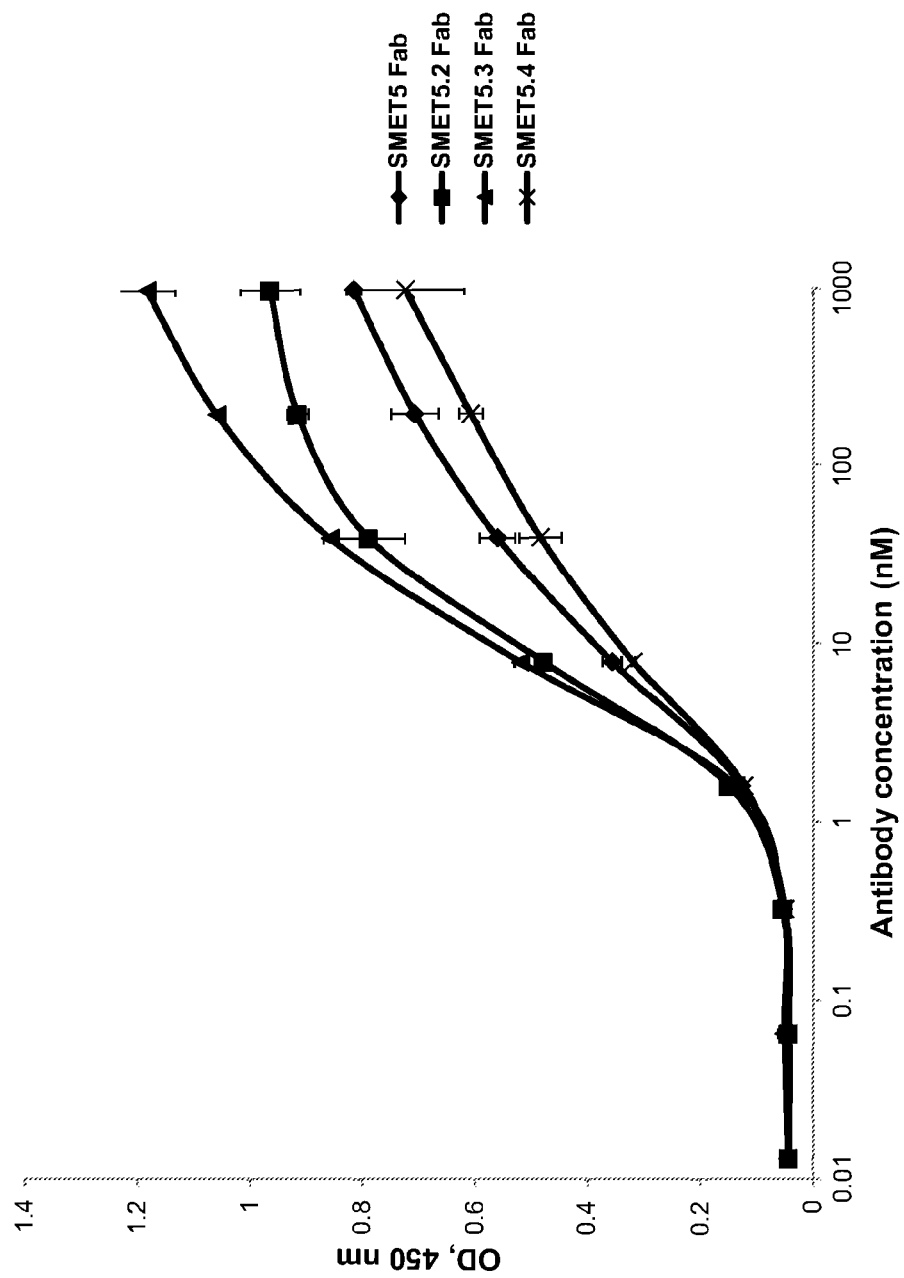
FIG. 32 shows affinity maturation of SMET5 Fab variants by light chain shuffling.

Panning and screening a large phage-display naïve human Fab library led to the identification of three antibodies against EGFR. One of the antibodies, designated SMET5, significantly bound to EGFR-expressing human lung cancer cell line A549 but not to human EGFR-negative CHO cells, hence indicating specificity of the antibody (FIG. 31). To improve its affinity, a light chain shuffling Fab library was constructed with the heavy chain of SMET5. Panning and screening the new library resulted in the identification of three SMET5 variants, namely SMET5.2, SMET5.3 and SMET5.4. In an ELISA, SMET5.2 and SMET5.3 showed higher binding activity against recombinant human EGFR than SMET5 whereas SMET5.4 had slightly decreased binding activity (FIG. 32).

Generation and In Vitro Characterization of IgG1 of SMET5. SMET5.2 and SMET5.3

Figure 33:
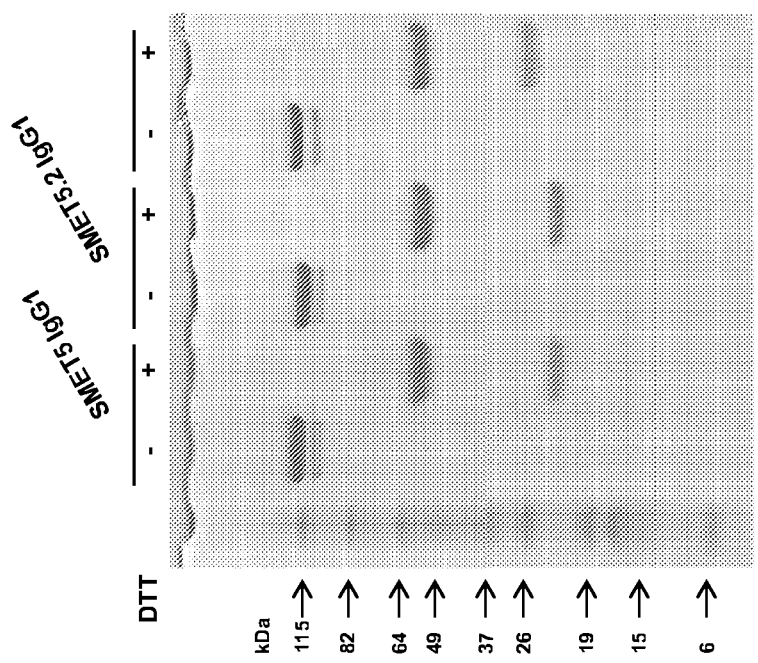
FIG. 33 shows results of SDS-PAGE of SMET5 variants.
Figure 34:
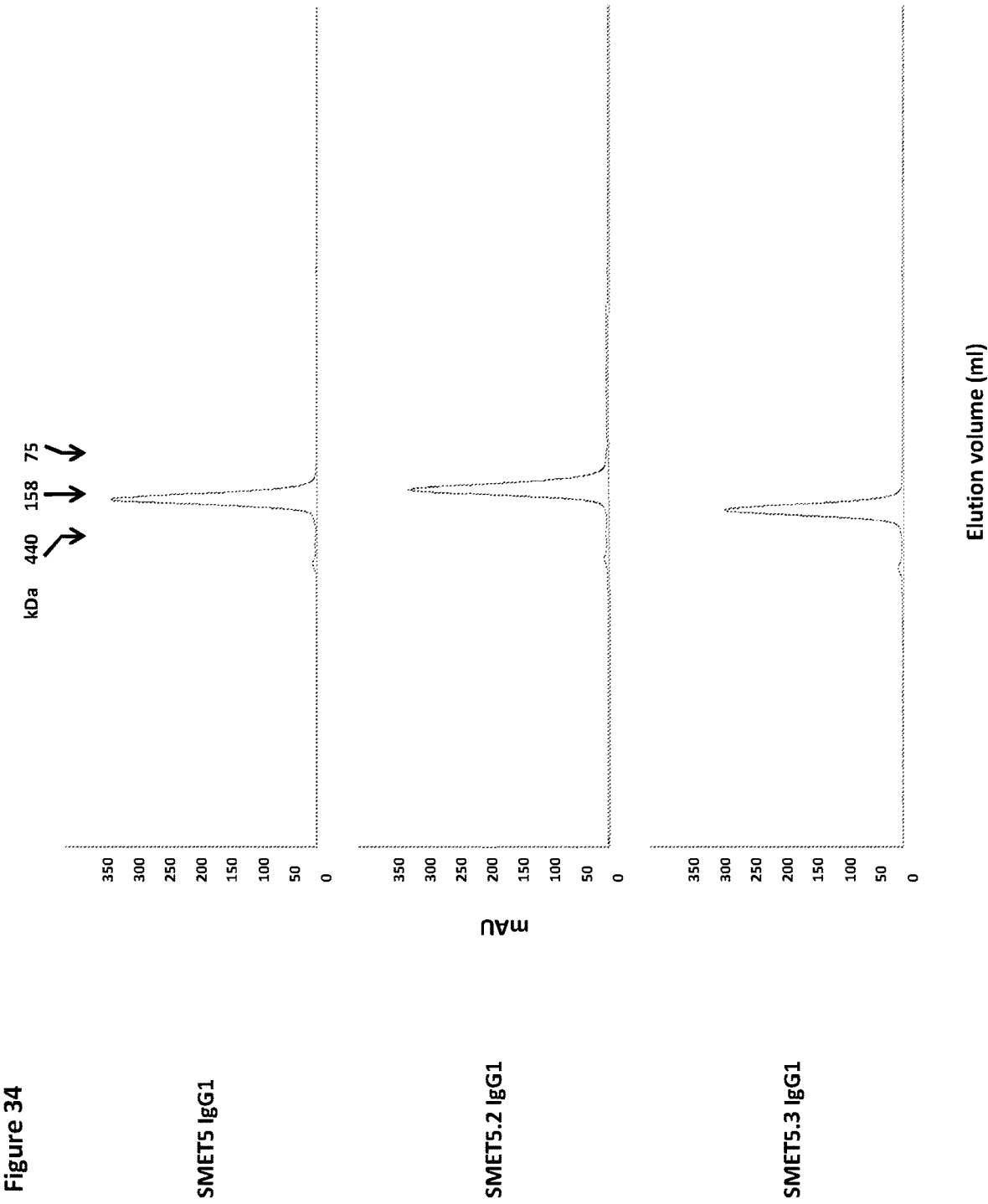
FIG. 34 shows size-exclusion chromatography of SMET5 variants. The arrows at the top indicate the elution volumes of the molecular mass standards in PBS (pH7.4): ferritin (440 kDa), aldolase (158 kDa) and conalbumin (75 kDa).
Figure 35:
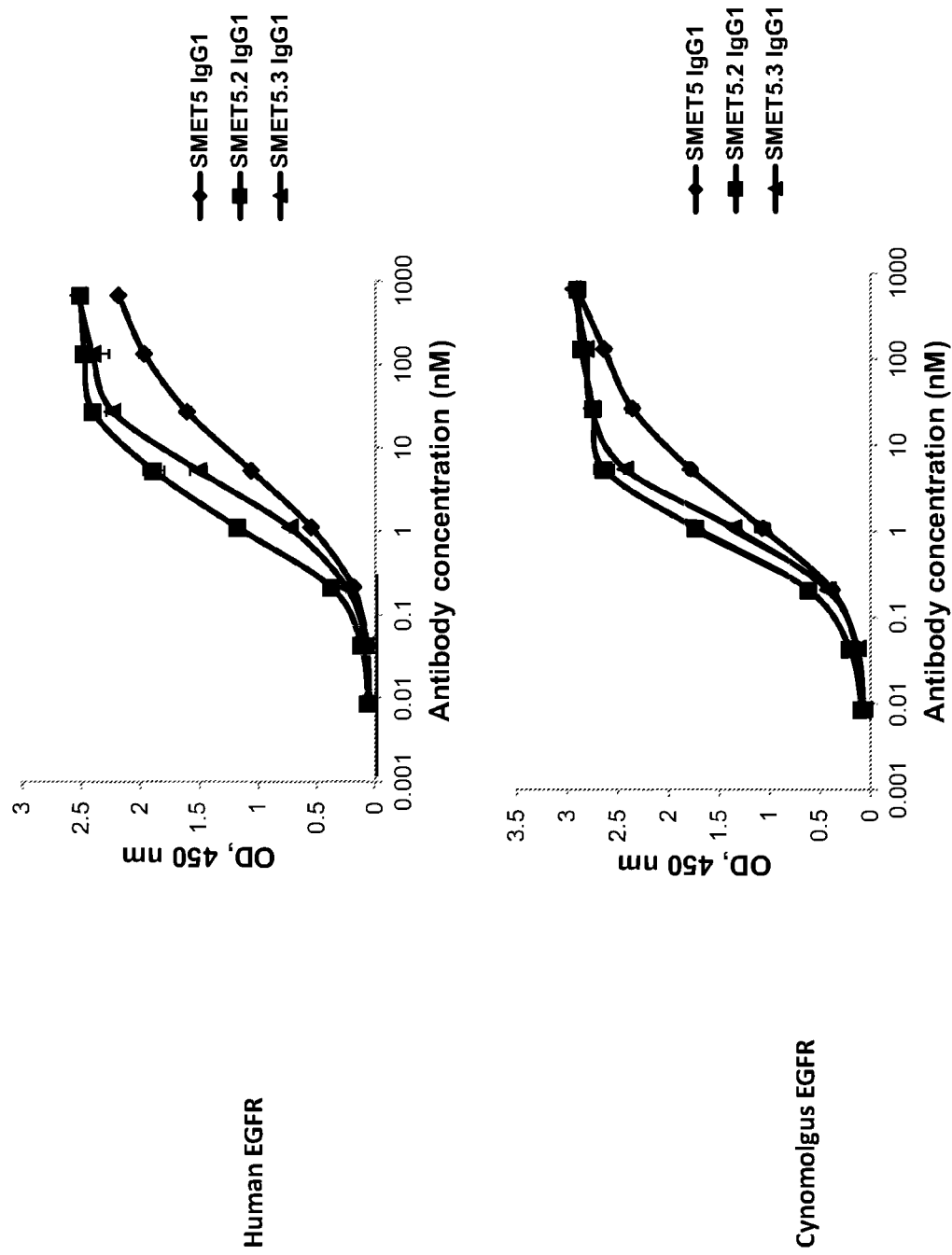
FIG. 35 shows ELISA binding of SMET5 variants to recombinant human and cynomolgus EGFR.
Figure 36:
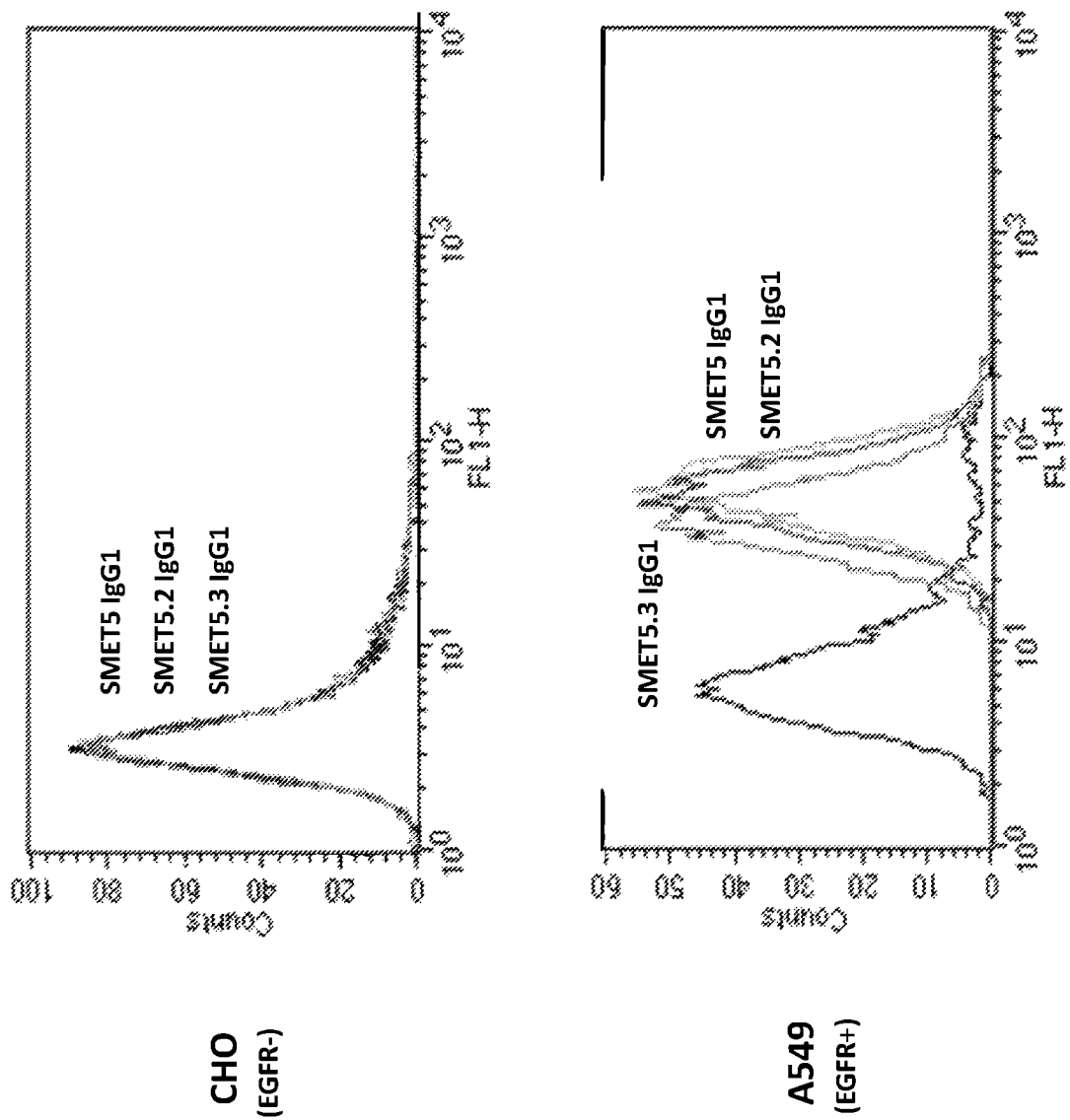
FIG. 36 shows binding of SMET5 variants to cell surface EGFR as measured by flow cytometry.
Figure 37:
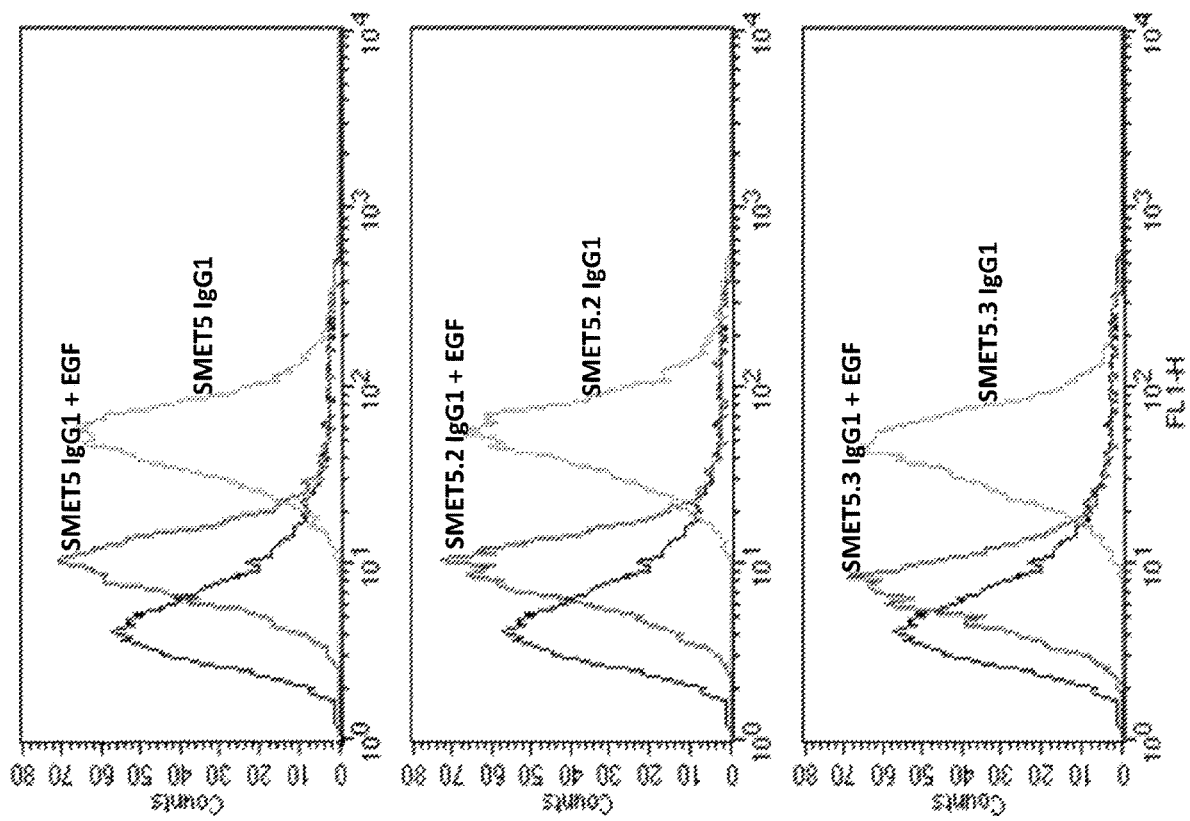
FIG. 37 shows competition of EGF and SMET5 variants for binding to cell surface EGFR as measured by flow cytometry.

To evaluate the potential of the EGFR antibodies to be developed as candidate therapeutics, full-length SMET5, SMET5.2 and SMET5.3 antibodies were generated in the IgG1 format, which confers bivalency (avidity) and long half-life in vivo. The IgG1 antibodies were expressed and purified from transiently transfected 293FS cell culture supernatants by using protein A with yield of 10-20 mg L$^{-1}$ (FIG. 33). Size-exclusion chromatography revealed that the vast majority (>95%) of the purified IgG1 s in PBS (pH7.4) were monomers with apparent molecular weights of approximately 150 kDa, comparable to their calculated molecular weights (FIG. 34). In an ELISA, they showed cross-reactivity with human and cynomolgus EGFR with SMET5.2 IgG1 having highest binding activity ($EC_{50}$s, 1.4 nM for human EGFR and 0.76 nM for cynomolgus EGFR) (FIG. 35). At a concentration of 2 µg $mL^{-1}$, SMET5 and SMET5.2 IgG1s had comparable binding to A549 cells while SMET5.3 IgG1 showing relatively lower binding activity (FIG. 36). No binding was detected with CHO cells suggesting high specificity of the IgG1 s. All the IgG1s efficiently competed with EGF for binding to cell surface EGFR (FIG. 37).

Inhibition of Tumor Growth in NOD/SCID Mice Engrafted with Human PBMC

Figure 38:
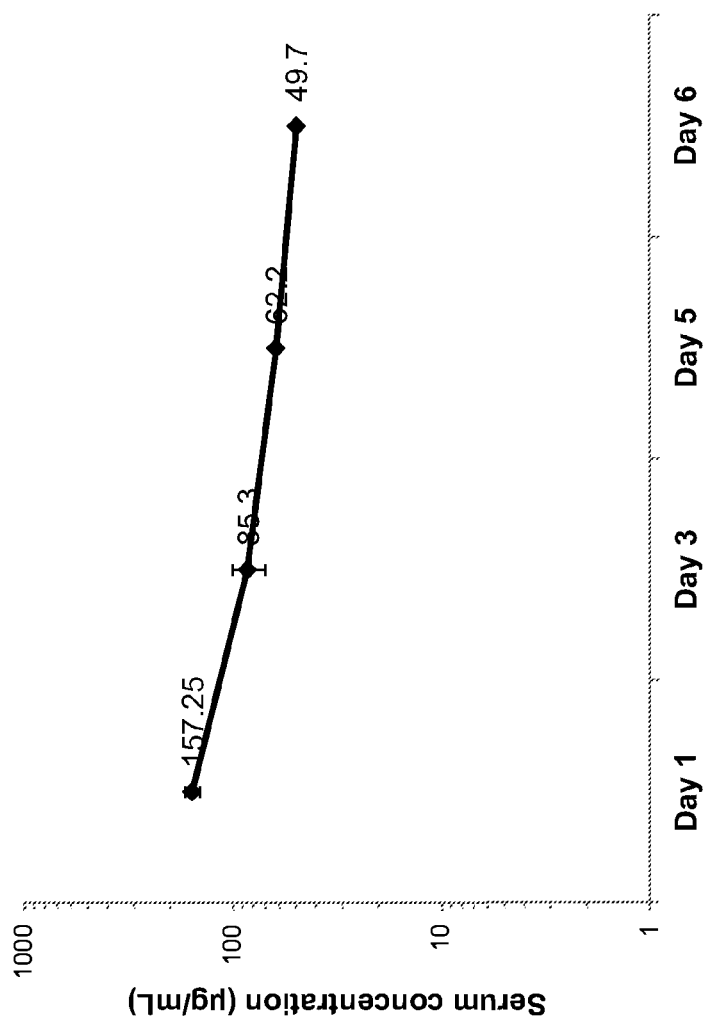
FIG. 38 shows pharmacokinetics of SMET5.2 IgG1 in NOD/SCID mice.
Figure 39:
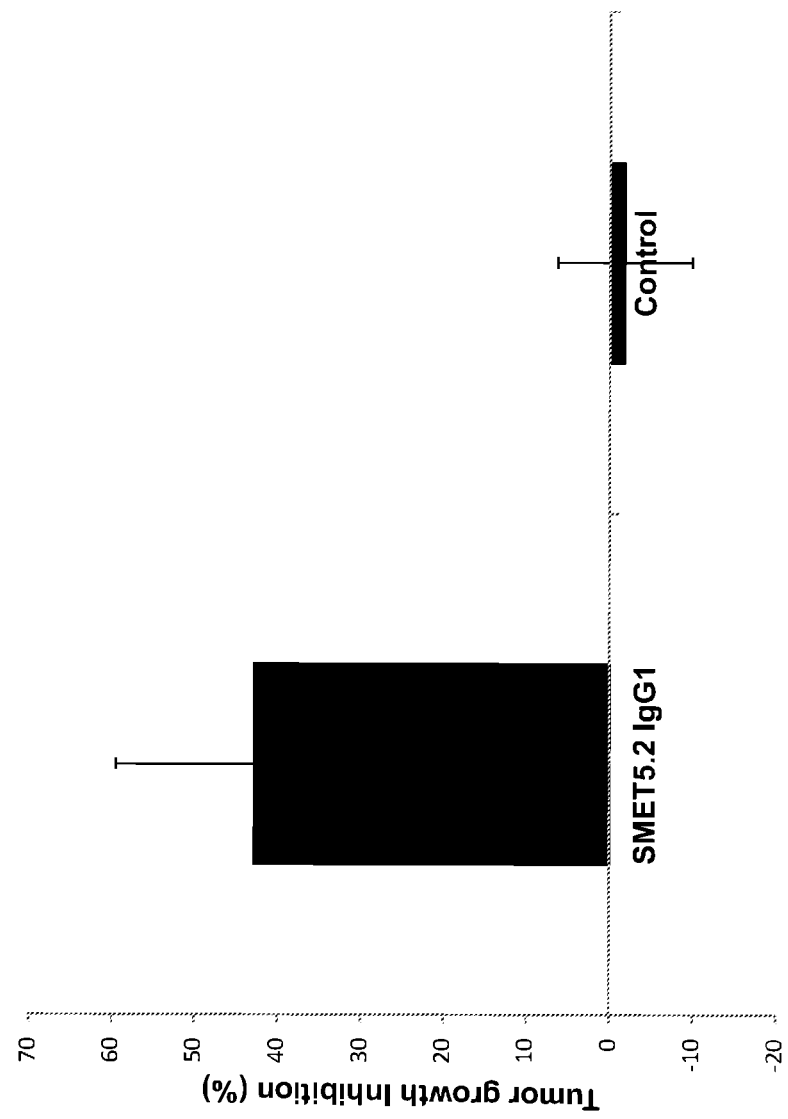
FIG. 39 shows antitumor activity of SMET5.2 IgG1 in NOD/SCID mice engrafted with human PBMC and A431 cells.

To test how the antibodies could inhibit tumor growth in vivo, NOD/SCID mice engrafted with A431 cells and human PBMC were used as a model. Pharmacokinetics analysis showed that SMET5.2 IgG1 was cleared slowly from the mouse circulation (FIG. 38). In the tumor challenge experiment, the antibody significantly inhibited the growth of A431 cells in the animals (FIG. 39).

Example 13

Cloning of EGFR×CD3 Bispecific Antibodies with Reduced Binding Affinity to CD3 Cells, Proteins, Plasmids and Other Reagents 293 free style (293FS) cells and protein A agarose were purchased from ThermoFisher Scientific. HCT116 and HT29 colon cancer cell lines were purchased from Sigma. Other cell lines were purchased from ATCC. Recombinant human EGFR, human CD3 (hCD3), cynomolgus CD3 (cCD3), and urokinase (uPA) were products of Sino Biological. The pDin1 vector used for mammalian expression was synthesized and assembled by overlapping PCR and ligation. The vector contains two transcription units and a built-in human IgG1 Fc gene fragment without introns that facilitates cloning of IgG1 or Fc-fusion proteins. Horseradish peroxidase (HRP)-conjugated goat anti-human IgG (Fc-specific) antibody was a product of Sigma. Goat anti-human IgG (Fc-specific)-FITC conjugate was purchased from ThermoFisher Scientific.

Cloning of EGFR×CD3 Bispecific Antibodies with Reduced Binding Affinity to CD3

The following primers were used:
SP34HF, (sense) (SEQ ID NO:110); SP34HR, (antisense) (SEQ ID NO:111)
CFCF, (sense) (SEQ ID NO:112); MFc7.2R1, (antisense) (SEQ ID NO:113)
SP34LF, (sense) (SEQ ID NO:114); SP34LR, (antisense) (SEQ ID NO:115)
CFCPAF, (sense) (SEQ ID NO:116); AAAR, (antisense) (SEQ ID NO:117)
bnIgG20H1, (sense) (SEQ ID NO:118)
SFPAF, (sense) (SEQ ID NO:119)
SFF, (sense) (SEQ ID NO:120); VNFR, (antisense) (SEQ ID NO:121)
bnIgG20L1, (sense) (SEQ ID NO:122)
VNFF, (sense) (SEQ ID NO:123); HSPGF, (anti sense) (SEQ ID NO:124)

Cloning of iBiTE-sp

Humanized SP34 (hSP34) antibody scFv gene (see U.S. Pat. Nos. 8,236,308 and 9,493,563) was chemically synthesized by Integrated DNA technologies. To clone the heavy chain of iBiTE-sp (see FIG. 40), hSP34 VH gene fragment was PCR amplified with the synthesized hSP34 scFv gene as a template and primers SP34HF and SP34HR. A gene fragment encoding human IgG1 CH1 and monomeric Fc (CH1-mFc7.2) was PCR amplified with previously constructed plasmid iBiTE (U.S. provisional patent application No. 62/783,411) as a template and primers CFCF and MFc7.2R1. hSP34 VH gene fragment was fused to the 5' end of CH1-mFc7.2 by overlapping PCR with the two gene fragments in the same molarities for 7 cycles in the absence of primers and 15 additional cycles in the presence of primers SP34HF and MFc7.2R1. The overlapping product hSP34 VH-CH1-mFc7.2 was digested with SacI and EcoRI and cloned into the iBiTE plasmid with inserted anti-EGFR antibody SMET5.2 scFv.

To clone the light chain of iBiTE-sp (see FIG. 40), hSP34 VL gene fragment was PCR amplified with the synthesized hSP34 scFv as a template and primers SP34LF and SP34LR. A gene fragment encoding human antibody CL domain, monomeric Fc and a poly A signal sequence (CL-mFc7.2-polyA) was PCR amplified with previously constructed plasmid iBiTE as a template and primers CFCPAF and AAAR. A gene fragment (Hleader) encoding a leader peptide was then fused to the 5' end of hSP34 VL by overlapping PCR with primers bnIgG20H1 and SP34LR. Hleader-hSP34 VL was further linked to the 5' end of CL-mFc7.2-polyA by overlapping PCR with primers bnIgG20H1 and AAAR. The product was digested with XbaI and SalI and cloned into the previous plasmid containing hSP34 VH-CH1-mFc7.2, resulting in the final construct iBiTE-sp.

Cloning of proBiTE-1s1sp

A gene fragment encoding hSP34 VL-CL-mFc7.2-polyA was PCR amplified with iBiTE-sp as a template and primers SFPAF and AAAR. The PCR product was digested with BamHI and SalI and cloned into a previously constructed plasmid proBiTE-1s1 (U.S. provisional patent application No. 62/783,411). Then, a gene fragment encoding hSP34 VH-CH1-mFc7.2 was PCR amplified with iBiTE-sp as a template and primers SFF and MFc7.2R1. The PCR product was digested with SacI and EcoRI and cloned into the previous plasmid containing hSP34 VL-CL-mFc7.2-polyA, resulting in the final construct proBiTE-1s1sp.

Cloning of proBiTE-1s1spg

A gene fragment encoding a leader peptide, anti-EGFR antibody SMET5.2 VH and the N terminal portion of hSP34 VH was PCR amplified with proBiTE-1s1sp as a template and primers bnIgG20L1 and VNFR. Another gene fragment encoding the C terminal portion of hSP34 VH and CH1-mFc7.2 was PCR amplified with proBiTE-1s1sp as a template and primers VNFF and MFc7.2R1. The two gene fragments were fused to each other by overlapping PCR with primers bnIgG20L1 and MFc7.2R1. The product was digested with HindIII and EcoRI and cloned into proBiTE-1s1sp, resulting in the final construct proBiTE-1s1spg.

Cloning of HBiBody-spg

A gene fragment encoding hSP34 L chain, mFc7.2 and polyA signal sequence was PCR amplified with proBiTE-1s1spg as a template and primers HSPGF and AAAR. The PCR product was digested with BamHI and SalI and cloned into proBiTE-1s1spg linearized by BamHI and SalI.

Protein Expression And Purification

All bispecific antibodies were expressed in 293FS cells as described previously (Chen et al., Proc Natl Acad Sci USA 2008, 105:17121-17126) and purified from the 293FS culture supernatant using Protein A Sepharose 4 Fast Flow column chromatography (GE Healthcare) according to the manufacturer's instructions.

Protease Cleavage

For cleavage with urokinase (uPA), 5 μg antibodies were mixed with or without 1 μg recombinant human uPA (Sino Biological) in 15 μl PBS (pH7.4) and incubated at room temperature for 1 hour.

ELISA

ELISA was performed according to standard protocols. Briefly, recombinant antigens were coated on Corning EIA/RIA high-binding 96-well plates (Corning Inc.) at 100 ng per well overnight at 4° C. and blocked with 3% nonfat milk in PBS (pH7.4). Fivefold serially diluted biotinylated antibodies were added and incubated at room temperature for 2 hours. The plates were washed with PBS containing 0.05% Tween 20. Bound antibodies were detected by goat anti-human IgG (Fc-specific) antibody. The assay was developed at room temperature with TMB substrate (Sigma-Aldrich) and monitored at 450 nm with a microplate reader. Half-maximal binding ($EC_{50}$) was calculated by fitting the data to the Sigmoidal adsorption isotherm.

Flow Cytometry

About $5 \times 10^5$ cells were incubated with antibodies on ice for 1 hour. The cells were washed once with PBS containing 0.1% bovine serum albumin (PBSA) and resuspended in 100 μl PBSA. Then 1 μl goat anti-human IgG (Fc-specific)-FITC conjugate (Invitrogen) was added and incubated for 30 min. The cells were washed once with PBSA and then used for flow cytometry analysis. $EC_{50}$ was calculated by fitting the data to the Sigmoidal isotherm.

Size-Exclusion Chromatography

A Superdex200 10/300 GL column (GE Healthcare) was calibrated with protein molecular mass standards of carbonic anhydrase (29 kDa), ovalbumin (44 kDa), conalbumin (75 kDa), aldolase (158 kDa) and ferritin (440 kDa). Purified proteins at a concentration of 1 mg/mL in PBS (pH7.4) were loaded onto the pre-equilibrated column and eluted with PBS (pH7.4) at 0.5 mL/min.

In-Vitro Killing Assay

For the assay using luciferase as a reporter gene, $10^4$ target cells were seeded in 100 μl RPMI 1640 complete medium overnight. Meanwhile, $2.5 \times 10^7$ frozen human peripheral blood mononuclear cells (PBMCs) purchased from STEMCELL Technologies were revived and cultured in 10 mL RPMI 1640 complete medium containing 50 U/mL IL-2 (Sigma) overnight. The medium was removed from the target cells on the next day and $5 \times 10^4$ PBMCs in 50 μl RPMI 1640 complete medium were added (actual target:effector ratio=1:2.5 because the target cells duplicated overnight). Then, 50 μl antibodies (5-fold serially diluted from 1 nM) were added into each well. Twenty four hours later, 20 μl of adenovirus encoding luciferase gene (Ad5-Luc) was added at a multiplicity of infection (MOI) of 100, which effectively infects target cells but not effector cells. Twenty four hours later, cell viability was measured using Promega Bright-Glo Luciferase Assay System according to the manufacturer's instructions. Cell killing was calculated using the following formula: 1−(average reading of antibody and Ad5-Luc treated group−average reading of cell only group)/(average reading of PBS and Ad5-Luc treated group −average reading of cell only group).

For the assay using MTS tetrazolium compound as a reporter reagent, $10^4$ target cells were seeded in 100 μl RPMI 1640 complete medium overnight. Meanwhile, $2.5 \times 10^7$ frozen human peripheral blood mononuclear cells (PBMCs) purchased from STEMCELL Technologies were revived and cultured in 10 mL RPMI 1640 complete medium containing 50 U/mL IL-2 (Sigma) overnight. The medium was removed from the target cells on the next day and $10^5$ PBMCs in 50 μl RPMI 1640 complete medium were added (actual target:effector ratio=1:5 because target cells duplicated overnight). Then, 50 μl antibodies (5-fold serially diluted from 10 nM) were added into each well. Forty eight hours later, the plates were gently shaked and resuspended PBMCs were removed together with used medium. Each well of the plates was washed once with 100 μl fresh RPMI 1640 complete medium to completely remove resuspended PBMCs. Then 100 μl fresh RPMI 1640 complete medium was added into each well and cell viability was measured using Promega CellTiter 96® $AQ_{ueous}$ One Solution Cell Proliferation Assay according to the manufacturer's instructions. Cell killing was calculated using the following formula: 1−(average reading of antibody treated group−average reading of medium only group)/(average reading of PBS treated group−average reading of medium only group).

Example 14

Design of New Bispecific EGFR×CD3 Antibodies with Reduced Binding to CD3

To provide a proof-of-concept, anti-EGFR and anti-CD3 antibodies were used as examples here and below. One of ordinary skill in the art would recognize that other T and non-T cell target antigens can be readily employed as described herein.

A series of novel protease-activatable bispecific EGFR×CD3 antibodies that demonstrated excellent drug-related properties and potent T cell-mediated killing of EGFR-expressing human colon cancer cells have been generated (U.S. provisional patent application No. 62/783,411). The anti-CD3 antibody used in the previous invention, the humanized OKT3 (hOKT3), does not cross-react with commonly used pharmacologically relevant species such as mice and cynomolgus monkeys. In the present invention, therefore, new bispecific EGFR×CD3 antibodies were designed using engineered humanized SP34 (hSP34) which is cross-reactive against CD3 molecules of humans and several non-human primates such as cynomolgus monkeys.

A new bispecific antibody, termed proBiTE-1s1sp, was generated in which the VH and VL domains of the anti-EGFR antibody SMET5.2 were fused to the N terminus of the VH and VL domains of the anti-CD3 antibody hSP34 Fab via a protease non-cleavable (G4S)3 linker and a protease cleavable linker (SEQ ID NO: 62)
<u>GSGSGRSDNHGGGGS</u>

Figure 40:
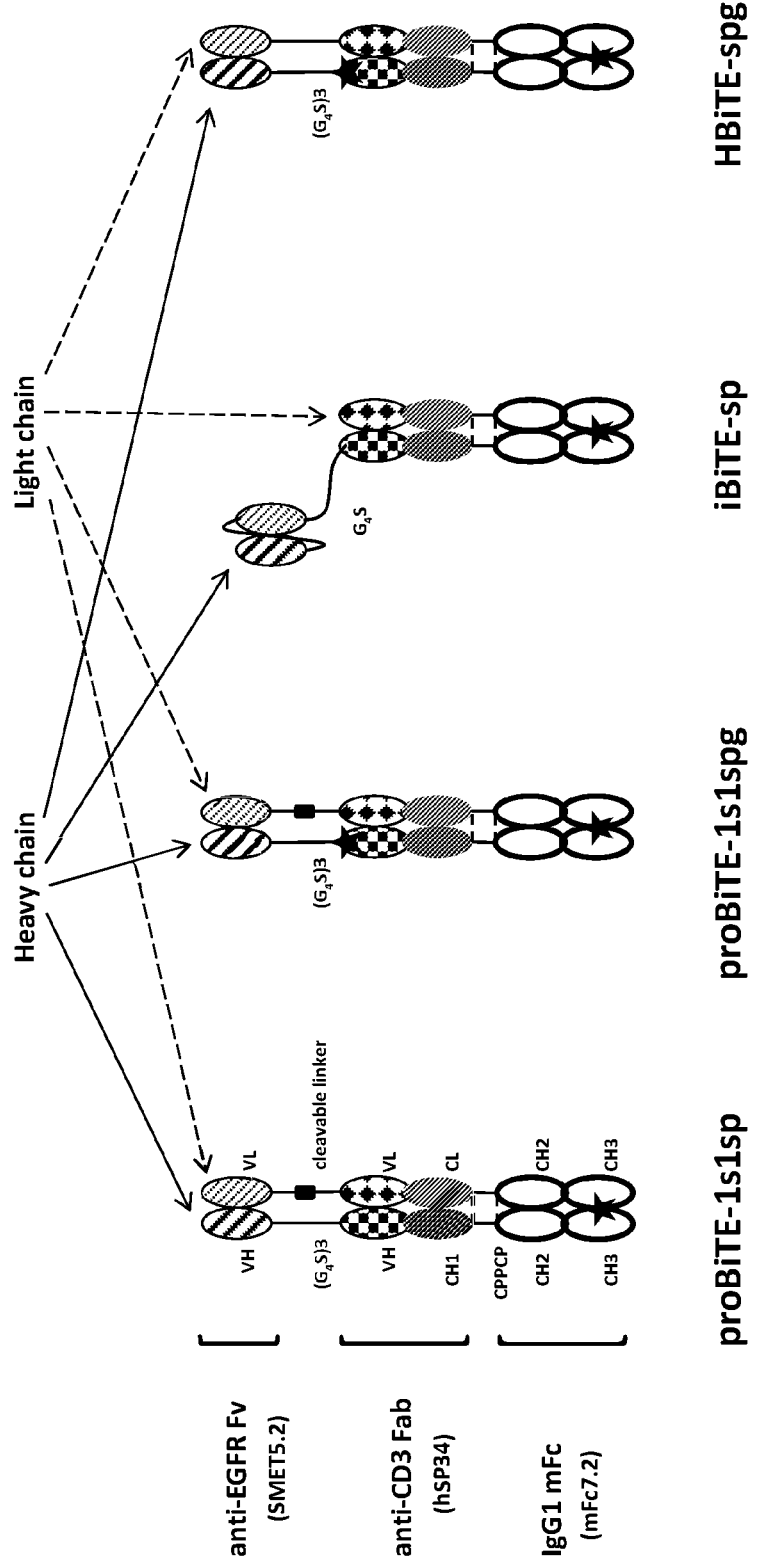
FIG. 40 shows a schematic representation of protease cleavable or non-cleavable bispecific EGFR×CD3 antibodies that have cross-reactive binding to CD3. The star in the IgG1 mFc CH3 domains denotes the T366L and Y407H substitutions. The star in the anti-CD3 VH domain denotes the V105A and N111.1S substitutions.

(underlined is the substrate sequence of uPA, matriptase and legumain), respectively. The anti-CD3 Fab was further fused to the N terminus of a monomeric human IgG1 Fc (mFc7.2) which contains two amino acid mutations (T366L/Y407H) capable of decreasing Fc homodimerization (FIG. 40).

It is well known in the literature that T cells can be efficiently activated by low affinity binding (in the range of 1-90 μM) of T cell receptors (TCR) to peptide-MEC complexes on antigen-presenting cells. It is therefore conceivable that bispecific antibodies binding to the TCR/CD3 complex and a cancer-related antigen might also not need high affinities for efficient activation of T cells. In addition, low affinity binding to CD3 may be advantageous because it will reduce localization of bispecific antibodies to T cells that could potentially cause unwanted side effects. These include, but are not limited to, nonspecific activation of T cells, interference with normal immune responses of T cells, and Fc receptor (FcR)-mediated killing of T cells by other cytotoxic cells such as macrophage and NK cells if bispecific antibodies contain Fc.

In a preliminary experiment, it was found that hSP34 Fab had an affinity for CD3-expressing Jurkat cells of approximately 20 nM. It is believed that the affinity of hSP34 could be further reduced to enlarge therapeutics windows of bispecific antibodies. Analysis of the junction region of hSP34 heavy chain CDR3 (HCDR3) using IMGT/V-QUEST revealed that compared to the closest human antibody germline sequences, there are three amino acid residue mutations, one (A105V) in the V region and two (S111.1N and Y112.2S) in the D region (FIG. 41). It is hypothesized that, due to similar properties of the A and V, and S and N amino acids, reverse mutation of the V105 and N111.1 residues to their germline sequences might retain but reduce binding affinity of hSP34 while potentially minimizing immunogenicity in humans. To test this hypothesis, a new bispecific antibody, designated proBiTE-1s1spg, was generated by introducing the V105A and N111.1S substitutions to the proBiTE-1s1sp construct (FIG. 40). In addition, two amino acid residues in the FR2 of VL were also reverse mutated to their germline sequences (E44Q and F50P, IMGT numbering scheme).

It has been shown that the polypeptide linkers connecting the VH and VL domains of anti-EGFR and anti-CD3 antibodies could decrease binding activity of the anti-CD3 antibody by creating steric hindrance (U.S. provisional patent application No. 62/783,411). To test this possibility with proBiTE-1s1sp and proBiTE-1s1spg, a control construct, iBiTE-sp, was designed in which the scFv of anti-EGFR antibody was fused via the G4S linker to the N terminus of the VH-CH1 of hSP34 and therefore, binding to CD3 is not sterically restricted by the linker (FIG. 40). Another construct, termed HBiTE-spg, was generated by replacing the protease cleavable linker (GSGS-GRSDNHGGGGS (SEQ ID NO:62)) in proBiTE-1s1spg with a protease non-cleavable linker (GSGGGGSGGGGS (SEQ ID NO:127)) (FIG. 40).

Example 15

Generation and Initial Characterization of EGFR×CD3 Bispecific Antibodies with Reduced Binding to CD3

Figure 42:
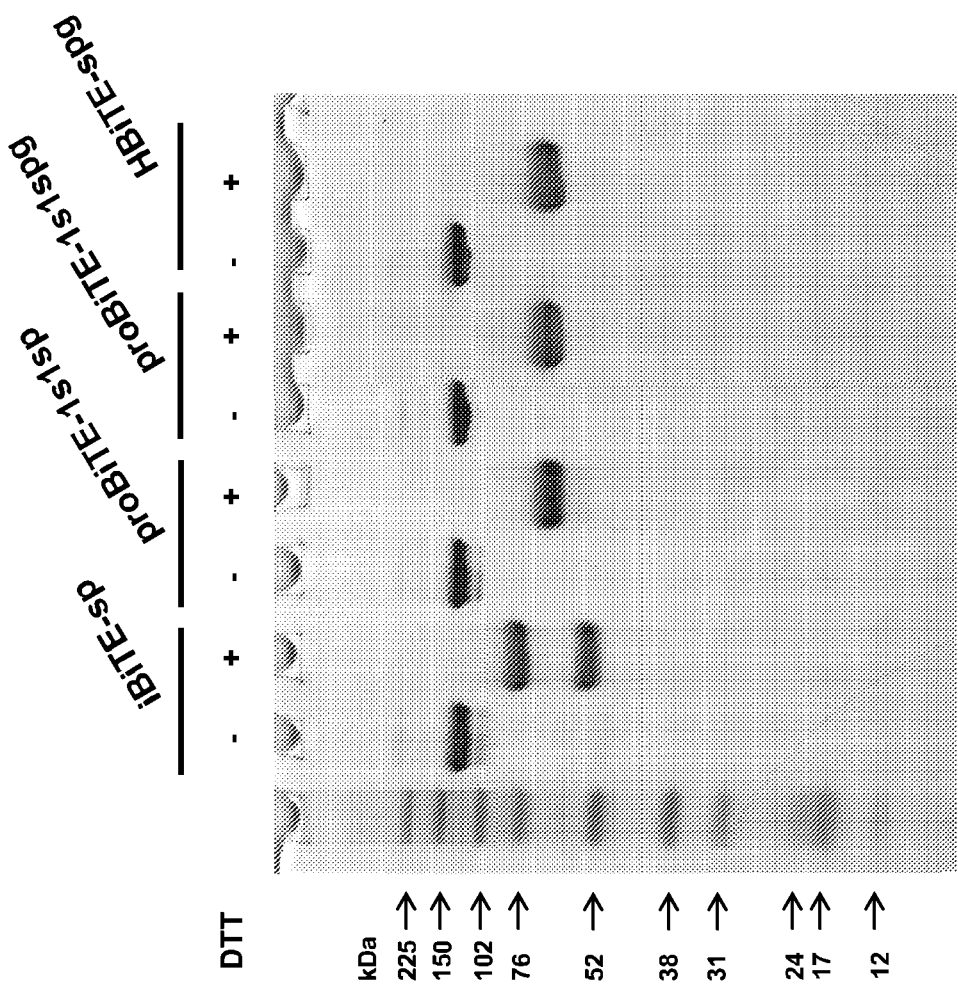
FIG. 42 shows expression and purification of bispecific EGFR×CD3 antibodies. Molecular masses of standards are shown on the left.
Figure 43:
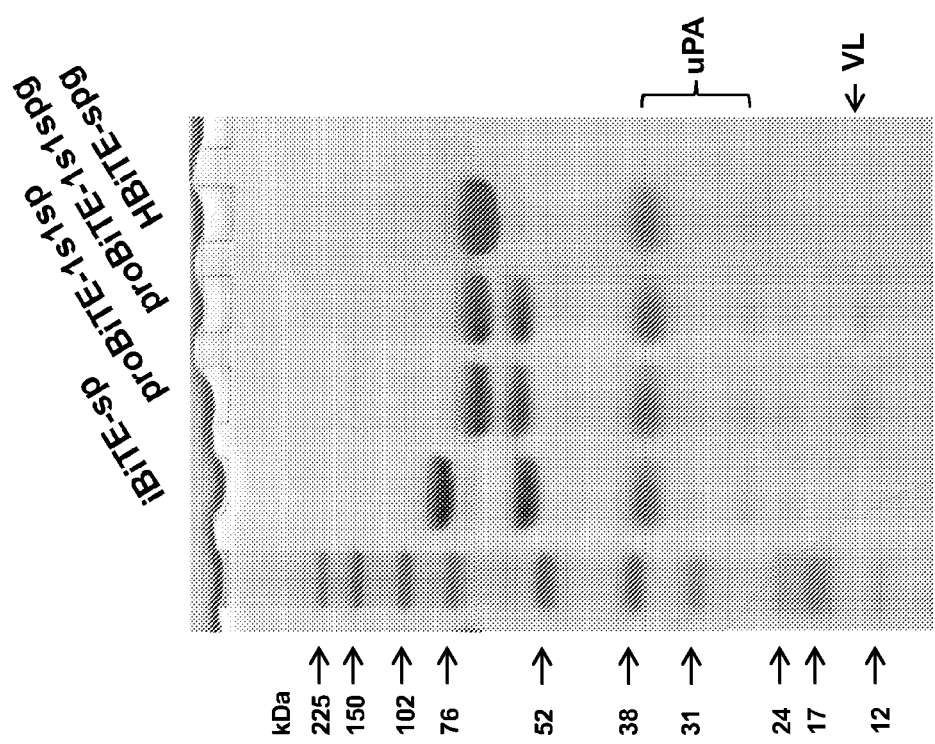
FIG. 43 shows cleavage of bispecific EGFR×CD3 antibodies with tumor-associated protease uPA. Molecular masses of standards are shown on the left. uPA and the isolated VL domain of anti-EGFR antibody are indicated by arrows on the right.
Figure 44:
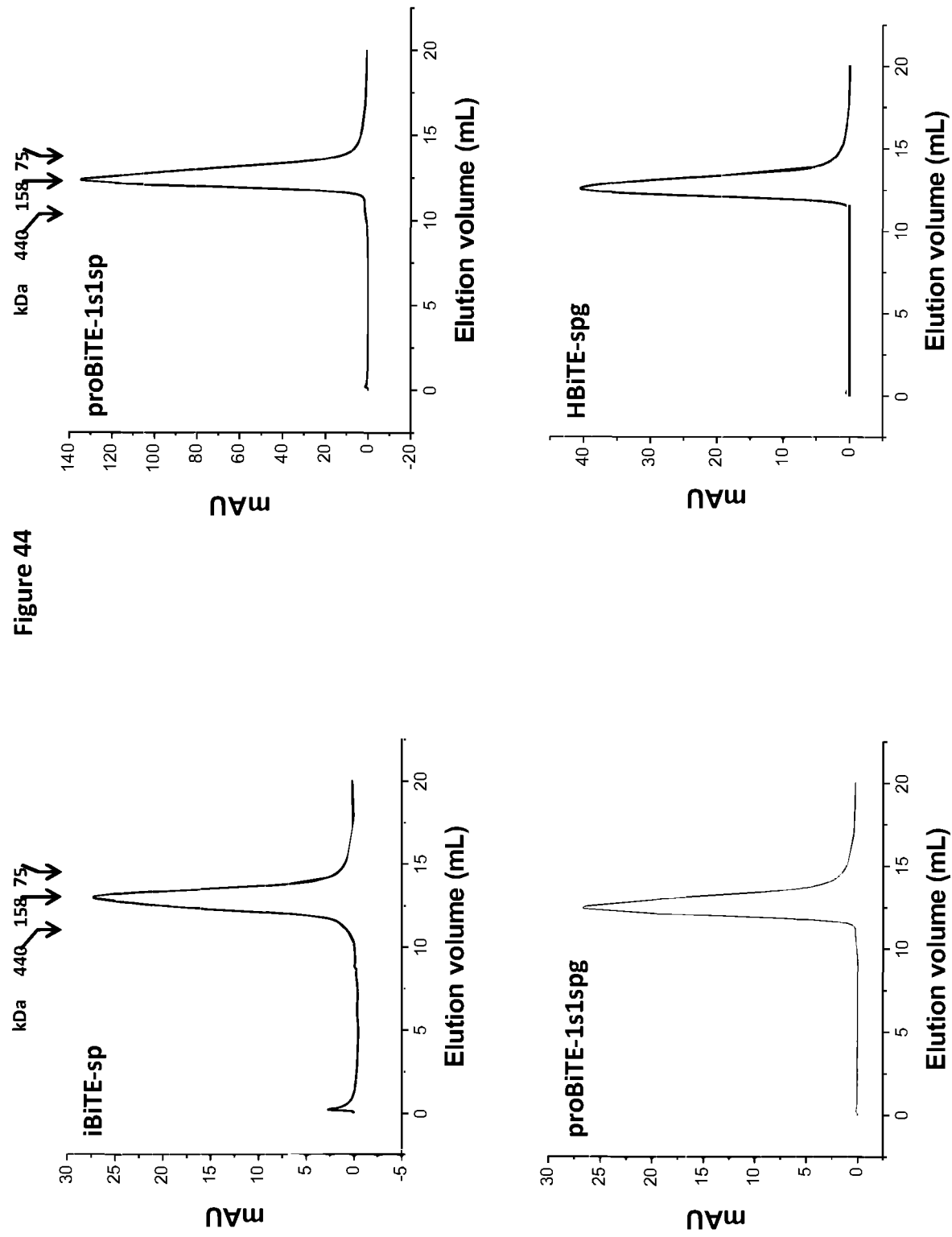
FIG. 44 shows size-exclusion chromatography of the bispecific EGFR×CD3 antibodies. The arrows at the top indicate the elution volumes of the molecular mass standards in PBS (pH7.4): ferritin (440 kDa), aldolase (158 kDa) and conalbumin (75 kDa).

All the bispecific antibodies were well expressed in transiently transfected 293 free style (293FS) cells and secreted into the culture supernatants. On a non-reducing SDS-PAGE, a vast majority of the purified antibodies migrated as a heterodimer with apparent molecular weight (aMW) of approximately 120 kDa (FIG. 42). On a reducing SDS-PAGE, the two polypeptide chains of iBiTE-sp were well separated while those of other bispecific antibodies overlapped with each other with apparent molecular weight (aMW) of approximately 60 kDa.

proBiTE-1s1sp and proBiTE-1s1spg were efficiently cleaved by uPA, resulting in an isolated VL domain of the anti-EGFR antibody while other bispecific antibodies were not sensitive to the protease (FIG. 43). Size-exclusion chromatography analysis showed that the vast majority of purified bispecific antibodies migrated as a monomer with aMW similar to or slightly larger than their calculated molecular weights (cMW) (FIG. 44).

Example 16

Cross-Reactive Binding of Bispecific Antibodies to CD3

Figure 45:
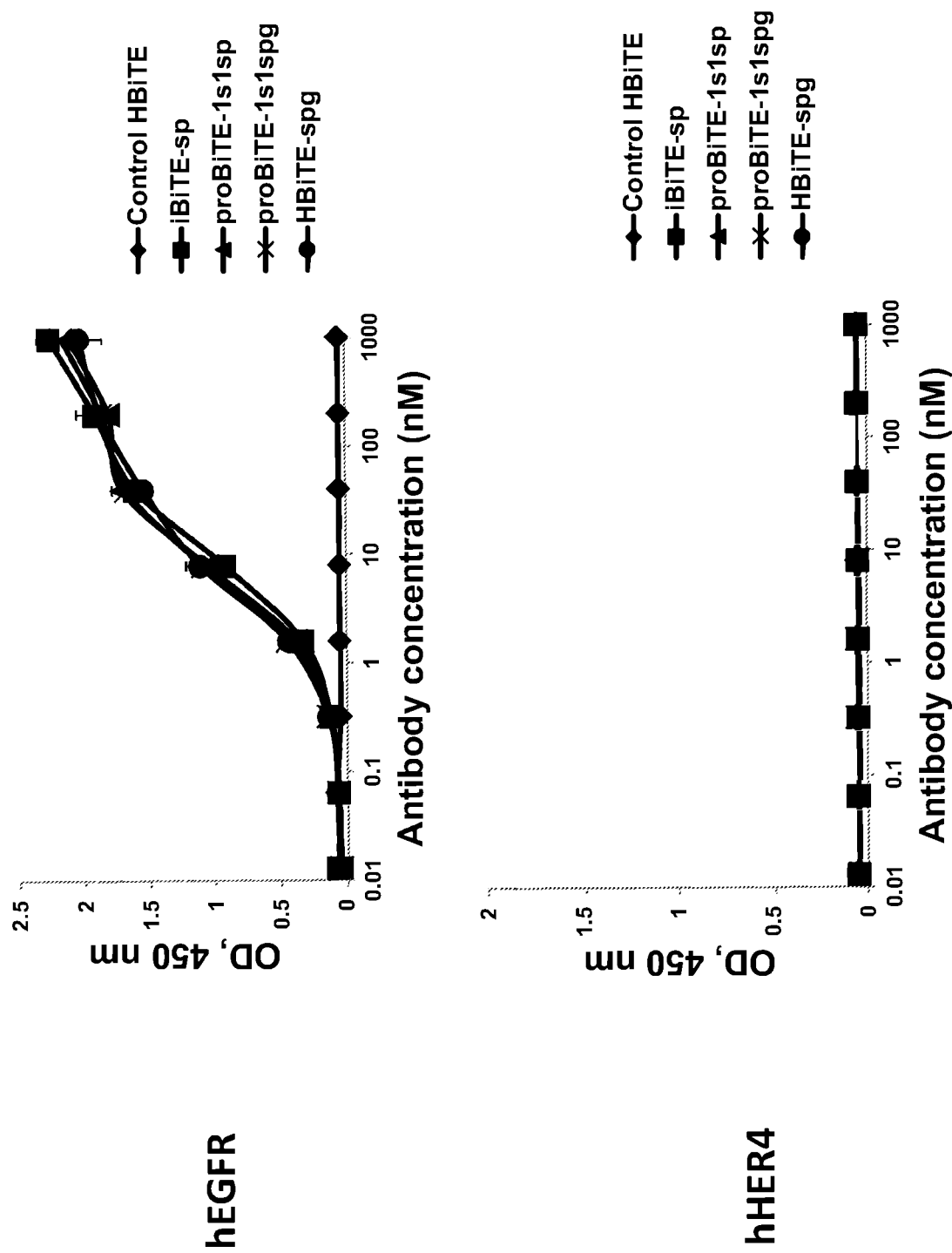
FIG. 45 shows ELISA binding of the bispecific EGFR× CD3 antibodies to recombinant human EGFR (hEGFR) and HER4 (hHER4), an irrelevant antigen.
Figure 46:
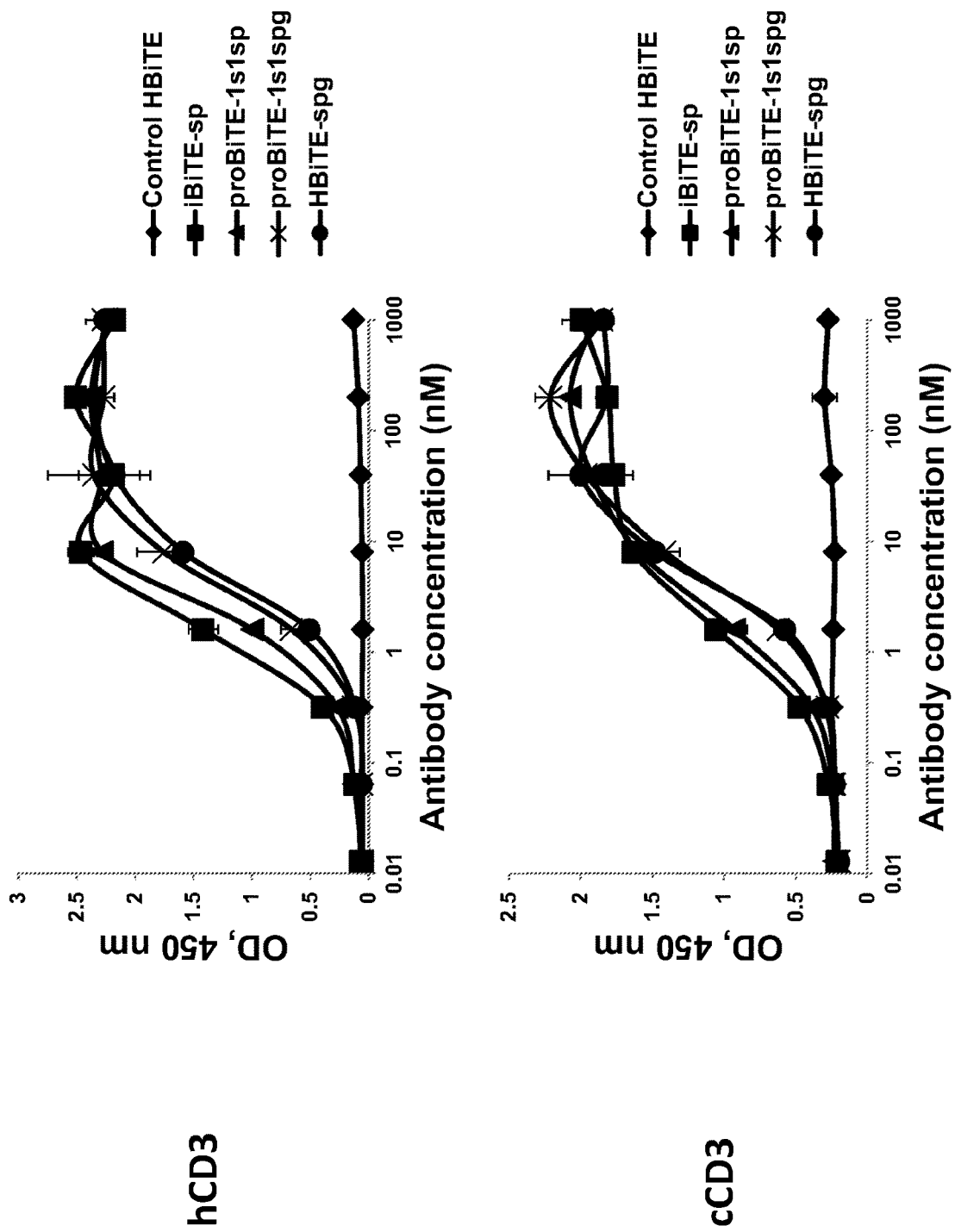
FIG. 46 shows results of ELISA assays demonstrating cross-reactive binding of the bispecific EGFR×CD3 antibodies to recombinant human CD3 (hCD3) and cynomolgus CD3 (cCD3).

ELISA binding of the bispecific antibodies to recombinant human EGFR (hEGFR) and human CD3 (hCD3) and cynomolgus CD3 (cCD3) was first measured. The four bispecific EGFR×CD3 antibodies bound to hEGFR equally well (FIG. 45). None of them interacted with recombinant human HER4 (hHER4), an irrelevant control antigen. They also strongly bound to hCD3 ($EC_{50}$s, 1.3, 1.9, 3.4 and 4.5 nM for iBiTE-sp, proBiTE-1s1sp, proBiTE-1s1spg and HBiTE-spg, respectively) and cCD3 ($EC_{50}$s, 1.6, 2.4, 4.5 and 3.8 nM for iBiTE-sp, proBiTE-1s1sp, proBiTE-1s1spg and HBiTE-spg, respectively) (FIG. 46). A control HBiTE, which is a bispecific FLT3×CD3 antibody, did not interact with hEGFR, hCD3 and cCD3. These results suggest high specificity of the bispecific EGFR×CD3 antibodies.

Figure 47:
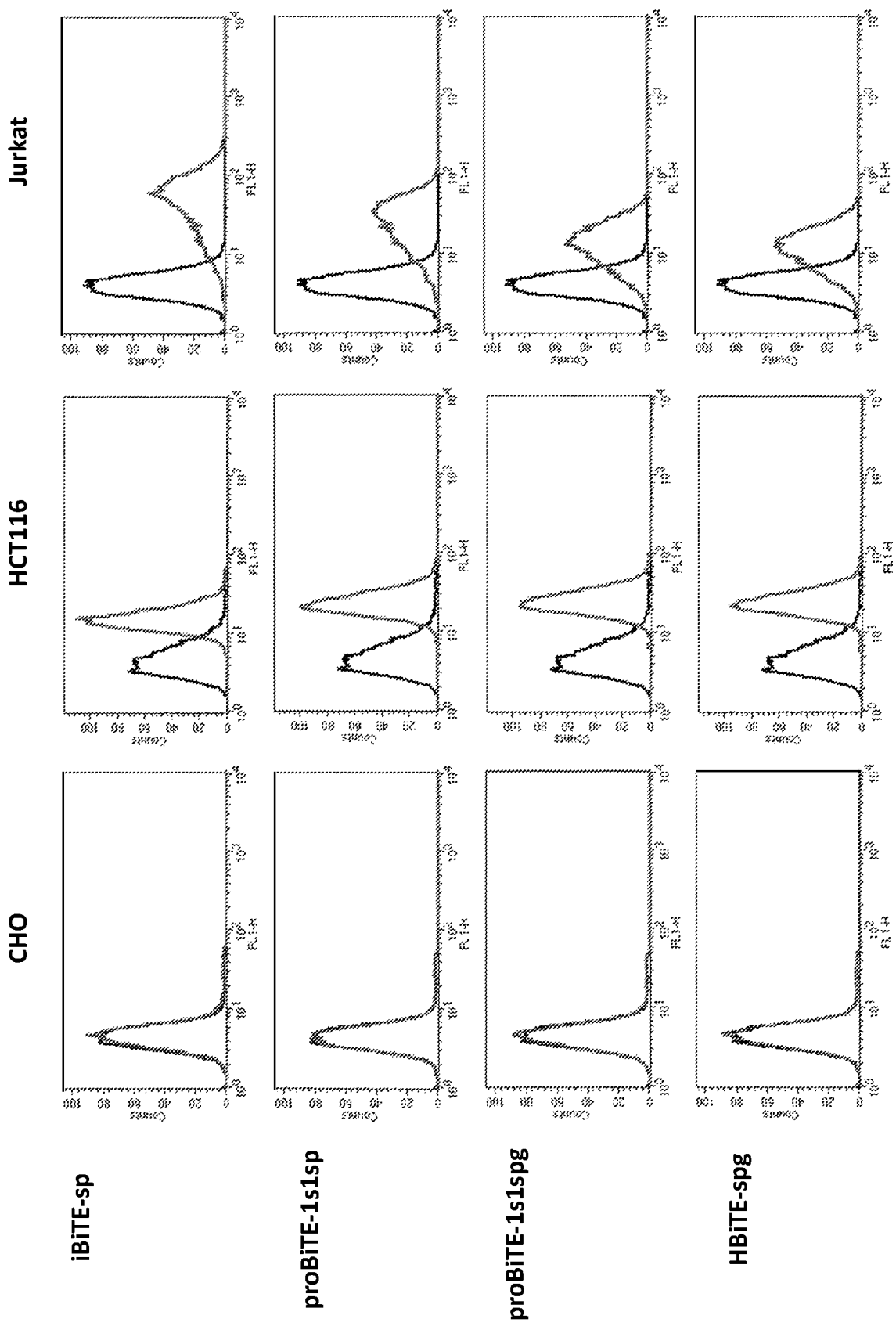
FIG. 47 shows binding of the bispecific EGFR×CD3 antibodies to cell-surface EGFR and CD3 as measured by flow cytometry. The tracing on the left in each diagram represents binding to cells which were incubated only with the secondary antibody, FITC-conjugated anti-human IgG (Fc-specific). The tracing on the right in each diagram represents binding in the experimental groups, in which the cells were first incubated with the bispecific antibodies at a concentration of 2 µg/mL and then with the secondary antibody.

How the bispecific antibodies with different structures and composition of linkers could bind to cell surface EGFR and CD3 was tested next. At a concentration of 2 μg/mL, none of the bispecific antibodies interacted with CHO cells which do not express human EGFR and CD3, while iBiTE-sp bound to both EGFR-expressing HCT116 and CD3-expressing Jurkat cells, suggesting specific binding activity of the anti-EGFR and anti-CD3 antibodies (FIG. 47). proBiTE-1s1sp bound to HCT116 cells as well as iBiTE-sp whereas binding to Jurkat cells was decreased by approximately twofold, suggesting that binding activity of the anti-CD3 antibody hSP34 was only slightly affected by the polypeptide linkers connecting the anti-EGFR and anti-CD3 antibodies. This result is in contrast to the finding in the previous invention that binding activity of the anti-CD3 antibody hOKT3 in proBiTE-1s1 was completely abrogated in the same experimental setting (U.S. provisional patent application No. 62/783,411).

Figure 48:
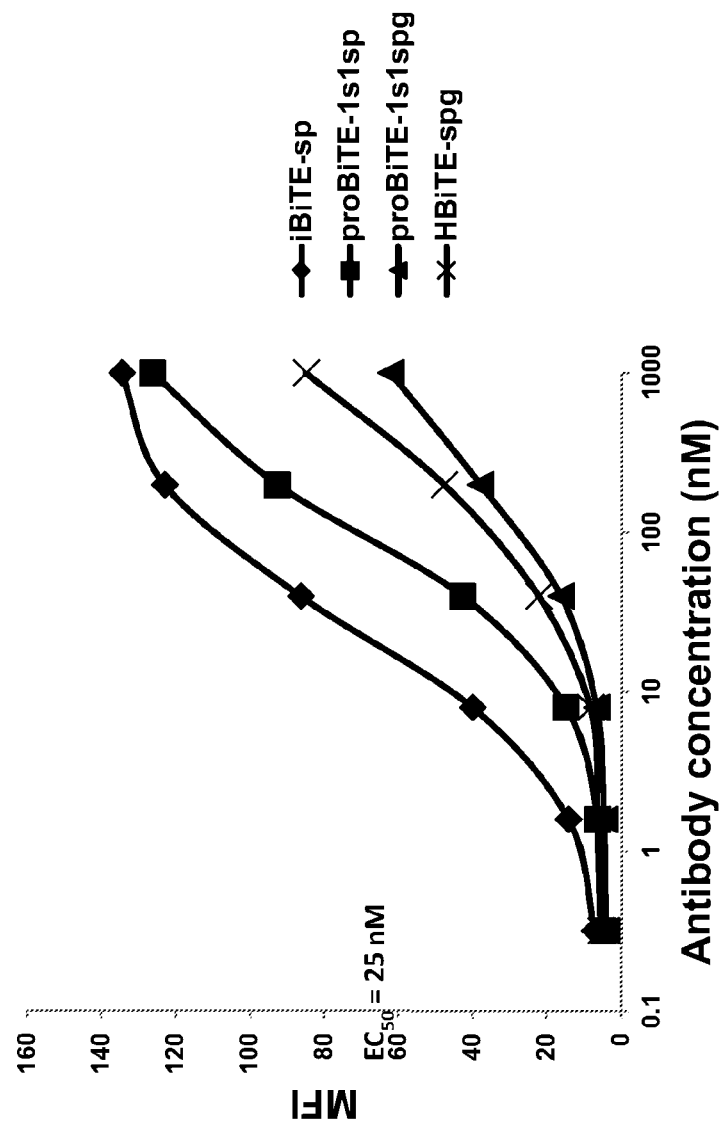
FIG. 48 shows binding of the bispecific EGFR×CD3 antibodies at different concentrations to cell surface CD3 as measured by flow cytometry. The $EC_{50}$ of iBiTE-sp was calculated by fitting the data to the Sigmoidal isotherm.

As expected, reverse mutation of the V105 and N111.1 residues of hSP34 HCDR3 to their germline sequences further decreased binding of proBiTE-1s1spg and HBiTE-spg to Jurkat cells, suggesting that the two substitutions could indeed retain but reduce binding affinity of hSP34. When the bispecific antibodies were tested at different concentrations, iBiTE-sp bound to Jurkat cells with an $EC_{50}$ of 25 nM (FIG. 48). In comparison, binding affinity (EC51, 105 nM) of proBiTE-1s1sp was decreased by approximately fourfold. Binding affinities of proBiTE-1s1spg and HBiTE-spg were further decreased with $EC_{50}$ of >500 nM.

Example 17

Bispecific Antibody-Mediated Killing of Human Colon Cancer Cell Lines

HCT116 and HT29 cells are human colon cancer cell lines with KRAS (G13D) and BRAF (V600E) mutations, respectively. They are not sensitive to the treatment with FDA-approved anti-EGFR monoclonal antibody CETUXIMAB. Therefore, there is an unmet need for novel therapeutic strategies for colorectal cancers with such mutations. HCT116 and HT29 cells are adherent and fibroblastic, and grow in a monolayer in RPMI 1640 medium.

Figure 49:
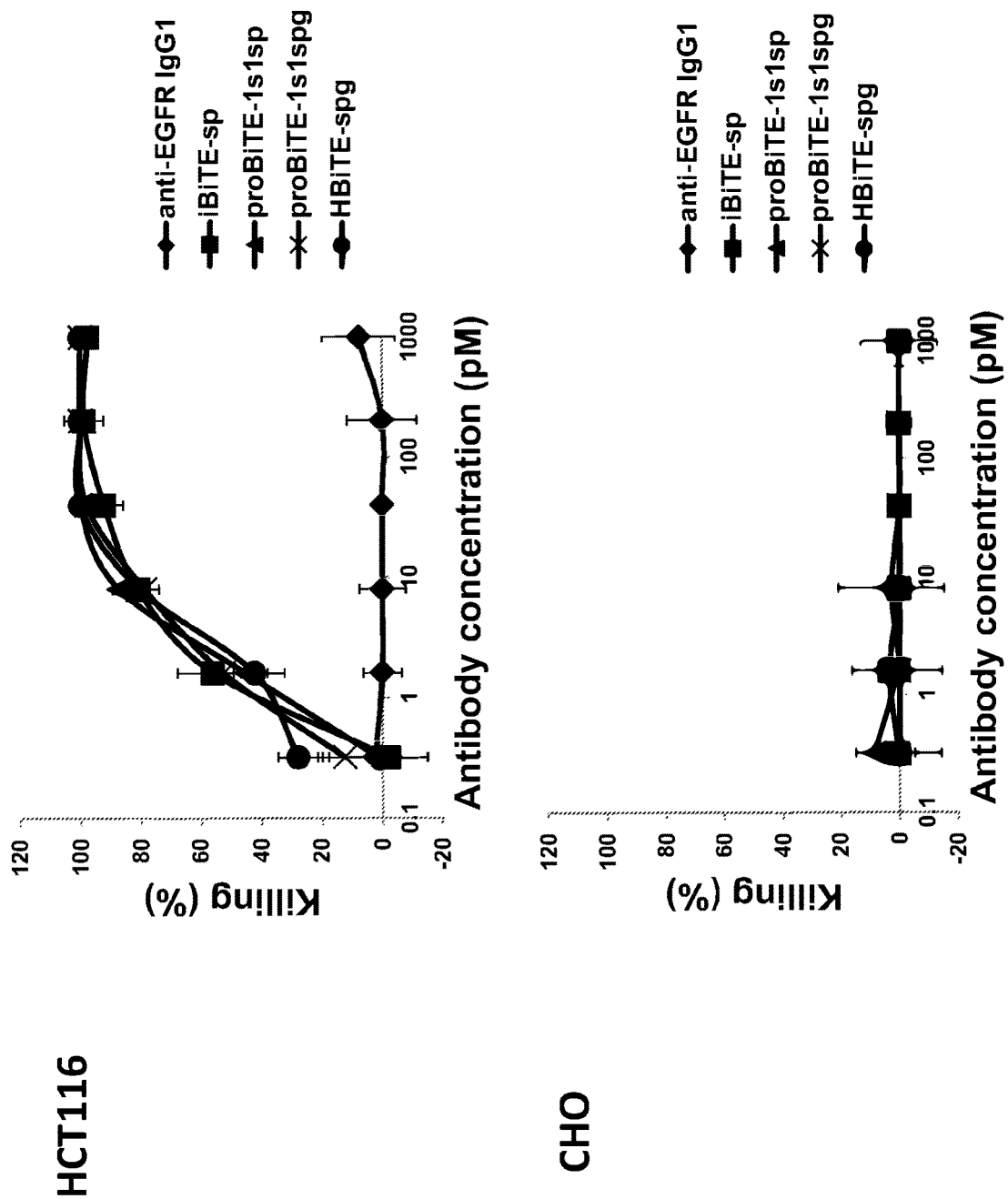
FIG. 49 shows killing of HCT116 and CHO cells infected with Ad5-Luc by the bispecific EGFR×CD3 antibodies in the presence of human PBMC. Target cells and effector cells (PBMC) are at a ratio of 1:2.5. Cell viability was measured after 48 h of incubation using Promega Bright-Glo Luciferase Assay System according to the manufacturer's instructions.

In one killing assay, EGFR-expressing HCT116 and EGFR-negative CHO cells, which were infected with adenovirus type 5 encoding the luciferase reporter gene (Ad5-Luc), were used as target cells. The results showed that although the bispecific antibodies had substantially different binding to CD3-expressing Jurkat cells (FIG. 48), they exhibited comparably potent killing of HCT116 cells with $EC_{50}$ of approximately 1-3 pM (FIG. 49). The anti-EGFR IgG1 antibody did not have an effect on HCT116 cells and none of the antibodies significantly inhibited the growth of CHO cells. These results suggest that indeed, low affinity binding to CD3 (>500 nM, HBiTE-spg) could activate T cells as effectively as high affinity CD3 binding (25 nM, iBiTE-sp).

Figure 50:
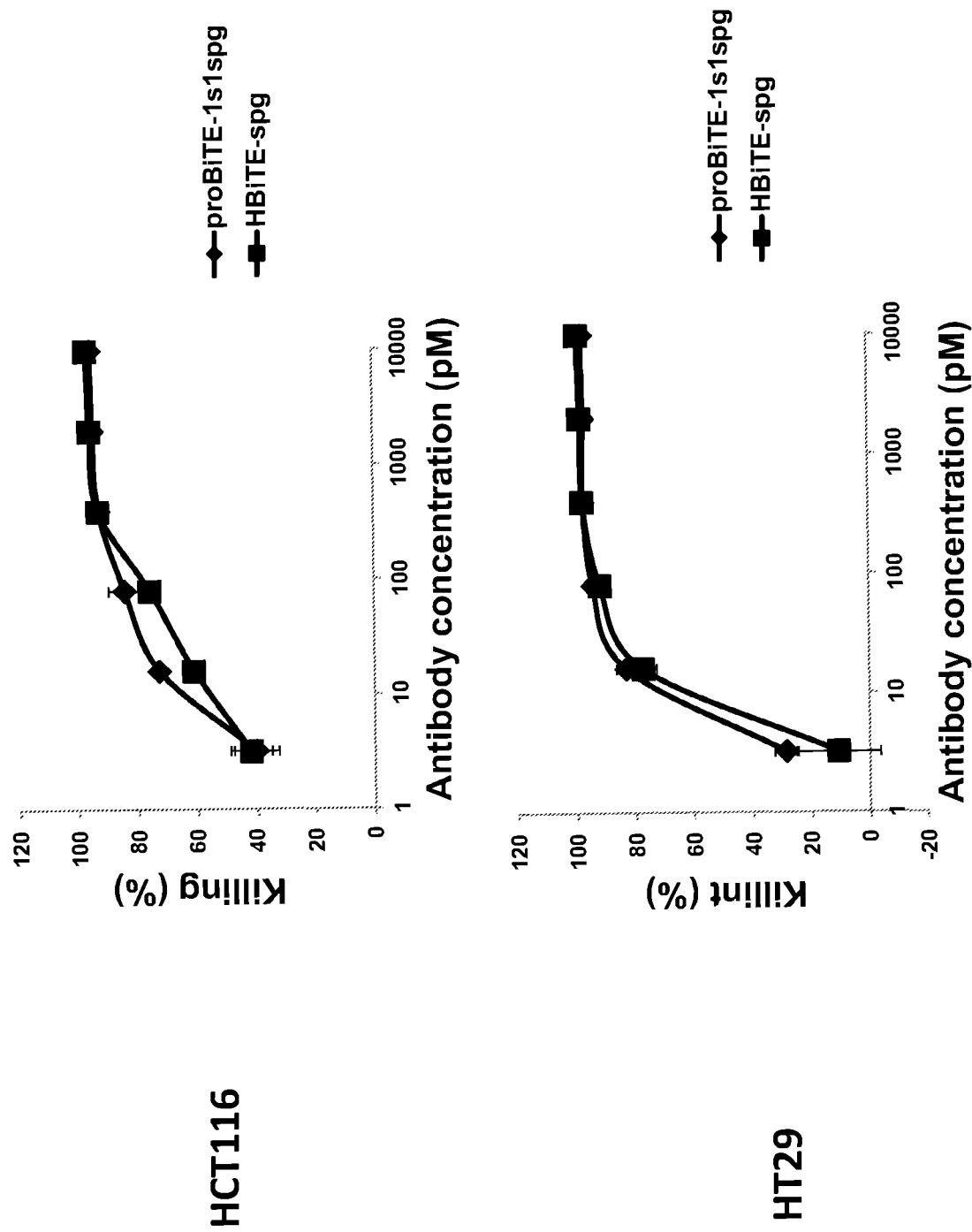
FIG. 50 shows killing of HCT116 and HT29 cells by the bispecific EGFR×CD3 antibodies in the presence of human PBMC. Target cells and effector cells (PBMC) are at a ratio of 1:5. Cell viability was measured after 48 h of incubation using Promega CellTiter 96® $AQ_{ueous}$ One Solution Cell Proliferation Assay according to the manufacturer's instructions.

In another killing assay, MTS tetrazolium compound was used as a reporter reagent. Both proBiTE-spg and HBiTEspg with mutated HCDR3 and light chain FR2 on the anti-CD3 antibody killed HCT116 and HT29 cells with similar efficiency (FIG. 50).

What is claimed is:

1. An isolated anti-human EGFR (epidermal growth factor receptor) antibody, said antibody comprises a heavy chain and a light chain, wherein said heavy chain comprises a complementarity determining region 1 (CDR1) comprising amino acid sequence SEQ ID NO:22, a CDR2 comprising amino acid sequence SEQ ID NO:23, and a CDR3 comprising amino acid sequence SEQ ID NO:24; and wherein said light chain comprises:

a CDR1 comprising amino acid sequence SEQ ID NO:26, a CDR2 comprising amino acid sequence SEQ ID NO:27, and a CDR3 comprising amino acid sequence SEQ ID NO:28;

a CDR1 comprising amino acid sequence SEQ ID NO:31, a CDR2 comprising amino acid sequence SEQ ID NO:32, and a CDR3 comprising amino acid sequence SEQ ID NO:33;

a CDR1 comprising amino acid sequence SEQ ID NO:36, a CDR2 comprising amino acid sequence SEQ ID NO:37, and a CDR3 comprising amino acid sequence SEQ ID NO:38; or a CDR1 comprising amino acid sequence SEQ ID NO:41, a CDR2 comprising amino acid sequence SEQ ID NO:42, and a CDR3 comprising amino acid sequence SEQ ID NO:43.

2. The isolated anti-human EGFR antibody of claim 1, wherein said heavy chain comprises amino acid sequence of SEQ ID NO:21 or SEQ ID NO:44.

3. The isolated anti-human EGFR antibody of claim 1, wherein said light chain comprises amino acid sequence SEQ ID NO:25 or SEQ ID NO:45.

4. The isolated anti-human EGFR antibody of claim 1, wherein said light chain comprises amino acid sequence SEQ ID NO:30 or SEQ ID NO:47.

5. The isolated anti-human EGFR antibody of claim 1, wherein said light chain comprises amino acid sequence SEQ ID NO:35 or SEQ ID NO:49.

6. The isolated anti-human EGFR antibody of claim 1, wherein said light chain comprises amino acid sequence SEQ ID NO:40.

7. A composition comprising a physiologically acceptable carrier and a therapeutically effective amount of the isolated anti-human EGFR antibody of claim 1.

8. A method of treating an EGFR expressing cancer in a subject in need thereof, comprising administering an effective amount of the isolated anti-human EGFR antibody of claim 1 to the subject.

9. The method of claim 8, wherein the cancer is colon cancer.

10. A recombinant bispecific antibody binding to a first antigen on target cells and a second antigen on T cells, wherein the first antigen is EGFR and the second antigen is CD3, and wherein the recombinant bispecific antibody comprises an antigen binding domain of the anti-human EGFR antibody of claim 1, and wherein the recombinant bispecific antibody comprises:
   (a) a heavy chain comprising the amino acid sequence of SEQ ID NO: 50 and a light chain comprising the amino acid sequence of SEQ ID NO: 51;
   (b) a heavy chain comprising the amino acid sequence of SEQ ID NO: 52 and a light chain comprising the amino acid sequence of SEQ ID NO: 53;
   (c) a heavy chain comprising the amino acid sequence of SEQ ID NO: 54 and a light chain comprising the amino acid sequence of SEQ ID NO: 55; or
   (d) a heavy chain comprising the amino acid sequence of SEQ ID NO: 56 and a light chain comprising the amino acid sequence of SEQ ID NO: 57.

11. The recombinant bispecific antibody of claim 10, which is a bispecific T cell engager.

12. A method of treating an EGFR expressing cancer in a subject in need thereof, comprising administering an effective amount of the recombinant bispecific antibody of claim 10 to the subject.

13. The method of claim 12, wherein the cancer is colon cancer.

14. The isolated anti-human EGFR antibody of claim 1, wherein said heavy chain comprises VH domain having amino acid sequence of SEQ ID NO:21, and
   wherein said light chain comprises:
      VL domain having amino acid sequence of SEQ ID NO:25;
      VL domain having amino acid sequence of SEQ ID NO:30;
      VL domain having amino acid sequence of SEQ ID NO:35; or
      VL domain having amino acid sequence of SEQ ID NO:40.

15. The isolated anti-human EGFR antibody of claim 1, wherein said heavy chain comprises amino acid sequence of SEQ ID NO:44, and
   wherein said light chain comprises:
      amino acid sequence of SEQ ID NO:45;
      amino acid sequence of SEQ ID NO:47; or
      amino acid sequence of SEQ ID NO:49.

* * * * *

SEQUENCE LISTING

<160> NUMBER OF SEQ ID NOS: 172

<210> SEQ ID NO 1
<211> LENGTH: 577
<212> TYPE: PRT
<213> ORGANISM: Artificial Sequence
<220> FEATURE:
<223> OTHER INFORMATION: Synthetic--proBiTE-1 Heavy chain

<400> SEQUENCE: 1

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
                165                 170                 175

Lys Gly Leu Glu Trp Ile Gly Tyr Ile Asn Pro Ser Arg Gly Tyr Thr
            180                 185                 190

Asn Tyr Asn Gln Lys Val Lys Asp Arg Phe Thr Ile Ser Thr Asp Lys
        195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys Pro Pro Cys Pro Ala Pro Glu Leu Leu Gly Gly Pro
```

```
                355                 360                 365
Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
            450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
            515                 520                 525

Asp Ser Asp Gly Ser Phe Phe Leu His Ser Lys Leu Thr Val Asp Lys
            530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 2
<211> LENGTH: 561
<212> TYPE: PRT
<213> ORGANISM: Artificial Sequence
<220> FEATURE:
<223> OTHER INFORMATION: Synthetic--proBiTE-1 Light chain

<400> SEQUENCE: 2

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
                20                  25                  30

Leu Ala Trp Tyr Gln Gln Lys Pro Gly Lys Gly Pro Lys Leu Leu Ile
            35                  40                  45

Tyr Ala Thr Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Gly Gly
            100                 105                 110

Gly Ser Leu Ser Gly Arg Ser Asp Asn His Gly Gly Gly Gly Ser Asp
            115                 120                 125

Ile Gln Met Thr Gln Ser Pro Ser Ser Leu Ser Ala Ser Val Gly Asp
        130                 135                 140
```

```
Arg Val Thr Ile Thr Cys Ser Ala Ser Ser Val Ser Tyr Met Asn
145                 150                 155                 160

Trp Tyr Gln Gln Thr Pro Gly Lys Ala Pro Lys Arg Trp Ile Tyr Asp
                165                 170                 175

Thr Ser Lys Leu Ala Ser Gly Val Pro Ser Arg Phe Ser Gly Ser Gly
                180                 185                 190

Ser Gly Thr Asp Tyr Thr Phe Thr Ile Ser Ser Leu Gln Pro Glu Asp
            195                 200                 205

Ile Ala Thr Tyr Tyr Cys Gln Gln Trp Ser Ser Asn Pro Phe Thr Phe
210                 215                 220

Gly Gln Gly Thr Lys Leu Gln Ile Thr Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
                260                 265                 270

Gln Trp Lys Val Asp Asn Ala Leu Gln Ser Gly Asn Ser Gln Glu Ser
            275                 280                 285

Val Thr Glu Gln Asp Ser Lys Asp Ser Thr Tyr Ser Leu Ser Ser Thr
290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys Pro Pro Cys Pro Ala Pro Glu Leu Leu Gly Gly Pro
                340                 345                 350

Ser Val Phe Leu Phe Pro Pro Lys Pro Lys Asp Thr Leu Met Ile Ser
            355                 360                 365

Arg Thr Pro Glu Val Thr Cys Val Val Val Asp Val Ser His Glu Asp
            370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415

Val Ser Val Leu Thr Val Leu His Gln Asp Trp Leu Asn Gly Lys Glu
                420                 425                 430

Tyr Lys Cys Lys Val Ser Asn Lys Ala Leu Pro Ala Pro Ile Glu Lys
            435                 440                 445

Thr Ile Ser Lys Ala Lys Gly Gln Pro Arg Glu Pro Gln Val Tyr Thr
450                 455                 460

Leu Pro Pro Ser Arg Asp Glu Leu Thr Lys Asn Gln Val Ser Leu Leu
465                 470                 475                 480

Cys Leu Val Lys Gly Phe Tyr Pro Ser Asp Ile Ala Val Glu Trp Glu
                485                 490                 495

Ser Asn Gly Gln Pro Glu Asn Asn Tyr Lys Thr Thr Pro Pro Val Leu
                500                 505                 510

Asp Ser Asp Gly Ser Phe Phe Leu His Ser Lys Leu Thr Val Asp Lys
            515                 520                 525

Ser Arg Trp Gln Gln Gly Asn Val Phe Ser Cys Ser Val Met His Glu
            530                 535                 540

Ala Leu His Asn His Tyr Thr Gln Lys Ser Leu Ser Leu Ser Pro Gly
545                 550                 555                 560
```

Lys

<210> SEQ ID NO 3
<211> LENGTH: 577
<212> TYPE: PRT
<213> ORGANISM: Artificial Sequence
<220> FEATURE:
<223> OTHER INFORMATION: Synthetic--proBiTE-2 Heavy chain

<400> SEQUENCE: 3

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Ser Ser Gly Gly Gly Gly
        115                 120                 125

Ser Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
                165                 170                 175

Lys Gly Leu Glu Trp Ile Gly Tyr Ile Asn Pro Ser Arg Gly Tyr Thr
            180                 185                 190

Asn Tyr Asn Gln Lys Val Lys Asp Arg Phe Thr Ile Ser Thr Asp Lys
        195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys Pro Pro Cys Pro Ala Pro Glu Leu Leu Gly Gly Pro

```
            355                 360                 365
Ser Val Phe Leu Phe Pro Pro Lys Pro Lys Asp Thr Leu Met Ile Ser
        370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu His Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 4
<211> LENGTH: 561
<212> TYPE: PRT
<213> ORGANISM: Artificial Sequence
<220> FEATURE:
<223> OTHER INFORMATION: Synthetic--proBiTE-2 Light chain

<400> SEQUENCE: 4

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Gly Gly
            100                 105                 110

Gly Ser Gly Pro Leu Gly Leu Ala Arg Lys Gly Gly Gly Gly Ser Asp
        115                 120                 125

Ile Gln Met Thr Gln Ser Pro Ser Ser Leu Ser Ala Ser Val Gly Asp
    130                 135                 140
```

```
Arg Val Thr Ile Thr Cys Ser Ala Ser Ser Val Ser Tyr Met Asn
145                 150                 155                 160

Trp Tyr Gln Gln Thr Pro Gly Lys Ala Pro Lys Arg Trp Ile Tyr Asp
            165                 170                 175

Thr Ser Lys Leu Ala Ser Gly Val Pro Ser Arg Phe Ser Gly Ser Gly
            180                 185                 190

Ser Gly Thr Asp Tyr Thr Phe Thr Ile Ser Ser Leu Gln Pro Glu Asp
            195                 200                 205

Ile Ala Thr Tyr Tyr Cys Gln Gln Trp Ser Ser Asn Pro Phe Thr Phe
210                 215                 220

Gly Gln Gly Thr Lys Leu Gln Ile Thr Arg Thr Val Ala Ala Pro Ser
225                 230                 235                 240

Val Phe Ile Phe Pro Pro Ser Asp Glu Gln Leu Lys Ser Gly Thr Ala
            245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
            275                 280                 285

Val Thr Glu Gln Asp Ser Lys Asp Ser Thr Tyr Ser Leu Ser Ser Thr
290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
            325                 330                 335

Arg Gly Glu Cys Pro Pro Cys Pro Ala Pro Glu Leu Leu Gly Gly Pro
            340                 345                 350

Ser Val Phe Leu Phe Pro Pro Lys Pro Lys Asp Thr Leu Met Ile Ser
            355                 360                 365

Arg Thr Pro Glu Val Thr Cys Val Val Val Asp Val Ser His Glu Asp
            370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
            405                 410                 415

Val Ser Val Leu Thr Val Leu His Gln Asp Trp Leu Asn Gly Lys Glu
            420                 425                 430

Tyr Lys Cys Lys Val Ser Asn Lys Ala Leu Pro Ala Pro Ile Glu Lys
            435                 440                 445

Thr Ile Ser Lys Ala Lys Gly Gln Pro Arg Glu Pro Gln Val Tyr Thr
            450                 455                 460

Leu Pro Pro Ser Arg Asp Glu Leu Thr Lys Asn Gln Val Ser Leu Leu
465                 470                 475                 480

Cys Leu Val Lys Gly Phe Tyr Pro Ser Asp Ile Ala Val Glu Trp Glu
            485                 490                 495

Ser Asn Gly Gln Pro Glu Asn Asn Tyr Lys Thr Thr Pro Pro Val Leu
            500                 505                 510

Asp Ser Asp Gly Ser Phe Phe Leu His Ser Lys Leu Thr Val Asp Lys
            515                 520                 525

Ser Arg Trp Gln Gln Gly Asn Val Phe Ser Cys Ser Val Met His Glu
            530                 535                 540

Ala Leu His Asn His Tyr Thr Gln Lys Ser Leu Ser Leu Ser Pro Gly
545                 550                 555                 560
```

Lys

<210> SEQ ID NO 5
<211> LENGTH: 577
<212> TYPE: PRT
<213> ORGANISM: Artificial Sequence
<220> FEATURE:
<223> OTHER INFORMATION: Synthetic--proBiTE-12 Heavy chain

<400> SEQUENCE: 5

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Ser Ser Gly Gly Gly Gly
        115                 120                 125

Ser Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
                165                 170                 175

Lys Gly Leu Glu Trp Ile Gly Tyr Ile Asn Pro Ser Arg Gly Tyr Thr
            180                 185                 190

Asn Tyr Asn Gln Lys Val Lys Asp Arg Phe Thr Ile Ser Thr Asp Lys
        195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys Pro Pro Cys Pro Ala Pro Glu Leu Leu Gly Gly Pro
```

```
                355                 360                 365
Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
        450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu His Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 6
<211> LENGTH: 564
<212> TYPE: PRT
<213> ORGANISM: Artificial Sequence
<220> FEATURE:
<223> OTHER INFORMATION: Synthetic--proBiTE-12 Light chain

<400> SEQUENCE: 6

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Gly Gly
            100                 105                 110

Gly Ser Leu Ser Gly Arg Ser Asp Asn His Gly Pro Leu Gly Leu Ala
        115                 120                 125

Arg Lys Asp Ile Gln Met Thr Gln Ser Pro Ser Ser Leu Ser Ala Ser
    130                 135                 140
```

```
Val Gly Asp Arg Val Thr Ile Thr Cys Ser Ala Ser Ser Val Ser
145                 150                 155                 160

Tyr Met Asn Trp Tyr Gln Gln Thr Pro Gly Lys Ala Pro Lys Arg Trp
            165                 170                 175

Ile Tyr Asp Thr Ser Lys Leu Ala Ser Gly Val Pro Ser Arg Phe Ser
            180                 185                 190

Gly Ser Gly Ser Gly Thr Asp Tyr Thr Phe Thr Ile Ser Ser Leu Gln
            195                 200                 205

Pro Glu Asp Ile Ala Thr Tyr Tyr Cys Gln Gln Trp Ser Ser Asn Pro
            210                 215                 220

Phe Thr Phe Gly Gln Gly Thr Lys Leu Gln Ile Thr Arg Thr Val Ala
225                 230                 235                 240

Ala Pro Ser Val Phe Ile Phe Pro Pro Ser Asp Glu Gln Leu Lys Ser
            245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
            275                 280                 285

Gln Glu Ser Val Thr Glu Gln Asp Ser Lys Asp Ser Thr Tyr Ser Leu
            290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
            325                 330                 335

Ser Phe Asn Arg Gly Glu Cys Pro Pro Cys Pro Ala Pro Glu Leu Leu
            340                 345                 350

Gly Gly Pro Ser Val Phe Leu Phe Pro Pro Lys Pro Lys Asp Thr Leu
            355                 360                 365

Met Ile Ser Arg Thr Pro Glu Val Thr Cys Val Val Val Asp Val Ser
370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
            405                 410                 415

Tyr Arg Val Val Ser Val Leu Thr Val Leu His Gln Asp Trp Leu Asn
            420                 425                 430

Gly Lys Glu Tyr Lys Cys Lys Val Ser Asn Lys Ala Leu Pro Ala Pro
            435                 440                 445

Ile Glu Lys Thr Ile Ser Lys Ala Lys Gly Gln Pro Arg Glu Pro Gln
            450                 455                 460

Val Tyr Thr Leu Pro Pro Ser Arg Asp Glu Leu Thr Lys Asn Gln Val
465                 470                 475                 480

Ser Leu Leu Cys Leu Val Lys Gly Phe Tyr Pro Ser Asp Ile Ala Val
            485                 490                 495

Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu His Ser Lys Leu Thr
            515                 520                 525

Val Asp Lys Ser Arg Trp Gln Gln Gly Asn Val Phe Ser Cys Ser Val
            530                 535                 540

Met His Glu Ala Leu His Asn His Tyr Thr Gln Lys Ser Leu Ser Leu
545                 550                 555                 560
```

Ser Pro Gly Lys

<210> SEQ ID NO 7
<211> LENGTH: 701
<212> TYPE: PRT
<213> ORGANISM: Artificial Sequence
<220> FEATURE:
<223> OTHER INFORMATION: Synthetic--iBiTE Heavy chain

<400> SEQUENCE: 7

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Val Val Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Met Ser Arg Trp Leu Ala Trp Tyr Gln Gln Lys Pro Gly Lys
                165                 170                 175

Gly Pro Lys Leu Leu Ile Tyr Ala Thr Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

Leu Asp Ser Phe Pro Phe Ser Phe Thr Phe Gly Pro Gly Thr Lys Val
225                 230                 235                 240

Asp Leu Lys Gly Gly Gly Ser Gly Gly Gly Gly Ser Gly Gly Gly Gly
                245                 250                 255

Gly Ser Gln Val Gln Leu Val Gln Ser Gly Gly Gly Val Val Gln Pro
            260                 265                 270

Gly Arg Ser Leu Arg Leu Ser Cys Lys Ala Ser Gly Tyr Thr Phe Thr
        275                 280                 285

Arg Tyr Thr Met His Trp Val Arg Gln Ala Pro Gly Lys Gly Leu Glu
    290                 295                 300

Trp Ile Gly Tyr Ile Asn Pro Ser Arg Gly Tyr Thr Asn Tyr Asn Gln
305                 310                 315                 320

Lys Val Lys Asp Arg Phe Thr Ile Ser Thr Asp Lys Ser Lys Ser Thr
                325                 330                 335

Ala Phe Leu Gln Met Asp Ser Leu Arg Pro Glu Asp Thr Ala Val Tyr
            340                 345                 350

Tyr Cys Ala Arg Tyr Tyr Asp Asp His Tyr Ser Leu Asp Tyr Trp Gly
```

```
                    355                 360                 365
Gln Gly Thr Thr Leu Thr Val Ser Ser Ala Ser Thr Lys Gly Pro Ser
            370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
            435                 440                 445

Pro Ser Ser Ser Leu Gly Thr Gln Thr Tyr Ile Cys Asn Val Asn His
            450                 455                 460

Lys Pro Ser Asn Thr Lys Val Asp Lys Lys Val Glu Pro Lys Ser Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
            595                 600                 605

Arg Asp Glu Leu Thr Lys Asn Gln Val Ser Leu Leu Cys Leu Val Lys
610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu His Ser Lys Leu Thr Val Asp Lys Ser Arg Trp Gln
            660                 665                 670

Gln Gly Asn Val Phe Ser Cys Ser Val Met His Glu Ala Leu His Asn
            675                 680                 685

His Tyr Thr Gln Lys Ser Leu Ser Leu Ser Pro Gly Lys
            690                 695                 700

<210> SEQ ID NO 8
<211> LENGTH: 434
<212> TYPE: PRT
<213> ORGANISM: Artificial Sequence
<220> FEATURE:
<223> OTHER INFORMATION: Synthetic--iBiTE Light chain

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
```

-continued

```
                20                  25                  30
Asn Trp Tyr Gln Gln Thr Pro Gly Lys Ala Pro Lys Arg Trp Ile Tyr
            35                  40                  45
Asp Thr Ser Lys Leu Ala Ser Gly Val Pro Ser Arg Phe Ser Gly Ser
        50                  55                  60
Gly Ser Gly Thr Asp Tyr Thr Phe Thr Ile Ser Ser Leu Gln Pro Glu
65                  70                  75                  80
Asp Ile Ala Thr Tyr Tyr Cys Gln Gln Trp Ser Ser Asn Pro Phe Thr
                85                  90                  95
Phe Gly Gln Gly Thr Lys Leu Gln Ile Thr Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys Pro Pro Cys Pro Ala Pro Glu Leu Leu Gly Gly
    210                 215                 220
Pro Ser Val Phe Leu Phe Pro Pro Lys Pro Lys Asp Thr Leu Met Ile
225                 230                 235                 240
Ser Arg Thr Pro Glu Val Thr Cys Val Val Val Asp Val Ser His Glu
                245                 250                 255
Asp Pro Glu Val Lys Phe Asn Trp Tyr Val Asp Gly Val Glu Val His
            260                 265                 270
Asn Ala Lys Thr Lys Pro Arg Glu Glu Gln Tyr Asn Ser Thr Tyr Arg
        275                 280                 285
Val Val Ser Val Leu Thr Val Leu His Gln Asp Trp Leu Asn Gly Lys
    290                 295                 300
Glu Tyr Lys Cys Lys Val Ser Asn Lys Ala Leu Pro Ala Pro Ile Glu
305                 310                 315                 320
Lys Thr Ile Ser Lys Ala Lys Gly Gln Pro Arg Glu Pro Gln Val Tyr
                325                 330                 335
Thr Leu Pro Pro Ser Arg Asp Glu Leu Thr Lys Asn Gln Val Ser Leu
            340                 345                 350
Leu Cys Leu Val Lys Gly Phe Tyr Pro Ser Asp Ile Ala Val Glu Trp
        355                 360                 365
Glu Ser Asn Gly Gln Pro Glu Asn Asn Tyr Lys Thr Thr Pro Pro Val
    370                 375                 380
Leu Asp Ser Asp Gly Ser Phe Phe Leu His Ser Lys Leu Thr Val Asp
385                 390                 395                 400
Lys Ser Arg Trp Gln Gln Gly Asn Val Phe Ser Cys Ser Val Met His
                405                 410                 415
Glu Ala Leu His Asn His Tyr Thr Gln Lys Ser Leu Ser Leu Ser Pro
            420                 425                 430
Gly Lys
```

-continued

```
<210> SEQ ID NO 9
<211> LENGTH: 577
<212> TYPE: PRT
<213> ORGANISM: Artificial Sequence
<220> FEATURE:
<223> OTHER INFORMATION: Synthetic--HBiTE Heavy chain

<400> SEQUENCE: 9

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
                165                 170                 175

Lys Gly Leu Glu Trp Ile Gly Tyr Ile Asn Pro Ser Arg Gly Tyr Thr
            180                 185                 190

Asn Tyr Asn Gln Lys Val Lys Asp Arg Phe Thr Ile Ser Thr Asp Lys
        195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys Pro Pro Cys Pro Ala Pro Glu Leu Leu Gly Gly Pro
        355                 360                 365
```

```
Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
                420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
                485                 490                 495

Cys Leu Val Lys Gly Phe Tyr Pro Ser Asp Ile Ala Val Glu Trp Glu
                500                 505                 510

Ser Asn Gly Gln Pro Glu Asn Asn Tyr Lys Thr Thr Pro Pro Val Leu
            515                 520                 525

Asp Ser Asp Gly Ser Phe Phe Leu His Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 10
<211> LENGTH: 558
<212> TYPE: PRT
<213> ORGANISM: Artificial Sequence
<220> FEATURE:
<223> OTHER INFORMATION: Synthetic--HBiTE Light chain

<400> SEQUENCE: 10

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
                20                  25                  30

Leu Ala Trp Tyr Gln Gln Lys Pro Gly Lys Pro Lys Leu Leu Ile
            35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Gly Gly
                100                 105                 110

Gly Ser Gly Gly Gly Gly Ser Gly Gly Gly Ser Asp Ile Gln Met
            115                 120                 125

Thr Gln Ser Pro Ser Ser Leu Ser Ala Ser Val Gly Asp Arg Val Thr
    130                 135                 140

Ile Thr Cys Ser Ala Ser Ser Ser Val Ser Tyr Met Asn Trp Tyr Gln
```

-continued

```
            145                 150                 155                 160
        Gln Thr Pro Gly Lys Ala Pro Lys Arg Trp Ile Tyr Asp Thr Ser Lys
                        165                 170                 175
        Leu Ala Ser Gly Val Pro Ser Arg Phe Ser Gly Ser Gly Ser Gly Thr
                        180                 185                 190
        Asp Tyr Thr Phe Thr Ile Ser Leu Gln Pro Glu Asp Ile Ala Thr
                        195                 200                 205
        Tyr Tyr Cys Gln Gln Trp Ser Ser Asn Pro Phe Thr Phe Gly Gln Gly
                210                 215                 220
        Thr Lys Leu Gln Ile Thr Arg Thr Val Ala Ala Pro Ser Val Phe Ile
        225                 230                 235                 240
        Phe Pro Pro Ser Asp Glu Gln Leu Lys Ser Gly Thr Ala Ser Val Val
                            245                 250                 255
        Cys Leu Leu Asn Asn Phe Tyr Pro Arg Glu Ala Lys Val Gln Trp Lys
                        260                 265                 270
        Val Asp Asn Ala Leu Gln Ser Gly Asn Ser Gln Glu Ser Val Thr Glu
                    275                 280                 285
        Gln Asp Ser Lys Asp Ser Thr Tyr Ser Leu Ser Ser Thr Leu Thr Leu
                290                 295                 300
        Ser Lys Ala Asp Tyr Glu Lys His Lys Val Tyr Ala Cys Glu Val Thr
        305                 310                 315                 320
        His Gln Gly Leu Ser Ser Pro Val Thr Lys Ser Phe Asn Arg Gly Glu
                            325                 330                 335
        Cys Pro Pro Cys Pro Ala Pro Glu Leu Leu Gly Gly Pro Ser Val Phe
                        340                 345                 350
        Leu Phe Pro Pro Lys Pro Lys Asp Thr Leu Met Ile Ser Arg Thr Pro
                    355                 360                 365
        Glu Val Thr Cys Val Val Val Asp Val Ser His Glu Asp Pro Glu Val
                370                 375                 380
        Lys Phe Asn Trp Tyr Val Asp Gly Val Glu Val His Asn Ala Lys Thr
        385                 390                 395                 400
        Lys Pro Arg Glu Glu Gln Tyr Asn Ser Thr Tyr Arg Val Val Ser Val
                            405                 410                 415
        Leu Thr Val Leu His Gln Asp Trp Leu Asn Gly Lys Glu Tyr Lys Cys
                        420                 425                 430
        Lys Val Ser Asn Lys Ala Leu Pro Ala Pro Ile Glu Lys Thr Ile Ser
                    435                 440                 445
        Lys Ala Lys Gly Gln Pro Arg Glu Pro Gln Val Tyr Thr Leu Pro Pro
                450                 455                 460
        Ser Arg Asp Glu Leu Thr Lys Asn Gln Val Ser Leu Leu Cys Leu Val
        465                 470                 475                 480
        Lys Gly Phe Tyr Pro Ser Asp Ile Ala Val Glu Trp Glu Ser Asn Gly
                            485                 490                 495
        Gln Pro Glu Asn Asn Tyr Lys Thr Thr Pro Pro Val Leu Asp Ser Asp
                        500                 505                 510
        Gly Ser Phe Phe Leu His Ser Lys Leu Thr Val Asp Lys Ser Arg Trp
                    515                 520                 525
        Gln Gln Gly Asn Val Phe Ser Cys Ser Val Met His Glu Ala Leu His
                530                 535                 540
        Asn His Tyr Thr Gln Lys Ser Leu Ser Leu Ser Pro Gly Lys
        545                 550                 555

<210> SEQ ID NO 11
```

```
<211> LENGTH: 577
<212> TYPE: PRT
<213> ORGANISM: Artificial Sequence
<220> FEATURE:
<223> OTHER INFORMATION: Synthetic--proBiTE-1s Heavy chain

<400> SEQUENCE: 11
```

| | | | | | | | | | | | | | | |
|---|---|---|---|---|---|---|---|---|---|---|---|---|---|---|
| Glu | Val | Gln | Leu | Val | Glu | Thr | Gly | Gly | Gly | Val | Val | Gln | Pro | Gly | Arg |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | |
| Ala | Met | His | Trp | Val | Arg | Gln | Ala | Pro | Gly | Lys | Gly | Leu | Glu | Trp | Val |
| | | 35 | | | | | 40 | | | | | 45 | | |
| Ala | Val | Ile | Ser | Tyr | Asp | Gly | Ser | Asn | Lys | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Gly | Tyr | Val | Ala | Arg | Gly | Asp | Phe | Asp | Tyr | Trp | Gly | Gln | Gly |
| | | | 100 | | | | | 105 | | | | | 110 | | |
| Thr | Leu | Val | Thr | Val | Ser | Ser | Gly | Gly | Gly | Ser | Gly | Gly | Gly | Gly |
| | | 115 | | | | | 120 | | | | | 125 | | |
| Ser | Gly | Gly | Gly | Ser | Gln | Val | Gln | Leu | Val | Gln | Ser | Gly | Gly | Gly |
| | 130 | | | | | 135 | | | | | 140 | | | | |
| Val | Val | Gln | Pro | Gly | Arg | Ser | Leu | Arg | Leu | Ser | Cys | Lys | Ala | Ser | Gly |
| 145 | | | | | 150 | | | | | 155 | | | | | 160 |
| Tyr | Thr | Phe | Thr | Arg | Tyr | Thr | Met | His | Trp | Val | Arg | Gln | Ala | Pro | Gly |
| | | | | 165 | | | | | 170 | | | | | 175 | |
| Lys | Gly | Leu | Glu | Trp | Ile | Gly | Tyr | Ile | Asn | Pro | Ser | Arg | Gly | Tyr | Thr |
| | | | 180 | | | | | 185 | | | | | 190 | | |
| Asn | Tyr | Asn | Gln | Lys | Val | Lys | Asp | Arg | Phe | Thr | Ile | Ser | Thr | Asp | Lys |
| | | 195 | | | | | 200 | | | | | 205 | | | |
| Ser | Lys | Ser | Thr | Ala | Phe | Leu | Gln | Met | Asp | Ser | Leu | Arg | Pro | Glu | Asp |
| | 210 | | | | | 215 | | | | | 220 | | | | |
| Thr | Ala | Val | Tyr | Tyr | Cys | Ala | Arg | Tyr | Tyr | Asp | Asp | His | Tyr | Ser | Leu |
| 225 | | | | | 230 | | | | | 235 | | | | | 240 |
| Asp | Tyr | Trp | Gly | Gln | Gly | Thr | Thr | Leu | Thr | Val | Ser | Ser | Ala | Ser | Thr |
| | | | | 245 | | | | | 250 | | | | | 255 | |
| Lys | Gly | Pro | Ser | Val | Phe | Pro | Leu | Ala | Pro | Ser | Ser | Lys | Ser | Thr | Ser |
| | | | 260 | | | | | 265 | | | | | 270 | | |
| Gly | Gly | Thr | Ala | Ala | Leu | Gly | Cys | Leu | Val | Lys | Asp | Tyr | Phe | Pro | Glu |
| | | 275 | | | | | 280 | | | | | 285 | | | |
| Pro | Val | Thr | Val | Ser | Trp | Asn | Ser | Gly | Ala | Leu | Thr | Ser | Gly | Val | His |
| | 290 | | | | | 295 | | | | | 300 | | | | |
| Thr | Phe | Pro | Ala | Val | Leu | Gln | Ser | Ser | Gly | Leu | Tyr | Ser | Leu | Ser | Ser |
| 305 | | | | | 310 | | | | | 315 | | | | | 320 |
| Val | Val | Thr | Val | Pro | Ser | Ser | Ser | Leu | Gly | Thr | Gln | Thr | Tyr | Ile | Cys |
| | | | | 325 | | | | | 330 | | | | | 335 | |
| Asn | Val | Asn | His | Lys | Pro | Ser | Asn | Thr | Lys | Val | Asp | Lys | Lys | Val | Glu |
| | | | 340 | | | | | 345 | | | | | 350 | | |
| Pro | Lys | Ser | Cys | Pro | Pro | Cys | Pro | Ala | Pro | Glu | Leu | Leu | Gly | Gly | Pro |
| | | 355 | | | | | 360 | | | | | 365 | | | |
| Ser | Val | Phe | Leu | Phe | Pro | Pro | Lys | Pro | Lys | Asp | Thr | Leu | Met | Ile | Ser |
| | 370 | | | | | 375 | | | | | 380 | | | | |

```
Arg Thr Pro Glu Val Thr Cys Val Val Asp Val Ser His Glu Asp
385                 390                 395                 400

Pro Glu Val Lys Phe Asn Trp Tyr Val Asp Gly Val Glu Val His Asn
            405                 410                 415

Ala Lys Thr Lys Pro Arg Glu Glu Gln Tyr Asn Ser Thr Tyr Arg Val
        420                 425                 430

Val Ser Val Leu Thr Val Leu His Gln Asp Trp Leu Asn Gly Lys Glu
    435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
            485                 490                 495

Cys Leu Val Lys Gly Phe Tyr Pro Ser Asp Ile Ala Val Glu Trp Glu
        500                 505                 510

Ser Asn Gly Gln Pro Glu Asn Asn Tyr Lys Thr Thr Pro Pro Val Leu
    515                 520                 525

Asp Ser Asp Gly Ser Phe Phe Leu His Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
            565                 570                 575

Lys

<210> SEQ ID NO 12
<211> LENGTH: 558
<212> TYPE: PRT
<213> ORGANISM: Artificial Sequence
<220> FEATURE:
<223> OTHER INFORMATION: Synthetic--proBiTE-1s Light chain

<400> SEQUENCE: 12

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
            85                  90                  95

Ser Phe Thr Phe Gly Pro Gly Thr Lys Val Asp Leu Lys Gly Ser Leu
        100                 105                 110

Ser Gly Arg Ser Asp Asn His Gly Gly Gly Ser Asp Ile Gln Met
        115                 120                 125

Thr Gln Ser Pro Ser Ser Leu Ser Ala Ser Val Gly Asp Arg Val Thr
    130                 135                 140

Ile Thr Cys Ser Ala Ser Ser Ser Val Ser Tyr Met Asn Trp Tyr Gln
145                 150                 155                 160
```

Gln Thr Pro Gly Lys Ala Pro Lys Arg Trp Ile Tyr Asp Thr Ser Lys
            165                 170                 175

Leu Ala Ser Gly Val Pro Ser Arg Phe Ser Gly Ser Gly Ser Gly Thr
        180                 185                 190

Asp Tyr Thr Phe Thr Ile Ser Ser Leu Gln Pro Glu Asp Ile Ala Thr
    195                 200                 205

Tyr Tyr Cys Gln Gln Trp Ser Ser Asn Pro Phe Thr Phe Gly Gln Gly
210                 215                 220

Thr Lys Leu Gln Ile Thr Arg Thr Val Ala Ala Pro Ser Val Phe Ile
225                 230                 235                 240

Phe Pro Pro Ser Asp Glu Gln Leu Lys Ser Gly Thr Ala Ser Val Val
            245                 250                 255

Cys Leu Leu Asn Asn Phe Tyr Pro Arg Glu Ala Lys Val Gln Trp Lys
        260                 265                 270

Val Asp Asn Ala Leu Gln Ser Gly Asn Ser Gln Glu Ser Val Thr Glu
    275                 280                 285

Gln Asp Ser Lys Asp Ser Thr Tyr Ser Leu Ser Ser Thr Leu Thr Leu
290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
            325                 330                 335

Cys Pro Pro Cys Pro Ala Pro Glu Leu Leu Gly Gly Pro Ser Val Phe
        340                 345                 350

Leu Phe Pro Pro Lys Pro Lys Asp Thr Leu Met Ile Ser Arg Thr Pro
    355                 360                 365

Glu Val Thr Cys Val Val Val Asp Val Ser His Glu Asp Pro Glu Val
370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
            405                 410                 415

Leu Thr Val Leu His Gln Asp Trp Leu Asn Gly Lys Glu Tyr Lys Cys
        420                 425                 430

Lys Val Ser Asn Lys Ala Leu Pro Ala Pro Ile Glu Lys Thr Ile Ser
    435                 440                 445

Lys Ala Lys Gly Gln Pro Arg Glu Pro Gln Val Tyr Thr Leu Pro Pro
450                 455                 460

Ser Arg Asp Glu Leu Thr Lys Asn Gln Val Ser Leu Leu Cys Leu Val
465                 470                 475                 480

Lys Gly Phe Tyr Pro Ser Asp Ile Ala Val Glu Trp Glu Ser Asn Gly
            485                 490                 495

Gln Pro Glu Asn Asn Tyr Lys Thr Thr Pro Pro Val Leu Asp Ser Asp
        500                 505                 510

Gly Ser Phe Phe Leu His Ser Lys Leu Thr Val Asp Lys Ser Arg Trp
    515                 520                 525

Gln Gln Gly Asn Val Phe Ser Cys Ser Val Met His Glu Ala Leu His
530                 535                 540

Asn His Tyr Thr Gln Lys Ser Leu Ser Leu Ser Pro Gly Lys
545                 550                 555

<210> SEQ ID NO 13
<211> LENGTH: 577
<212> TYPE: PRT

<213> ORGANISM: Artificial Sequence
<220> FEATURE:
<223> OTHER INFORMATION: Synthetic--proBiTE-1s1 Heavy chain

<400> SEQUENCE: 13

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
            165                 170                 175

Lys Gly Leu Glu Trp Ile Gly Tyr Ile Asn Pro Ser Arg Gly Tyr Thr
        180                 185                 190

Asn Tyr Asn Gln Lys Val Lys Asp Arg Phe Thr Ile Ser Thr Asp Lys
    195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
            245                 250                 255

Lys Gly Pro Ser Val Phe Pro Leu Ala Pro Ser Ser Lys Ser Thr Ser
        260                 265                 270

Gly Gly Thr Ala Ala Leu Gly Cys Leu Val Lys Asp Tyr Phe Pro Glu
    275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
            325                 330                 335

Asn Val Asn His Lys Pro Ser Asn Thr Lys Val Asp Lys Lys Val Glu
        340                 345                 350

Pro Lys Ser Cys Pro Pro Cys Pro Ala Pro Glu Leu Leu Gly Gly Pro
    355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
```

```
                385                 390                 395                 400
Pro Glu Val Lys Phe Asn Trp Tyr Val Asp Gly Val Glu Val His Asn
                    405                 410                 415
Ala Lys Thr Lys Pro Arg Glu Glu Gln Tyr Asn Ser Thr Tyr Arg Val
                420                 425                 430
Val Ser Val Leu Thr Val Leu His Gln Asp Trp Leu Asn Gly Lys Glu
                435                 440                 445
Tyr Lys Cys Lys Val Ser Asn Lys Ala Leu Pro Ala Pro Ile Glu Lys
            450                 455                 460
Thr Ile Ser Lys Ala Lys Gly Gln Pro Arg Glu Pro Gln Val Tyr Thr
465                 470                 475                 480
Leu Pro Pro Ser Arg Asp Glu Leu Thr Lys Asn Gln Val Ser Leu Leu
                485                 490                 495
Cys Leu Val Lys Gly Phe Tyr Pro Ser Asp Ile Ala Val Glu Trp Glu
                500                 505                 510
Ser Asn Gly Gln Pro Glu Asn Asn Tyr Lys Thr Thr Pro Pro Val Leu
            515                 520                 525
Asp Ser Asp Gly Ser Phe Phe Leu His Ser Lys Leu Thr Val Asp Lys
            530                 535                 540
Ser Arg Trp Gln Gln Gly Asn Val Phe Ser Cys Ser Val Met His Glu
545                 550                 555                 560
Ala Leu His Asn His Tyr Thr Gln Lys Ser Leu Ser Leu Ser Pro Gly
                565                 570                 575
Lys

<210> SEQ ID NO 14
<211> LENGTH: 558
<212> TYPE: PRT
<213> ORGANISM: Artificial Sequence
<220> FEATURE:
<223> OTHER INFORMATION: Synthetic--proBiTE-1s1 Light chain

<400> SEQUENCE: 14

Asp Val Val Met Thr Gln Ser Pro Ser Thr Leu Ser Ala Ser Val Gly
1               5                   10                  15
Asp Arg Val Thr Ile Thr Cys Arg Ala Ser Gln Ser Met Ser Arg Trp
                20                  25                  30
Leu Ala Trp Tyr Gln Gln Lys Pro Gly Lys Gly Pro Lys Leu Leu Ile
            35                  40                  45
Tyr Ala Thr Ser Thr Leu Gln Ser Gly Val Pro Ser Arg Phe Ser Gly
        50                  55                  60
Ser Gly Ser Gly Thr Glu Phe Thr Leu Thr Ile Ser Ser Leu Gln Pro
65              70                  75                  80
Glu Asp Phe Ala Thr Tyr Tyr Cys Gln Gln Leu Asp Ser Phe Pro Phe
                85                  90                  95
Ser Phe Thr Phe Gly Pro Gly Thr Lys Val Asp Leu Lys Gly Ser Gly
                100                 105                 110
Ser Gly Arg Ser Asp Asn His Gly Gly Gly Ser Asp Ile Gln Met
            115                 120                 125
Thr Gln Ser Pro Ser Ser Leu Ser Ala Ser Val Gly Asp Arg Val Thr
        130                 135                 140
Ile Thr Cys Ser Ala Ser Ser Ser Val Ser Tyr Met Asn Trp Tyr Gln
145                 150                 155                 160
Gln Thr Pro Gly Lys Ala Pro Lys Arg Trp Ile Tyr Asp Thr Ser Lys
                165                 170                 175
```

Leu Ala Ser Gly Val Pro Ser Arg Phe Ser Gly Ser Gly Ser Gly Thr
            180                 185                 190

Asp Tyr Thr Phe Thr Ile Ser Ser Leu Gln Pro Glu Asp Ile Ala Thr
        195                 200                 205

Tyr Tyr Cys Gln Gln Trp Ser Ser Asn Pro Phe Thr Phe Gly Gln Gly
    210                 215                 220

Thr Lys Leu Gln Ile Thr Arg Thr Val Ala Ala Pro Ser Val Phe Ile
225                 230                 235                 240

Phe Pro Pro Ser Asp Glu Gln Leu Lys Ser Gly Thr Ala Ser Val Val
            245                 250                 255

Cys Leu Leu Asn Asn Phe Tyr Pro Arg Glu Ala Lys Val Gln Trp Lys
            260                 265                 270

Val Asp Asn Ala Leu Gln Ser Gly Asn Ser Gln Glu Ser Val Thr Glu
        275                 280                 285

Gln Asp Ser Lys Asp Ser Thr Tyr Ser Leu Ser Ser Thr Leu Thr Leu
    290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
            325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
        355                 360                 365

Glu Val Thr Cys Val Val Val Asp Val Ser His Glu Asp Pro Glu Val
    370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
            405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
    450                 455                 460

Ser Arg Asp Glu Leu Thr Lys Asn Gln Val Ser Leu Leu Cys Leu Val
465                 470                 475                 480

Lys Gly Phe Tyr Pro Ser Asp Ile Ala Val Glu Trp Glu Ser Asn Gly
            485                 490                 495

Gln Pro Glu Asn Asn Tyr Lys Thr Thr Pro Pro Val Leu Asp Ser Asp
            500                 505                 510

Gly Ser Phe Phe Leu His Ser Lys Leu Thr Val Asp Lys Ser Arg Trp
        515                 520                 525

Gln Gln Gly Asn Val Phe Ser Cys Ser Val Met His Glu Ala Leu His
    530                 535                 540

Asn His Tyr Thr Gln Lys Ser Leu Ser Leu Ser Pro Gly Lys
545                 550                 555

<210> SEQ ID NO 15
<211> LENGTH: 577
<212> TYPE: PRT
<213> ORGANISM: Artificial Sequence
<220> FEATURE:

<223> OTHER INFORMATION: Synthetic--proBiTE-1s2 Heavy chain

<400> SEQUENCE: 15

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Gly Gly Gly Ser Gly Gly Gly Gly Gly
        115                 120                 125

Ser Gly Gly Gly Ser Gln Val Gln Leu Val Gln Ser Gly Gly Gly
    130                 135                 140

Val Val Gln Pro Gly Arg Ser Leu Arg Leu Ser Cys Lys Ala Ser Gly
145                 150                 155                 160

Tyr Thr Phe Thr Arg Tyr Thr Met His Trp Val Arg Gln Ala Pro Gly
                165                 170                 175

Lys Gly Leu Glu Trp Ile Gly Tyr Ile Asn Pro Ser Arg Gly Tyr Thr
            180                 185                 190

Asn Tyr Asn Gln Lys Val Lys Asp Arg Phe Thr Ile Ser Thr Asp Lys
        195                 200                 205

Ser Lys Ser Thr Ala Phe Leu Gln Met Asp Ser Leu Arg Pro Glu Asp
    210                 215                 220

Thr Ala Val Tyr Tyr Cys Ala Arg Tyr Tyr Asp Asp His Tyr Ser Leu
225                 230                 235                 240

Asp Tyr Trp Gly Gln Gly Thr Thr Leu Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

```
Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
                420                 425                 430

Val Ser Val Leu Thr Val Leu His Gln Asp Trp Leu Asn Gly Lys Glu
                435                 440                 445

Tyr Lys Cys Lys Val Ser Asn Lys Ala Leu Pro Ala Pro Ile Glu Lys
                450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Leu
                485                 490                 495

Cys Leu Val Lys Gly Phe Tyr Pro Ser Asp Ile Ala Val Glu Trp Glu
                500                 505                 510

Ser Asn Gly Gln Pro Glu Asn Asn Tyr Lys Thr Thr Pro Pro Val Leu
                515                 520                 525

Asp Ser Asp Gly Ser Phe Phe Leu His Ser Lys Leu Thr Val Asp Lys
                530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 16
<211> LENGTH: 558
<212> TYPE: PRT
<213> ORGANISM: Artificial Sequence
<220> FEATURE:
<223> OTHER INFORMATION: Synthetic--proBiTE-1s2 Light chain

<400> SEQUENCE: 16

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
                20                  25                  30

Leu Ala Trp Tyr Gln Gln Lys Pro Gly Lys Gly Pro Lys Leu Leu Ile
                35                  40                  45

Tyr Ala Thr Ser Thr Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Ser Gly
                100                 105                 110

Gly Ser Arg Ser Asp Asn His Gly Gly Gly Ser Asp Ile Gln Met
            115                 120                 125

Thr Gln Ser Pro Ser Ser Leu Ser Ala Ser Val Gly Asp Arg Val Thr
            130                 135                 140

Ile Thr Cys Ser Ala Ser Ser Val Ser Tyr Met Asn Trp Tyr Gln
145                 150                 155                 160

Gln Thr Pro Gly Lys Ala Pro Lys Arg Trp Ile Tyr Asp Thr Ser Lys
                165                 170                 175

Leu Ala Ser Gly Val Pro Ser Arg Phe Ser Gly Ser Gly Ser Gly Thr
```

```
            180             185             190
Asp Tyr Thr Phe Thr Ile Ser Ser Leu Gln Pro Glu Asp Ile Ala Thr
            195             200             205

Tyr Tyr Cys Gln Gln Trp Ser Ser Asn Pro Phe Thr Phe Gly Gln Gly
            210             215             220

Thr Lys Leu Gln Ile Thr Arg Thr Val Ala Ala Pro Ser Val Phe Ile
225             230             235             240

Phe Pro Pro Ser Asp Glu Gln Leu Lys Ser Gly Thr Ala Ser Val Val
            245             250             255

Cys Leu Leu Asn Asn Phe Tyr Pro Arg Glu Ala Lys Val Gln Trp Lys
            260             265             270

Val Asp Asn Ala Leu Gln Ser Gly Asn Ser Gln Glu Ser Val Thr Glu
            275             280             285

Gln Asp Ser Lys Asp Ser Thr Tyr Ser Leu Ser Ser Thr Leu Thr Leu
            290             295             300

Ser Lys Ala Asp Tyr Glu Lys His Lys Val Tyr Ala Cys Glu Val Thr
305             310             315             320

His Gln Gly Leu Ser Ser Pro Val Thr Lys Ser Phe Asn Arg Gly Glu
            325             330             335

Cys Pro Pro Cys Pro Ala Pro Glu Leu Leu Gly Gly Pro Ser Val Phe
            340             345             350

Leu Phe Pro Pro Lys Pro Lys Asp Thr Leu Met Ile Ser Arg Thr Pro
            355             360             365

Glu Val Thr Cys Val Val Val Asp Val Ser His Glu Asp Pro Glu Val
            370             375             380

Lys Phe Asn Trp Tyr Val Asp Gly Val Glu Val His Asn Ala Lys Thr
385             390             395             400

Lys Pro Arg Glu Glu Gln Tyr Asn Ser Thr Tyr Arg Val Val Ser Val
            405             410             415

Leu Thr Val Leu His Gln Asp Trp Leu Asn Gly Lys Glu Tyr Lys Cys
            420             425             430

Lys Val Ser Asn Lys Ala Leu Pro Ala Pro Ile Glu Lys Thr Ile Ser
            435             440             445

Lys Ala Lys Gly Gln Pro Arg Glu Pro Gln Val Tyr Thr Leu Pro Pro
            450             455             460

Ser Arg Asp Glu Leu Thr Lys Asn Gln Val Ser Leu Leu Cys Leu Val
465             470             475             480

Lys Gly Phe Tyr Pro Ser Asp Ile Ala Val Glu Trp Glu Ser Asn Gly
            485             490             495

Gln Pro Glu Asn Asn Tyr Lys Thr Thr Pro Pro Val Leu Asp Ser Asp
            500             505             510

Gly Ser Phe Phe Leu His Ser Lys Leu Thr Val Asp Lys Ser Arg Trp
            515             520             525

Gln Gln Gly Asn Val Phe Ser Cys Ser Val Met His Glu Ala Leu His
            530             535             540

Asn His Tyr Thr Gln Lys Ser Leu Ser Leu Ser Pro Gly Lys
545             550             555

<210> SEQ ID NO 17
<211> LENGTH: 602
<212> TYPE: PRT
<213> ORGANISM: Artificial Sequence
<220> FEATURE:
<223> OTHER INFORMATION: Synthetic--dproBiTE-HE Heavy chain
```

<400> SEQUENCE: 17

```
Leu Thr Ser Ile Ile Ser Ala Val Val Gly Gly Gly Ser Gly
1               5                   10                  15

Gly Gly Gly Ser Gly Gly Gly Ser Glu Val Gln Leu Val Glu Thr
            20                  25                  30

Gly Gly Gly Val Val Gln Pro Gly Arg Ser Leu Arg Leu Ser Cys Ala
            35                  40                  45

Ala Ser Gly Phe Thr Phe Ser Ser Tyr Ala Met His Trp Val Arg Gln
50                  55                  60

Ala Pro Gly Lys Gly Leu Glu Trp Val Ala Val Ile Ser Tyr Asp Gly
65                  70                  75                  80

Ser Asn Lys Tyr Tyr Ala Asp Ser Val Lys Gly Arg Phe Thr Ile Ser
                85                  90                  95

Arg Asp Asn Ser Lys Asn Thr Leu Tyr Leu Gln Met Asn Ser Leu Arg
                100                 105                 110

Ala Glu Asp Thr Ala Val Tyr Tyr Cys Ala Arg Gly Tyr Val Ala Arg
                115                 120                 125

Gly Asp Phe Asp Tyr Trp Gly Gln Gly Thr Leu Val Thr Val Ser Ser
            130                 135                 140

Gly Gly Gly Ser Ser Gly Gly Gly Ser Gly Gly Gly Ser Gln
145                 150                 155                 160

Val Gln Leu Val Gln Ser Gly Gly Val Val Gln Pro Gly Arg Ser
                165                 170                 175

Leu Arg Leu Ser Cys Lys Ala Ser Gly Tyr Thr Phe Thr Arg Tyr Thr
                180                 185                 190

Met His Trp Val Arg Gln Ala Pro Gly Lys Gly Leu Glu Trp Ile Gly
            195                 200                 205

Tyr Ile Asn Pro Ser Arg Gly Tyr Thr Asn Tyr Asn Gln Lys Val Lys
            210                 215                 220

Asp Arg Phe Thr Ile Ser Thr Asp Lys Ser Lys Ser Thr Ala Phe Leu
225                 230                 235                 240

Gln Met Asp Ser Leu Arg Pro Glu Asp Thr Ala Val Tyr Tyr Cys Ala
                245                 250                 255

Arg Tyr Tyr Asp Asp His Tyr Ser Leu Asp Tyr Trp Gly Gln Gly Thr
                260                 265                 270

Thr Leu Thr Val Ser Ser Ala Ser Thr Lys Gly Pro Ser Val Phe Pro
            275                 280                 285

Leu Ala Pro Ser Ser Lys Ser Thr Ser Gly Gly Thr Ala Ala Leu Gly
            290                 295                 300

Cys Leu Val Lys Asp Tyr Phe Pro Glu Pro Val Thr Val Ser Trp Asn
305                 310                 315                 320

Ser Gly Ala Leu Thr Ser Gly Val His Thr Phe Pro Ala Val Leu Gln
                325                 330                 335

Ser Ser Gly Leu Tyr Ser Leu Ser Ser Val Val Thr Val Pro Ser Ser
                340                 345                 350

Ser Leu Gly Thr Gln Thr Tyr Ile Cys Asn Val Asn His Lys Pro Ser
            355                 360                 365

Asn Thr Lys Val Asp Lys Lys Val Glu Pro Lys Ser Cys Pro Pro Cys
370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415
```

```
Val Val Val Asp Val Ser His Glu Asp Pro Glu Val Lys Phe Asn Trp
            420                 425                 430

Tyr Val Asp Gly Val Glu Val His Asn Ala Lys Thr Lys Pro Arg Glu
        435                 440                 445

Glu Gln Tyr Asn Ser Thr Tyr Arg Val Val Ser Val Leu Thr Val Leu
    450                 455                 460

His Gln Asp Trp Leu Asn Gly Lys Glu Tyr Lys Cys Lys Val Ser Asn
465                 470                 475                 480

Lys Ala Leu Pro Ala Pro Ile Glu Lys Thr Ile Ser Lys Ala Lys Gly
                485                 490                 495

Gln Pro Arg Glu Pro Gln Val Tyr Thr Leu Pro Pro Ser Arg Asp Glu
            500                 505                 510

Leu Thr Lys Asn Gln Val Ser Leu Leu Cys Leu Val Lys Gly Phe Tyr
        515                 520                 525

Pro Ser Asp Ile Ala Val Glu Trp Glu Ser Asn Gly Gln Pro Glu Asn
    530                 535                 540

Asn Tyr Lys Thr Thr Pro Pro Val Leu Asp Ser Asp Gly Ser Phe Phe
545                 550                 555                 560

Leu His Ser Lys Leu Thr Val Asp Lys Ser Arg Trp Gln Gln Gly Asn
                565                 570                 575

Val Phe Ser Cys Ser Val Met His Glu Ala Leu His Asn His Tyr Thr
            580                 585                 590

Gln Lys Ser Leu Ser Leu Ser Pro Gly Lys
        595                 600

<210> SEQ ID NO 18
<211> LENGTH: 582
<212> TYPE: PRT
<213> ORGANISM: Artificial Sequence
<220> FEATURE:
<223> OTHER INFORMATION: Synthetic--dproBiTE-HE Light chain

<400> SEQUENCE: 18

Ser Ile Ala Thr Gly Met Val Gly Gly Gly Gly Ser Gly Gly Gly
1               5                   10                  15

Gly Ser Gly Arg Ser Asp Asn His Asp Val Val Met Thr Gln Ser Pro
                20                  25                  30

Ser Thr Leu Ser Ala Ser Val Gly Asp Arg Val Thr Ile Thr Cys Arg
            35                  40                  45

Ala Ser Gln Ser Met Ser Arg Trp Leu Ala Trp Tyr Gln Gln Lys Pro
        50                  55                  60

Gly Lys Gly Pro Lys Leu Leu Ile Tyr Ala Thr Ser Thr Leu Gln Ser
65                  70                  75                  80

Gly Val Pro Ser Arg Phe Ser Gly Ser Gly Ser Gly Thr Glu Phe Thr
                85                  90                  95

Leu Thr Ile Ser Ser Leu Gln Pro Glu Asp Phe Ala Thr Tyr Tyr Cys
            100                 105                 110

Gln Gln Leu Asp Ser Phe Pro Phe Ser Phe Thr Phe Gly Pro Gly Thr
        115                 120                 125

Lys Val Asp Leu Lys Gly Ser Gly Ser Gly Arg Ser Asp Asn His Gly
    130                 135                 140

Gly Gly Gly Ser Asp Ile Gln Met Thr Gln Ser Pro Ser Ser Leu Ser
145                 150                 155                 160

Ala Ser Val Gly Asp Arg Val Thr Ile Thr Cys Ser Ala Ser Ser Ser
                165                 170                 175
```

```
Val Ser Tyr Met Asn Trp Tyr Gln Gln Thr Pro Gly Lys Ala Pro Lys
            180                 185                 190

Arg Trp Ile Tyr Asp Thr Ser Lys Leu Ala Ser Gly Val Pro Ser Arg
            195                 200                 205

Phe Ser Gly Ser Gly Ser Gly Thr Asp Tyr Thr Phe Thr Ile Ser Ser
    210                 215                 220

Leu Gln Pro Glu Asp Ile Ala Thr Tyr Tyr Cys Gln Gln Trp Ser Ser
225                 230                 235                 240

Asn Pro Phe Thr Phe Gly Gln Gly Thr Lys Leu Gln Ile Thr Arg Thr
                245                 250                 255

Val Ala Ala Pro Ser Val Phe Ile Phe Pro Pro Ser Asp Glu Gln Leu
            260                 265                 270

Lys Ser Gly Thr Ala Ser Val Val Cys Leu Leu Asn Asn Phe Tyr Pro
            275                 280                 285

Arg Glu Ala Lys Val Gln Trp Lys Val Asp Asn Ala Leu Gln Ser Gly
            290                 295                 300

Asn Ser Gln Glu Ser Val Thr Glu Gln Asp Ser Lys Asp Ser Thr Tyr
305                 310                 315                 320

Ser Leu Ser Ser Thr Leu Thr Leu Ser Lys Ala Asp Tyr Glu Lys His
                325                 330                 335

Lys Val Tyr Ala Cys Glu Val Thr His Gln Gly Leu Ser Ser Pro Val
            340                 345                 350

Thr Lys Ser Phe Asn Arg Gly Glu Cys Pro Pro Cys Pro Ala Pro Glu
            355                 360                 365

Leu Leu Gly Gly Pro Ser Val Phe Leu Phe Pro Pro Lys Pro Lys Asp
            370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
            435                 440                 445

Leu Asn Gly Lys Glu Tyr Lys Cys Lys Val Ser Asn Lys Ala Leu Pro
            450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Leu Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
            515                 520                 525

Thr Pro Pro Val Leu Asp Ser Asp Gly Ser Phe Phe Leu His Ser Lys
            530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
                580
```

<210> SEQ ID NO 19
<211> LENGTH: 602
<212> TYPE: PRT
<213> ORGANISM: Artificial Sequence
<220> FEATURE:
<223> OTHER INFORMATION: Synthetic--dproBiTE-GS Heavy chain

<400> SEQUENCE: 19

```
Gly Gly Gly Gly Ser Gly Gly Gly Ser Gly Gly Gly Ser Gly
1               5                   10                  15

Gly Gly Gly Ser Gly Gly Gly Ser Glu Val Gln Leu Val Glu Thr
                20              25                  30

Gly Gly Gly Val Val Gln Pro Gly Arg Ser Leu Arg Leu Ser Cys Ala
            35              40                  45

Ala Ser Gly Phe Thr Phe Ser Ser Tyr Ala Met His Trp Val Arg Gln
    50                  55                  60

Ala Pro Gly Lys Gly Leu Glu Trp Val Ala Val Ile Ser Tyr Asp Gly
65                  70                  75                  80

Ser Asn Lys Tyr Tyr Ala Asp Ser Val Lys Gly Arg Phe Thr Ile Ser
                85                  90                  95

Arg Asp Asn Ser Lys Asn Thr Leu Tyr Leu Gln Met Asn Ser Leu Arg
            100                 105                 110

Ala Glu Asp Thr Ala Val Tyr Tyr Cys Ala Arg Gly Tyr Val Ala Arg
        115                 120                 125

Gly Asp Phe Asp Tyr Trp Gly Gln Gly Thr Leu Val Thr Val Ser Ser
    130                 135                 140

Gly Gly Gly Ser Ser Gly Gly Ser Gly Gly Gly Ser Gln
145                 150                 155                 160

Val Gln Leu Val Gln Ser Gly Gly Val Val Gln Pro Gly Arg Ser
                165                 170                 175

Leu Arg Leu Ser Cys Lys Ala Ser Gly Tyr Thr Phe Thr Arg Tyr Thr
            180                 185                 190

Met His Trp Val Arg Gln Ala Pro Gly Lys Gly Leu Glu Trp Ile Gly
        195                 200                 205

Tyr Ile Asn Pro Ser Arg Gly Tyr Thr Asn Tyr Asn Gln Lys Val Lys
    210                 215                 220

Asp Arg Phe Thr Ile Ser Thr Asp Lys Ser Lys Ser Thr Ala Phe Leu
225                 230                 235                 240

Gln Met Asp Ser Leu Arg Pro Glu Asp Thr Ala Val Tyr Tyr Cys Ala
                245                 250                 255

Arg Tyr Tyr Asp Asp His Tyr Ser Leu Asp Tyr Trp Gly Gln Gly Thr
            260                 265                 270

Thr Leu Thr Val Ser Ser Ala Ser Thr Lys Gly Pro Ser Val Phe Pro
        275                 280                 285

Leu Ala Pro Ser Ser Lys Ser Thr Ser Gly Gly Thr Ala Ala Leu Gly
    290                 295                 300

Cys Leu Val Lys Asp Tyr Phe Pro Glu Pro Val Thr Val Ser Trp Asn
305                 310                 315                 320

Ser Gly Ala Leu Thr Ser Gly Val His Thr Phe Pro Ala Val Leu Gln
                325                 330                 335

Ser Ser Gly Leu Tyr Ser Leu Ser Val Val Thr Val Pro Ser Ser
            340                 345                 350

Ser Leu Gly Thr Gln Thr Tyr Ile Cys Asn Val Asn His Lys Pro Ser
        355                 360                 365
```

```
Asn Thr Lys Val Asp Lys Lys Val Glu Pro Lys Ser Cys Pro Pro Cys
    370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415

Val Val Val Asp Val Ser His Glu Asp Pro Glu Val Lys Phe Asn Trp
            420                 425                 430

Tyr Val Asp Gly Val Glu Val His Asn Ala Lys Thr Lys Pro Arg Glu
        435                 440                 445

Glu Gln Tyr Asn Ser Thr Tyr Arg Val Val Ser Val Leu Thr Val Leu
    450                 455                 460

His Gln Asp Trp Leu Asn Gly Lys Glu Tyr Lys Cys Lys Val Ser Asn
465                 470                 475                 480

Lys Ala Leu Pro Ala Pro Ile Glu Lys Thr Ile Ser Lys Ala Lys Gly
                485                 490                 495

Gln Pro Arg Glu Pro Gln Val Tyr Thr Leu Pro Pro Ser Arg Asp Glu
            500                 505                 510

Leu Thr Lys Asn Gln Val Ser Leu Leu Cys Leu Val Lys Gly Phe Tyr
        515                 520                 525

Pro Ser Asp Ile Ala Val Glu Trp Glu Ser Asn Gly Gln Pro Glu Asn
    530                 535                 540

Asn Tyr Lys Thr Thr Pro Pro Val Leu Asp Ser Asp Gly Ser Phe Phe
545                 550                 555                 560

Leu His Ser Lys Leu Thr Val Asp Lys Ser Arg Trp Gln Gln Gly Asn
                565                 570                 575

Val Phe Ser Cys Ser Val Met His Glu Ala Leu His Asn His Tyr Thr
            580                 585                 590

Gln Lys Ser Leu Ser Leu Ser Pro Gly Lys
        595                 600

<210> SEQ ID NO 20
<211> LENGTH: 584
<212> TYPE: PRT
<213> ORGANISM: Artificial Sequence
<220> FEATURE:
<223> OTHER INFORMATION: Synthetic--dproBiTE-GS Light chain

<400> SEQUENCE: 20

Gly Gly Gly Gly Ser Gly Gly Gly Ser Gly Gly Gly Ser Gly
1               5                   10                  15

Gly Gly Gly Ser Gly Arg Ser Asp Asn His Asp Val Val Met Thr Gln
            20                  25                  30

Ser Pro Ser Thr Leu Ser Ala Ser Val Gly Asp Arg Val Thr Ile Thr
        35                  40                  45

Cys Arg Ala Ser Gln Ser Met Ser Arg Trp Leu Ala Trp Tyr Gln Gln
    50                  55                  60

Lys Pro Gly Lys Gly Pro Lys Leu Leu Ile Tyr Ala Thr Ser Thr Leu
65                  70                  75                  80

Gln Ser Gly Val Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

Tyr Cys Gln Gln Leu Asp Ser Phe Pro Phe Ser Phe Thr Phe Gly Pro
        115                 120                 125
```

-continued

```
Gly Thr Lys Val Asp Leu Lys Gly Ser Gly Ser Arg Ser Asp Asn
130                 135             140
His Gly Gly Gly Ser Asp Ile Gln Met Thr Gln Ser Pro Ser Ser
145             150              155             160
Leu Ser Ala Ser Val Gly Asp Arg Val Thr Ile Thr Cys Ser Ala Ser
            165             170             175
Ser Ser Val Ser Tyr Met Asn Trp Tyr Gln Gln Thr Pro Gly Lys Ala
        180             185             190
Pro Lys Arg Trp Ile Tyr Asp Thr Ser Lys Leu Ala Ser Gly Val Pro
        195             200             205
Ser Arg Phe Ser Gly Ser Gly Ser Gly Thr Asp Tyr Thr Phe Thr Ile
210             215             220
Ser Ser Leu Gln Pro Glu Asp Ile Ala Thr Tyr Tyr Cys Gln Gln Trp
225             230             235             240
Ser Ser Asn Pro Phe Thr Phe Gly Gln Gly Thr Lys Leu Gln Ile Thr
            245             250             255
Arg Thr Val Ala Ala Pro Ser Val Phe Ile Phe Pro Pro Ser Asp Glu
            260             265             270
Gln Leu Lys Ser Gly Thr Ala Ser Val Val Cys Leu Leu Asn Asn Phe
            275             280             285
Tyr Pro Arg Glu Ala Lys Val Gln Trp Lys Val Asp Asn Ala Leu Gln
290             295             300
Ser Gly Asn Ser Gln Glu Ser Val Thr Glu Gln Asp Ser Lys Asp Ser
305             310             315             320
Thr Tyr Ser Leu Ser Ser Thr Leu Thr Leu Ser Lys Ala Asp Tyr Glu
            325             330             335
Lys His Lys Val Tyr Ala Cys Glu Val Thr His Gln Gly Leu Ser Ser
            340             345             350
Pro Val Thr Lys Ser Phe Asn Arg Gly Glu Cys Pro Pro Cys Pro Ala
            355             360             365
Pro Glu Leu Leu Gly Gly Pro Ser Val Phe Leu Phe Pro Pro Lys Pro
    370             375             380
Lys Asp Thr Leu Met Ile Ser Arg Thr Pro Glu Val Thr Cys Val Val
385             390             395             400
Val Asp Val Ser His Glu Asp Pro Glu Val Lys Phe Asn Trp Tyr Val
            405             410             415
Asp Gly Val Glu Val His Asn Ala Lys Thr Lys Pro Arg Glu Glu Gln
            420             425             430
Tyr Asn Ser Thr Tyr Arg Val Val Ser Val Leu Thr Val Leu His Gln
            435             440             445
Asp Trp Leu Asn Gly Lys Glu Tyr Lys Cys Lys Val Ser Asn Lys Ala
    450             455             460
Leu Pro Ala Pro Ile Glu Lys Thr Ile Ser Lys Ala Lys Gly Gln Pro
465             470             475             480
Arg Glu Pro Gln Val Tyr Thr Leu Pro Pro Ser Arg Asp Glu Leu Thr
            485             490             495
Lys Asn Gln Val Ser Leu Leu Cys Leu Val Lys Gly Phe Tyr Pro Ser
            500             505             510
Asp Ile Ala Val Glu Trp Glu Ser Asn Gly Gln Pro Glu Asn Asn Tyr
            515             520             525
Lys Thr Thr Pro Pro Val Leu Asp Ser Asp Gly Ser Phe Phe Leu His
    530             535             540
Ser Lys Leu Thr Val Asp Lys Ser Arg Trp Gln Gln Gly Asn Val Phe
```

```
545                 550                 555                 560
Ser Cys Ser Val Met His Glu Ala Leu His Asn His Tyr Thr Gln Lys
                565                 570                 575
Ser Leu Ser Leu Ser Pro Gly Lys
                580

<210> SEQ ID NO 21
<211> LENGTH: 119
<212> TYPE: PRT
<213> ORGANISM: Homo sapiens

<400> SEQUENCE: 21

Glu Val Gln Leu Val Glu Thr Gly Gly Gly Val Val Gln Pro Gly Arg
1               5                   10                  15
Ser Leu Arg Leu Ser Cys Ala Ala Ser Gly Phe Thr Phe Ser Ser Tyr
                20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Val Ala Arg Gly Asp Phe Asp Tyr Trp Gly Gln Gly
                100                 105                 110
Thr Leu Val Thr Val Ser Ser
            115

<210> SEQ ID NO 22
<211> LENGTH: 8
<212> TYPE: PRT
<213> ORGANISM: Homo sapiens

<400> SEQUENCE: 22

Gly Phe Thr Phe Ser Ser Tyr Ala
1               5

<210> SEQ ID NO 23
<211> LENGTH: 8
<212> TYPE: PRT
<213> ORGANISM: Homo sapiens

<400> SEQUENCE: 23

Ile Ser Tyr Asp Gly Ser Asn Lys
1               5

<210> SEQ ID NO 24
<211> LENGTH: 12
<212> TYPE: PRT
<213> ORGANISM: Homo sapiens

<400> SEQUENCE: 24

Ala Arg Gly Tyr Val Ala Arg Gly Asp Phe Asp Tyr
1               5                   10

<210> SEQ ID NO 25
<211> LENGTH: 107
<212> TYPE: PRT
<213> ORGANISM: Homo sapiens
```

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Val Asp Ser Trp
            20                  25                  30

Leu Ala Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Ile Ala Pro His
                85                  90                  95

Thr Phe Gly Gln Gly Thr Leu Glu Ile Lys
            100                 105

<210> SEQ ID NO 26
<211> LENGTH: 6
<212> TYPE: PRT
<213> ORGANISM: Homo sapiens

<400> SEQUENCE: 26

Gln Thr Val Asp Ser Trp
1               5

<210> SEQ ID NO 27
<211> LENGTH: 3
<212> TYPE: PRT
<213> ORGANISM: Homo sapiens

<400> SEQUENCE: 27

Ala Thr Ser
1

<210> SEQ ID NO 28
<211> LENGTH: 9
<212> TYPE: PRT
<213> ORGANISM: Homo sapiens

<400> SEQUENCE: 28

Gln Gln Gly His Ile Ala Pro His Thr
1               5

<210> SEQ ID NO 29
<211> LENGTH: 119
<212> TYPE: PRT
<213> ORGANISM: Homo sapiens

<400> SEQUENCE: 29

Glu Val Gln Leu Val Glu Thr Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Arg Gly Tyr Val Ala Arg Gly Asp Phe Asp Tyr Trp Gly Gln Gly
            100                 105                 110

Thr Leu Val Thr Val Ser Ser
        115

<210> SEQ ID NO 30
<211> LENGTH: 109
<212> TYPE: PRT
<213> ORGANISM: Homo sapiens

<400> SEQUENCE: 30

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
            35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys
            100                 105

<210> SEQ ID NO 31
<211> LENGTH: 6
<212> TYPE: PRT
<213> ORGANISM: Homo sapiens

<400> SEQUENCE: 31

Gln Ser Met Ser Arg Trp
1               5

<210> SEQ ID NO 32
<211> LENGTH: 3
<212> TYPE: PRT
<213> ORGANISM: Homo sapiens

<400> SEQUENCE: 32

Ala Thr Ser
1

<210> SEQ ID NO 33
<211> LENGTH: 11
<212> TYPE: PRT
<213> ORGANISM: Homo sapiens

<400> SEQUENCE: 33

Gln Gln Leu Asp Ser Phe Pro Phe Ser Phe Thr
1               5                   10

<210> SEQ ID NO 34
<211> LENGTH: 119
<212> TYPE: PRT
<213> ORGANISM: Homo sapiens

<400> SEQUENCE: 34
```

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser
            115

<210> SEQ ID NO 35
<211> LENGTH: 109
<212> TYPE: PRT
<213> ORGANISM: Homo sapiens

<400> SEQUENCE: 35

Asp Ile Gln Leu Thr Gln Ser Pro Ser Thr Leu Ser Ala Ser Val Gly
1               5                   10                  15

Asp Arg Val Thr Ile Thr Cys Arg Ser Asn Gln Thr Ala Asp Ser Trp
            20                  25                  30

Leu Ala Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Met Phe Thr Phe Gly Gln Gly Thr Lys Leu Glu Ile Lys
            100                 105

<210> SEQ ID NO 36
<211> LENGTH: 6
<212> TYPE: PRT
<213> ORGANISM: Homo sapiens

<400> SEQUENCE: 36

Gln Thr Ala Asp Ser Trp
1               5

<210> SEQ ID NO 37
<211> LENGTH: 3
<212> TYPE: PRT
<213> ORGANISM: Homo sapiens

<400> SEQUENCE: 37

Ala Ala Ser
1

<210> SEQ ID NO 38
<211> LENGTH: 11
<212> TYPE: PRT

```
<213> ORGANISM: Homo sapiens

<400> SEQUENCE: 38

Gln Gln Ser Tyr Ser Thr Pro Phe Met Phe Thr
1               5                   10

<210> SEQ ID NO 39
<211> LENGTH: 119
<212> TYPE: PRT
<213> ORGANISM: Homo sapiens

<400> SEQUENCE: 39

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser
        115

<210> SEQ ID NO 40
<211> LENGTH: 107
<212> TYPE: PRT
<213> ORGANISM: Homo sapiens

<400> SEQUENCE: 40

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ala Leu Gln Ser Gly Val Pro Ser Arg Phe Ser Gly
        50                  55                  60

Ser Gly Ser Gly Thr Glu Phe Thr Leu Thr Ile Tyr Asp Leu Gln Pro
65                  70                  75                  80

Asp Asp Phe Ala Thr Tyr Phe Cys Gln Gln Tyr Asp Thr Phe Leu Trp
                85                  90                  95

Thr Phe Gly Gln Gly Thr Lys Val Glu Ile Lys
            100                 105

<210> SEQ ID NO 41
<211> LENGTH: 6
<212> TYPE: PRT
<213> ORGANISM: Homo sapiens

<400> SEQUENCE: 41

Gln Gly Ile Ser Ser Trp
1               5
```

```
<210> SEQ ID NO 42
<211> LENGTH: 3
<212> TYPE: PRT
<213> ORGANISM: Homo sapiens

<400> SEQUENCE: 42

Ala Ala Ser
1

<210> SEQ ID NO 43
<211> LENGTH: 9
<212> TYPE: PRT
<213> ORGANISM: Homo sapiens

<400> SEQUENCE: 43

Gln Gln Tyr Asp Thr Phe Leu Trp Thr
1               5

<210> SEQ ID NO 44
<211> LENGTH: 449
<212> TYPE: PRT
<213> ORGANISM: Homo sapiens

<400> SEQUENCE: 44

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                260                 265                 270
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 45
<211> LENGTH: 214
<212> TYPE: PRT
<213> ORGANISM: Homo sapiens

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Val Asp Ser Trp
            20                  25                  30

Leu Ala Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Ile Ala Pro His
                85                  90                  95

Thr Phe Gly Gln Gly Thr Thr Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190
Ala Cys Glu Val Thr His Gln Gly Leu Ser Ser Pro Val Thr Lys Ser
            195                 200                 205

Phe Asn Arg Gly Glu Cys
            210

<210> SEQ ID NO 46
<211> LENGTH: 449
<212> TYPE: PRT
<213> ORGANISM: Homo sapiens

<400> SEQUENCE: 46

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 47
<211> LENGTH: 216
<212> TYPE: PRT
<213> ORGANISM: Homo sapiens

<400> SEQUENCE: 47

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 48
<211> LENGTH: 449
<212> TYPE: PRT
<213> ORGANISM: Homo sapiens
```

```
<400> SEQUENCE: 48

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Ala Arg Gly Asp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 49
<211> LENGTH: 216
<212> TYPE: PRT
<213> ORGANISM: Homo sapiens

<400> SEQUENCE: 49

Asp Ile Gln Leu Thr Gln Ser Pro Ser Thr Leu Ser Ala Ser Val Gly
1               5                   10                  15

Asp Arg Val Thr Ile Thr Cys Arg Ser Asn Gln Thr Ala Asp Ser Trp
            20                  25                  30

Leu Ala Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Met Phe Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 50
<211> LENGTH: 583
<212> TYPE: PRT
<213> ORGANISM: Artificial Sequence
<220> FEATURE:
<223> OTHER INFORMATION: Synthetic--Heavy chain of proBiTE-1s1sp

<400> SEQUENCE: 50

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
```

-continued

```
               50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Gly Tyr Val Ala Arg Gly Asp Phe Asp Tyr Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Glu Val Gln Leu Val Glu Ser Gly Gly Gly
                130                 135                 140

Leu Val Gln Pro Gly Gly Ser Leu Arg Leu Ser Cys Ala Ala Ser Gly
145                 150                 155                 160

Phe Thr Phe Asn Thr Tyr Ala Met Asn Trp Val Arg Gln Ala Pro Gly
                165                 170                 175

Lys Gly Leu Glu Trp Val Ala Arg Ile Arg Ser Lys Tyr Asn Asn Tyr
                180                 185                 190

Ala Thr Tyr Tyr Ala Asp Ser Val Lys Gly Arg Phe Thr Ile Ser Arg
                195                 200                 205

Asp Asp Ser Lys Asn Thr Leu Tyr Leu Gln Met Asn Ser Leu Arg Ala
210                 215                 220

Glu Asp Thr Ala Val Tyr Tyr Cys Val Arg His Gly Asn Phe Gly Asn
225                 230                 235                 240

Ser Tyr Val Ser Tyr Phe Ala Tyr Trp Gly Gln Gly Thr Thr Val Thr
                245                 250                 255

Val Ser Ser Ala Ser Thr Lys Gly Pro Ser Val Phe Pro Leu Ala Pro
                260                 265                 270

Ser Ser Lys Ser Thr Ser Gly Gly Thr Ala Ala Leu Gly Cys Leu Val
                275                 280                 285

Lys Asp Tyr Phe Pro Glu Pro Val Thr Val Ser Trp Asn Ser Gly Ala
                290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Ser Leu Gly
                325                 330                 335

Thr Gln Thr Tyr Ile Cys Asn Val Asn His Lys Pro Ser Asn Thr Lys
                340                 345                 350

Val Asp Lys Lys Val Glu Pro Lys Ser Cys Pro Pro Cys Pro Ala Pro
                355                 360                 365

Glu Leu Leu Gly Gly Pro Ser Val Phe Leu Phe Pro Pro Lys Pro Lys
                370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
                420                 425                 430

Asn Ser Thr Tyr Arg Val Val Ser Val Leu Thr Val Leu His Gln Asp
                435                 440                 445

Trp Leu Asn Gly Lys Glu Tyr Lys Cys Lys Val Ser Asn Lys Ala Leu
450                 455                 460

Pro Ala Pro Ile Glu Lys Thr Ile Ser Lys Ala Lys Gly Gln Pro Arg
465                 470                 475                 480
```

```
Glu Pro Gln Val Tyr Thr Leu Pro Pro Ser Arg Asp Glu Leu Thr Lys
                485                 490                 495

Asn Gln Val Ser Leu Leu Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu His Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 51
<211> LENGTH: 562
<212> TYPE: PRT
<213> ORGANISM: Artificial Sequence
<220> FEATURE:
<223> OTHER INFORMATION: Synthetic--Light chain of proBiTE-1s1sp

<400> SEQUENCE: 51

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
            20                  25                  30

Leu Ala Trp Tyr Gln Gln Lys Pro Gly Lys Gly Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Ser Gly
            100                 105                 110

Ser Gly Arg Ser Asp Asn His Gly Gly Gly Ser Glu Ile Val Val
        115                 120                 125

Thr Gln Ser Pro Ala Thr Leu Ser Val Ser Pro Gly Glu Arg Ala Thr
    130                 135                 140

Leu Ser Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Ala Asn Lys Arg Ala Pro Gly Val Pro Ala Arg Phe Ser Gly Ser
            180                 185                 190

Leu Ser Gly Asp Glu Ala Thr Leu Thr Ile Ser Ser Leu Gln Ser Glu
        195                 200                 205

Asp Phe Ala Val Tyr Tyr Cys Ala Leu Trp Tyr Ser Asn Leu Trp Val
    210                 215                 220

Phe Gly Gln Gly Thr Lys Leu Glu Ile Lys Arg Thr Val Ala Ala Pro
225                 230                 235                 240

Ser Val Phe Ile Phe Pro Pro Ser Asp Glu Gln Leu Lys Ser Gly Thr
                245                 250                 255
```

```
Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Ser Arg Asp Glu Leu Thr Lys Asn Gln Val Ser Leu
465                 470                 475                 480

Leu Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu His Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Lys

<210> SEQ ID NO 52
<211> LENGTH: 583
<212> TYPE: PRT
<213> ORGANISM: Artificial Sequence
<220> FEATURE:
<223> OTHER INFORMATION: Synthetic--Heavy chain of proBiTE-1s1spg

<400> SEQUENCE: 52

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45
```

```
Ala Val Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Tyr Val Ala Arg Gly Asp Phe Asp Tyr Trp Gly Gln Gly
                100                 105                 110
Thr Leu Val Thr Val Ser Ser Gly Gly Ser Gly Gly Gly Gly
                115                 120                 125
Ser Gly Gly Gly Ser Glu Val Gln Leu Val Glu Ser Gly Gly Gly
130                 135                 140
Leu Val Gln Pro Gly Gly Ser Leu Arg Leu Ser Cys Ala Ala Ser Gly
145                 150                 155                 160
Phe Thr Phe Asn Thr Tyr Ala Met Asn Trp Val Arg Gln Ala Pro Gly
                165                 170                 175
Lys Gly Leu Glu Trp Val Ala Arg Ile Arg Ser Lys Tyr Asn Asn Tyr
                180                 185                 190
Ala Thr Tyr Tyr Ala Asp Ser Val Lys Gly Arg Phe Thr Ile Ser Arg
                195                 200                 205
Asp Asp Ser Lys Asn Thr Leu Tyr Leu Gln Met Asn Ser Leu Arg Ala
210                 215                 220
Glu Asp Thr Ala Val Tyr Tyr Cys Ala Arg His Gly Asn Phe Gly Ser
225                 230                 235                 240
Ser Tyr Val Ser Tyr Phe Ala Tyr Trp Gly Gln Gly Thr Thr Val Thr
                245                 250                 255
Val Ser Ser Ala Ser Thr Lys Gly Pro Ser Val Phe Pro Leu Ala Pro
                260                 265                 270
Ser Ser Lys Ser Thr Ser Gly Gly Thr Ala Ala Leu Gly Cys Leu Val
        275                 280                 285
Lys Asp Tyr Phe Pro Glu Pro Val Thr Val Ser Trp Asn Ser Gly Ala
        290                 295                 300
Leu Thr Ser Gly Val His Thr Phe Pro Ala Val Leu Gln Ser Ser Gly
305                 310                 315                 320
Leu Tyr Ser Leu Ser Ser Val Val Thr Val Pro Ser Ser Ser Leu Gly
                325                 330                 335
Thr Gln Thr Tyr Ile Cys Asn Val Asn His Lys Pro Ser Asn Thr Lys
                340                 345                 350
Val Asp Lys Lys Val Glu Pro Lys Ser Cys Pro Pro Cys Pro Ala Pro
        355                 360                 365
Glu Leu Leu Gly Gly Pro Ser Val Phe Leu Phe Pro Pro Lys Pro Lys
370                 375                 380
Asp Thr Leu Met Ile Ser Arg Thr Pro Glu Val Thr Cys Val Val Val
385                 390                 395                 400
Asp Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
                420                 425                 430
Asn Ser Thr Tyr Arg Val Val Ser Val Leu Thr Val Leu His Gln Asp
                435                 440                 445
Trp Leu Asn Gly Lys Glu Tyr Lys Cys Lys Val Ser Asn Lys Ala Leu
450                 455                 460
Pro Ala Pro Ile Glu Lys Thr Ile Ser Lys Ala Lys Gly Gln Pro Arg
```

```
                  465                 470                 475                 480
Glu Pro Gln Val Tyr Thr Leu Pro Pro Ser Arg Asp Glu Leu Thr Lys
                    485                 490                 495

Asn Gln Val Ser Leu Leu Cys Leu Val Lys Gly Phe Tyr Pro Ser Asp
                500                 505                 510

Ile Ala Val Glu Trp Glu Ser Asn Gly Gln Pro Glu Asn Asn Tyr Lys
                515                 520                 525

Thr Thr Pro Pro Val Leu Asp Ser Asp Gly Ser Phe Phe Leu His Ser
530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
                580

<210> SEQ ID NO 53
<211> LENGTH: 562
<212> TYPE: PRT
<213> ORGANISM: Artificial Sequence
<220> FEATURE:
<223> OTHER INFORMATION: Synthetic--Light chain of proBiTE-1s1spg

<400> SEQUENCE: 53

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Met Ser Arg Trp
                20                  25                  30

Leu Ala Trp Tyr Gln Gln Lys Pro Gly Lys Gly Pro Lys Leu Leu Ile
                35                  40                  45

Tyr Ala Thr Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Leu Asp Ser Phe Pro Phe
                85                  90                  95

Ser Phe Thr Phe Gly Pro Gly Thr Lys Val Asp Leu Lys Gly Ser Gly
                100                 105                 110

Ser Gly Arg Ser Asp Asn His Gly Gly Gly Ser Glu Ile Val Val
                115                 120                 125

Thr Gln Ser Pro Ala Thr Leu Ser Val Ser Pro Gly Glu Arg Ala Thr
        130                 135                 140

Leu Ser Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Ala Asn Lys Arg Ala Pro Gly Val Pro Ala Arg Phe Ser Gly Ser
                180                 185                 190

Leu Ser Gly Asp Glu Ala Thr Leu Thr Ile Ser Ser Leu Gln Ser Glu
                195                 200                 205

Asp Phe Ala Val Tyr Tyr Cys Ala Leu Trp Tyr Ser Asn Leu Trp Val
                210                 215                 220

Phe Gly Gln Gly Thr Lys Leu Glu Ile Lys Arg Thr Val Ala Ala Pro
225                 230                 235                 240

Ser Val Phe Ile Phe Pro Pro Ser Asp Glu Gln Leu Lys Ser Gly Thr
```

```
                245                 250                 255
Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Ser Arg Asp Glu Leu Thr Lys Asn Gln Val Ser Leu
465                 470                 475                 480

Leu Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu His Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Lys

<210> SEQ ID NO 54
<211> LENGTH: 697
<212> TYPE: PRT
<213> ORGANISM: Artificial Sequence
<220> FEATURE:
<223> OTHER INFORMATION: Synthetic--Heavy chain of iBiTE-sp

<400> SEQUENCE: 54

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45
```

-continued

```
Ala Val Ile Ser Tyr Asp Gly Ser Asn Lys Tyr Tyr Ala Asp Ser Val
 50              55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Tyr Val Ala Arg Gly Asp Phe Asp Tyr Trp Gly Gln Gly
             100                 105                 110
Thr Leu Val Thr Val Ser Ser Gly Gly Gly Ser Gly Gly Gly Gly
             115                 120                 125
Ser Gly Gly Gly Gly Ser Asp Val Val Met Thr Gln Ser Pro Ser Thr
130                 135                 140
Leu Ser Ala Ser Val Gly Asp Arg Val Thr Ile Thr Cys Arg Ala Ser
145                 150                 155                 160
Gln Ser Met Ser Arg Trp Leu Ala Trp Tyr Gln Gln Lys Pro Gly Lys
                165                 170                 175
Gly Pro Lys Leu Leu Ile Tyr Ala Thr Ser Thr Leu Gln Ser Gly Val
             180                 185                 190
Pro Ser Arg Phe Ser Gly Ser Gly Ser Gly Thr Glu Phe Thr Leu Thr
             195                 200                 205
Ile Ser Ser Leu Gln Pro Glu Asp Phe Ala Thr Tyr Tyr Cys Gln Gln
210                 215                 220
Leu Asp Ser Phe Pro Phe Ser Phe Thr Phe Gly Pro Gly Thr Lys Val
225                 230                 235                 240
Asp Leu Lys Gly Gly Gly Ser Ser Glu Val Gln Leu Val Glu Ser Gly
                245                 250                 255
Gly Gly Leu Val Gln Pro Gly Gly Ser Leu Arg Leu Ser Cys Ala Ala
             260                 265                 270
Ser Gly Phe Thr Phe Asn Thr Tyr Ala Met Asn Trp Val Arg Gln Ala
             275                 280                 285
Pro Gly Lys Gly Leu Glu Trp Val Ala Arg Ile Arg Ser Lys Tyr Asn
290                 295                 300
Asn Tyr Ala Thr Tyr Tyr Ala Asp Ser Val Lys Gly Arg Phe Thr Ile
305                 310                 315                 320
Ser Arg Asp Asp Ser Lys Asn Thr Leu Tyr Leu Gln Met Asn Ser Leu
                325                 330                 335
Arg Ala Glu Asp Thr Ala Val Tyr Tyr Cys Val Arg His Gly Asn Phe
             340                 345                 350
Gly Asn Ser Tyr Val Ser Tyr Phe Ala Tyr Trp Gly Gln Gly Thr Thr
             355                 360                 365
Val Thr Val Ser Ser Ala Ser Thr Lys Gly Pro Ser Val Phe Pro Leu
             370                 375                 380
Ala Pro Ser Ser Lys Ser Thr Ser Gly Gly Thr Ala Ala Leu Gly Cys
385                 390                 395                 400
Leu Val Lys Asp Tyr Phe Pro Glu Pro Val Thr Val Ser Trp Asn Ser
                405                 410                 415
Gly Ala Leu Thr Ser Gly Val His Thr Phe Pro Ala Val Leu Gln Ser
             420                 425                 430
Ser Gly Leu Tyr Ser Leu Ser Ser Val Val Thr Val Pro Ser Ser Ser
             435                 440                 445
Leu Gly Thr Gln Thr Tyr Ile Cys Asn Val Asn His Lys Pro Ser Asn
450                 455                 460
```

```
Thr Lys Val Asp Lys Lys Val Glu Pro Lys Ser Cys Pro Pro Cys Pro
465                 470                 475                 480

Ala Pro Glu Leu Leu Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
        515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Ala Leu Pro Ala Pro Ile Glu Lys Thr Ile Ser Lys Ala Lys Gly Gln
                580                 585                 590

Pro Arg Glu Pro Gln Val Tyr Thr Leu Pro Pro Ser Arg Asp Glu Leu
            595                 600                 605

Thr Lys Asn Gln Val Ser Leu Leu Cys Leu Val Lys Gly Phe Tyr Pro
        610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

His Ser Lys Leu Thr Val Asp Lys Ser Arg Trp Gln Gln Gly Asn Val
                660                 665                 670

Phe Ser Cys Ser Val Met His Glu Ala Leu His Asn His Tyr Thr Gln
            675                 680                 685

Lys Ser Leu Ser Leu Ser Pro Gly Lys
            690                 695

<210> SEQ ID NO 55
<211> LENGTH: 438
<212> TYPE: PRT
<213> ORGANISM: Artificial Sequence
<220> FEATURE:
<223> OTHER INFORMATION: Synthetic--Light chain of iBiTE-sp

<400> SEQUENCE: 55

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Pro Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125
```

-continued

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Leu Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu His Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
        435

<210> SEQ ID NO 56
<211> LENGTH: 583
<212> TYPE: PRT
<213> ORGANISM: Artificial Sequence
<220> FEATURE:
<223> OTHER INFORMATION: Synthetic--Heavy chain of HBiTE-spg

<400> SEQUENCE: 56

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Tyr Val Ala Arg Gly Asp Phe Asp Tyr Trp Gly Gln Gly
                100                 105                 110
Thr Leu Val Thr Val Ser Ser Gly Gly Ser Gly Gly Gly Gly
                115                 120                 125
Ser Gly Gly Gly Gly Ser Glu Val Gln Leu Val Glu Ser Gly Gly Gly
                130                 135                 140
Leu Val Gln Pro Gly Gly Ser Leu Arg Leu Ser Cys Ala Ala Ser Gly
145                 150                 155                 160
Phe Thr Phe Asn Thr Tyr Ala Met Asn Trp Val Arg Gln Ala Pro Gly
                165                 170                 175
Lys Gly Leu Glu Trp Val Ala Arg Ile Arg Ser Lys Tyr Asn Asn Tyr
                180                 185                 190
Ala Thr Tyr Tyr Ala Asp Ser Val Lys Gly Arg Phe Thr Ile Ser Arg
                195                 200                 205
Asp Asp Ser Lys Asn Thr Leu Tyr Leu Gln Met Asn Ser Leu Arg Ala
210                 215                 220
Glu Asp Thr Ala Val Tyr Tyr Cys Ala Arg His Gly Asn Phe Gly Ser
225                 230                 235                 240
Ser Tyr Val Ser Tyr Phe Ala Tyr Trp Gly Gln Gly Thr Thr Val Thr
                245                 250                 255
Val Ser Ser Ala Ser Thr Lys Gly Pro Ser Val Phe Pro Leu Ala Pro
                260                 265                 270
Ser Ser Lys Ser Thr Ser Gly Gly Thr Ala Ala Leu Gly Cys Leu Val
                275                 280                 285
Lys Asp Tyr Phe Pro Glu Pro Val Thr Val Ser Trp Asn Ser Gly Ala
                290                 295                 300
Leu Thr Ser Gly Val His Thr Phe Pro Ala Val Leu Gln Ser Ser Gly
305                 310                 315                 320
Leu Tyr Ser Leu Ser Ser Val Val Thr Val Pro Ser Ser Ser Leu Gly
                325                 330                 335
Thr Gln Thr Tyr Ile Cys Asn Val Asn His Lys Pro Ser Asn Thr Lys
                340                 345                 350
Val Asp Lys Lys Val Glu Pro Lys Ser Cys Pro Pro Cys Pro Ala Pro
                355                 360                 365
Glu Leu Leu Gly Gly Pro Ser Val Phe Leu Phe Pro Pro Lys Pro Lys
370                 375                 380
Asp Thr Leu Met Ile Ser Arg Thr Pro Glu Val Thr Cys Val Val Val
385                 390                 395                 400
Asp Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
                420                 425                 430
Asn Ser Thr Tyr Arg Val Val Ser Val Leu Thr Val Leu His Gln Asp
                435                 440                 445
Trp Leu Asn Gly Lys Glu Tyr Lys Cys Lys Val Ser Asn Lys Ala Leu
450                 455                 460
Pro Ala Pro Ile Glu Lys Thr Ile Ser Lys Ala Lys Gly Gln Pro Arg
```

```
                       465                 470                 475                 480
Glu Pro Gln Val Tyr Thr Leu Pro Pro Ser Arg Asp Glu Leu Thr Lys
                    485                 490                 495
Asn Gln Val Ser Leu Leu Cys Leu Val Lys Gly Phe Tyr Pro Ser Asp
                500                 505                 510
Ile Ala Val Glu Trp Glu Ser Asn Gly Gln Pro Glu Asn Asn Tyr Lys
                515                 520                 525
Thr Thr Pro Pro Val Leu Asp Ser Asp Gly Ser Phe Phe Leu His Ser
            530                 535                 540
Lys Leu Thr Val Asp Lys Ser Arg Trp Gln Gln Gly Asn Val Phe Ser
545                 550                 555                 560
Cys Ser Val Met His Glu Ala Leu His Asn His Tyr Thr Gln Lys Ser
                565                 570                 575
Leu Ser Leu Ser Pro Gly Lys
            580

<210> SEQ ID NO 57
<211> LENGTH: 559
<212> TYPE: PRT
<213> ORGANISM: Artificial Sequence
<220> FEATURE:
<223> OTHER INFORMATION: Synthetic--Light chain of HBiTE-spg

<400> SEQUENCE: 57

Asp Val Val Met Thr Gln Ser Pro Ser Thr Leu Ser Ala Ser Val Gly
1               5                   10                  15
Asp Arg Val Thr Ile Thr Cys Arg Ala Ser Gln Ser Met Ser Arg Trp
            20                  25                  30
Leu Ala Trp Tyr Gln Gln Lys Pro Gly Lys Gly Pro Lys Leu Leu Ile
        35                  40                  45
Tyr Ala Thr Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Leu Asp Ser Phe Pro Phe
                85                  90                  95
Ser Phe Thr Phe Gly Pro Gly Thr Lys Val Asp Leu Lys Gly Ser Gly
            100                 105                 110
Gly Gly Gly Ser Gly Gly Gly Ser Glu Ile Val Val Thr Gln Ser
        115                 120                 125
Pro Ala Thr Leu Ser Val Ser Pro Gly Glu Arg Ala Thr Leu Ser Cys
    130                 135                 140
Arg Ser Ser Thr Gly Ala Val Thr Thr Ser Asn Tyr Ala Asn Trp Val
145                 150                 155                 160
Gln Gln Lys Pro Gly Gln Ala Pro Arg Gly Leu Ile Gly Gly Ala Asn
                165                 170                 175
Lys Arg Ala Pro Gly Val Pro Ala Arg Phe Ser Gly Ser Leu Ser Gly
            180                 185                 190
Asp Glu Ala Thr Leu Thr Ile Ser Ser Leu Gln Ser Glu Asp Phe Ala
        195                 200                 205
Val Tyr Tyr Cys Ala Leu Trp Tyr Ser Asn Leu Trp Val Phe Gly Gln
    210                 215                 220
Gly Thr Lys Leu Glu Ile Lys Arg Thr Val Ala Ala Pro Ser Val Phe
225                 230                 235                 240
Ile Phe Pro Pro Ser Asp Glu Gln Leu Lys Ser Gly Thr Ala Ser Val
```

```
                    245                 250                 255
Val Cys Leu Leu Asn Asn Phe Tyr Pro Arg Glu Ala Lys Val Gln Trp
            260                 265                 270
Lys Val Asp Asn Ala Leu Gln Ser Gly Asn Ser Gln Glu Ser Val Thr
            275                 280                 285
Glu Gln Asp Ser Lys Asp Ser Thr Tyr Ser Leu Ser Ser Thr Leu Thr
            290                 295                 300
Leu Ser Lys Ala Asp Tyr Glu Lys His Lys Val Tyr Ala Cys Glu Val
305                 310                 315                 320
Thr His Gln Gly Leu Ser Ser Pro Val Thr Lys Ser Phe Asn Arg Gly
                325                 330                 335
Glu Cys Pro Pro Cys Pro Ala Pro Glu Leu Leu Gly Gly Pro Ser Val
            340                 345                 350
Phe Leu Phe Pro Pro Lys Pro Lys Asp Thr Leu Met Ile Ser Arg Thr
            355                 360                 365
Pro Glu Val Thr Cys Val Val Val Asp Val Ser His Glu Asp Pro Glu
            370                 375                 380
Val Lys Phe Asn Trp Tyr Val Asp Gly Val Glu Val His Asn Ala Lys
385                 390                 395                 400
Thr Lys Pro Arg Glu Glu Gln Tyr Asn Ser Thr Tyr Arg Val Val Ser
                405                 410                 415
Val Leu Thr Val Leu His Gln Asp Trp Leu Asn Gly Lys Glu Tyr Lys
            420                 425                 430
Cys Lys Val Ser Asn Lys Ala Leu Pro Ala Pro Ile Glu Lys Thr Ile
            435                 440                 445
Ser Lys Ala Lys Gly Gln Pro Arg Glu Pro Gln Val Tyr Thr Leu Pro
450                 455                 460
Pro Ser Arg Asp Glu Leu Thr Lys Asn Gln Val Ser Leu Leu Cys Leu
465                 470                 475                 480
Val Lys Gly Phe Tyr Pro Ser Asp Ile Ala Val Glu Trp Glu Ser Asn
                485                 490                 495
Gly Gln Pro Glu Asn Asn Tyr Lys Thr Thr Pro Pro Val Leu Asp Ser
            500                 505                 510
Asp Gly Ser Phe Phe Leu His Ser Lys Leu Thr Val Asp Lys Ser Arg
            515                 520                 525
Trp Gln Gln Gly Asn Val Phe Ser Cys Ser Val Met His Glu Ala Leu
            530                 535                 540
His Asn His Tyr Thr Gln Lys Ser Leu Ser Leu Ser Pro Gly Lys
545                 550                 555

<210> SEQ ID NO 58
<211> LENGTH: 18
<212> TYPE: PRT
<213> ORGANISM: Artificial Sequence
<220> FEATURE:
<223> OTHER INFORMATION: Synthetic--linker GGGGSLSGRSDNHGGGGS

<400> SEQUENCE: 58

Gly Gly Gly Gly Ser Leu Ser Gly Arg Ser Asp Asn His Gly Gly Gly
1               5                   10                  15

Gly Ser

<210> SEQ ID NO 59
<211> LENGTH: 18
<212> TYPE: PRT
<213> ORGANISM: Artificial Sequence
```

```
<220> FEATURE:
<223> OTHER INFORMATION: Synthetic--linker GGGGSGPLGLARKGGGGS

<400> SEQUENCE: 59

Gly Gly Gly Gly Ser Gly Pro Leu Gly Leu Ala Arg Lys Gly Gly Gly
1               5                   10                  15

Gly Ser

<210> SEQ ID NO 60
<211> LENGTH: 21
<212> TYPE: PRT
<213> ORGANISM: Artificial Sequence
<220> FEATURE:
<223> OTHER INFORMATION: Synthetic--linker GGGGSLSGRSDNHGPLGLARK

<400> SEQUENCE: 60

Gly Gly Gly Gly Ser Leu Ser Gly Arg Ser Asp Asn His Gly Pro Leu
1               5                   10                  15

Gly Leu Ala Arg Lys
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic--linker GSLSGRSDNHGGGGS

<400> SEQUENCE: 61

Gly Ser Leu Ser Gly Arg Ser Asp Asn His Gly Gly Gly Gly Ser
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic--linker GSGSGRSDNHGGGGS

<400> SEQUENCE: 62

Gly Ser Gly Ser Gly Arg Ser Asp Asn His Gly Gly Gly Gly Ser
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic--linker, GSGGSRSDNHGGGGS

<400> SEQUENCE: 63

Gly Ser Gly Gly Ser Arg Ser Asp Asn His Gly Gly Gly Gly Ser
1               5                   10                  15

<210> SEQ ID NO 64
<211> LENGTH: 10
<212> TYPE: PRT
<213> ORGANISM: Artificial Sequence
<220> FEATURE:
<223> OTHER INFORMATION: Synthetic--hinge sequence DKTHTCPPCP

<400> SEQUENCE: 64

Asp Lys Thr His Thr Cys Pro Pro Cys Pro
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Synthetic--heterodimerization motif of human
      HER2 transmembrane domain LTSIISAVVG, (SEQ ID NO:65)

<400> SEQUENCE: 65

Leu Thr Ser Ile Ile Ser Ala Val Val Gly
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Synthetic--heterodimerization motif of human
      EGFR transmembrane domain SIATGMVG, (SEQ ID NO:66)

<400> SEQUENCE: 66

Ser Ile Ala Thr Gly Met Val Gly
1               5

<210> SEQ ID NO 67
<211> LENGTH: 16
<212> TYPE: PRT
<213> ORGANISM: Artificial Sequence
<220> FEATURE:
<223> OTHER INFORMATION: Synthetic--linker GGGGSGGGGSGRSDNH

<400> SEQUENCE: 67

Gly Gly Gly Gly Ser Gly Gly Gly Gly Ser Gly Arg Ser Asp Asn His
1               5                   10                  15

<210> SEQ ID NO 68
<211> LENGTH: 30
<212> TYPE: DNA
<213> ORGANISM: Artificial Sequence
<220> FEATURE:
<223> OTHER INFORMATION: Synthetic--OKTVLF (sense)

<400> SEQUENCE: 68
ggtgtccact ccgacatcca gatgacccag                                          30

<210> SEQ ID NO 69
<211> LENGTH: 32
<212> TYPE: DNA
<213> ORGANISM: Artificial Sequence
<220> FEATURE:
<223> OTHER INFORMATION: Synthetic--OKTVLR (antisense)

<400> SEQUENCE: 69
tgcagccaca gttcgggtta tctgcaactt tg                                       32

<210> SEQ ID NO 70
<211> LENGTH: 18
<212> TYPE: DNA
<213> ORGANISM: Artificial Sequence
<220> FEATURE:
<223> OTHER INFORMATION: Synthetic--CKF1 (sense)

<400> SEQUENCE: 70
cgaactgtgg ctgcacca                                                       18

<210> SEQ ID NO 71
<211> LENGTH: 31
```

```
<212> TYPE: DNA
<213> ORGANISM: Artificial Sequence
<220> FEATURE:
<223> OTHER INFORMATION: Synthetic--CKR1 (antisense)

<400> SEQUENCE: 71
tgctgggcac ggtggacact ctcccctgtt g                                    31

<210> SEQ ID NO 72
<211> LENGTH: 17
<212> TYPE: DNA
<213> ORGANISM: Artificial Sequence
<220> FEATURE:
<223> OTHER INFORMATION: Synthetic--MFCPAF (sense)

<400> SEQUENCE: 72
ccaccgtgcc cagcacc                                                    17

<210> SEQ ID NO 73
<211> LENGTH: 18
<212> TYPE: DNA
<213> ORGANISM: Artificial Sequence
<220> FEATURE:
<223> OTHER INFORMATION: Synthetic--AAAR (antisense)

<400> SEQUENCE: 73
cccgaggtcg acgctctc                                                   18

<210> SEQ ID NO 74
<211> LENGTH: 67
<212> TYPE: DNA
<213> ORGANISM: Artificial Sequence
<220> FEATURE:
<223> OTHER INFORMATION: Synthetic--OKT3VHF (sense)

<400> SEQUENCE: 74
gcaagcttat gtgagctcag gcggaggtgg ctctggcggt ggcggatcac aggtgcagct     60
ggtgcag                                                               67

<210> SEQ ID NO 75
<211> LENGTH: 30
<212> TYPE: DNA
<213> ORGANISM: Artificial Sequence
<220> FEATURE:
<223> OTHER INFORMATION: Synthetic--OKT3VHR (antisense)

<400> SEQUENCE: 75
gcccttggtg gaggctgagg agactgtgag                                      30

<210> SEQ ID NO 76
<211> LENGTH: 18
<212> TYPE: DNA
<213> ORGANISM: Artificial Sequence
<220> FEATURE:
<223> OTHER INFORMATION: Synthetic--CHCKF1MFCF (sense)

<400> SEQUENCE: 76
gcctccacca agggccca                                                   18

<210> SEQ ID NO 77
<211> LENGTH: 28
<212> TYPE: DNA
<213> ORGANISM: Artificial Sequence
<220> FEATURE:
<223> OTHER INFORMATION: Synthetic--CHMFCR (antisense)
```

```
<400> SEQUENCE: 77
gatcgaattc ttatttaccc ggagacag                                          28

<210> SEQ ID NO 78
<211> LENGTH: 46
<212> TYPE: DNA
<213> ORGANISM: Artificial Sequence
<220> FEATURE:
<223> OTHER INFORMATION: Synthetic--bnIgG20H1 (sense)

<400> SEQUENCE: 78
gtgttctaga gccgccacca tggaatggag ctgggtcttt ctcttc                      46

<210> SEQ ID NO 79
<211> LENGTH: 30
<212> TYPE: DNA
<213> ORGANISM: Artificial Sequence
<220> FEATURE:
<223> OTHER INFORMATION: Synthetic--12VHF (sense)

<400> SEQUENCE: 79
gatgccagat gtgaggtgca gctggtggag                                        30

<210> SEQ ID NO 80
<211> LENGTH: 36
<212> TYPE: DNA
<213> ORGANISM: Artificial Sequence
<220> FEATURE:
<223> OTHER INFORMATION: Synthetic--12VHR (antisense)

<400> SEQUENCE: 80
gatcgagctc cctccacctg aggagacggt gaccag                                 36

<210> SEQ ID NO 81
<211> LENGTH: 30
<212> TYPE: DNA
<213> ORGANISM: Artificial Sequence
<220> FEATURE:
<223> OTHER INFORMATION: Synthetic--12VLF (sense)

<400> SEQUENCE: 81
ggtgtccact ccgatgttgt gatgactcag                                        30

<210> SEQ ID NO 82
<211> LENGTH: 36
<212> TYPE: DNA
<213> ORGANISM: Artificial Sequence
<220> FEATURE:
<223> OTHER INFORMATION: Synthetic--12VLR (antisense)

<400> SEQUENCE: 82
gatcggatcc ccctccacct ttgagatcca ctttgg                                 36

<210> SEQ ID NO 83
<211> LENGTH: 46
<212> TYPE: DNA
<213> ORGANISM: Artificial Sequence
<220> FEATURE:
<223> OTHER INFORMATION: Synthetic--bnIgG20L1 (sense)

<400> SEQUENCE: 83
gtgtaagctt accatgggtg tgcccactca ggtcctgggg ttgctg                      46

<210> SEQ ID NO 84
<211> LENGTH: 67
```

```
<212> TYPE: DNA
<213> ORGANISM: Artificial Sequence
<220> FEATURE:
<223> OTHER INFORMATION: Synthetic--CHF (sense)

<400> SEQUENCE: 84
gatcggatcc ctgagtggaa ggagcgacaa ccacggcggt ggcggatcag acatccagat    60
gacccag                                                              67

<210> SEQ ID NO 85
<211> LENGTH: 67
<212> TYPE: DNA
<213> ORGANISM: Artificial Sequence
<220> FEATURE:
<223> OTHER INFORMATION: Synthetic--CHF1 (sense)

<400> SEQUENCE: 85
gatcggatcc ggacctctgg gcctcgctag gaagggcggt ggcggatcag acatccagat    60
gacccag                                                              67

<210> SEQ ID NO 86
<211> LENGTH: 76
<212> TYPE: DNA
<213> ORGANISM: Artificial Sequence
<220> FEATURE:
<223> OTHER INFORMATION: Synthetic--CHF2 (sense)

<400> SEQUENCE: 86
gatcggatcc ctgagtggaa ggagcgacaa ccacggacct ctgggcctcg ctaggaagga    60
catccagatg acccag                                                    76

<210> SEQ ID NO 87
<211> LENGTH: 27
<212> TYPE: DNA
<213> ORGANISM: Artificial Sequence
<220> FEATURE:
<223> OTHER INFORMATION: Synthetic--H12LR (antisense)

<400> SEQUENCE: 87
gatcggatcc tttgagatcc actttgg                                        27

<210> SEQ ID NO 88
<211> LENGTH: 34
<212> TYPE: DNA
<213> ORGANISM: Artificial Sequence
<220> FEATURE:
<223> OTHER INFORMATION: Synthetic--1S1F (sense)

<400> SEQUENCE: 88
gatcggatcc gggagtggaa ggagcgacaa ccac                                34

<210> SEQ ID NO 89
<211> LENGTH: 37
<212> TYPE: DNA
<213> ORGANISM: Artificial Sequence
<220> FEATURE:
<223> OTHER INFORMATION: Synthetic--1S2F (antisense)

<400> SEQUENCE: 89
gatcggatcc gggggaagta ggagcgacaa ccacggc                             37

<210> SEQ ID NO 90
<211> LENGTH: 78
<212> TYPE: DNA
```

```
<213> ORGANISM: Artificial Sequence
<220> FEATURE:
<223> OTHER INFORMATION: Synthetic--HEHR (antisense)

<400> SEQUENCE: 90
acttcccccg ccaccgctgc cacccccctcc gccaaccacc gcagagatga tggacgtcag    60
acatctggca tctgtaag                                                  78

<210> SEQ ID NO 91
<211> LENGTH: 51
<212> TYPE: DNA
<213> ORGANISM: Artificial Sequence
<220> FEATURE:
<223> OTHER INFORMATION: Synthetic--HEHF (sense)

<400> SEQUENCE: 91
agcggtggcg ggggaagtgg cggtggaggg agcgaggtgc agctggtgga g             51

<210> SEQ ID NO 92
<211> LENGTH: 36
<212> TYPE: DNA
<213> ORGANISM: Artificial Sequence
<220> FEATURE:
<223> OTHER INFORMATION: Synthetic--HEHR1 (antisense)

<400> SEQUENCE: 92
gatcgagctc cctccacctg aggagacggt gaccag                              36

<210> SEQ ID NO 93
<211> LENGTH: 71
<212> TYPE: DNA
<213> ORGANISM: Artificial Sequence
<220> FEATURE:
<223> OTHER INFORMATION: Synthetic--HELR (antisense)

<400> SEQUENCE: 93
acttcccccg ccaccgctgc cacccccctcc ccccaccatc ccagtggcga tggaggagtg    60
gacacctgta g                                                         71

<210> SEQ ID NO 94
<211> LENGTH: 54
<212> TYPE: DNA
<213> ORGANISM: Artificial Sequence
<220> FEATURE:
<223> OTHER INFORMATION: Synthetic--HELF (sense)

<400> SEQUENCE: 94
agcggtggcg ggggaagtgg aaggagcgac aaccacgatg ttgtgatgac tcag          54

<210> SEQ ID NO 95
<211> LENGTH: 27
<212> TYPE: DNA
<213> ORGANISM: Artificial Sequence
<220> FEATURE:
<223> OTHER INFORMATION: Synthetic--HELR1 (antisense)

<400> SEQUENCE: 95
gatcggatcc tttgagatcc actttgg                                        27

<210> SEQ ID NO 96
<211> LENGTH: 63
<212> TYPE: DNA
<213> ORGANISM: Artificial Sequence
<220> FEATURE:
<223> OTHER INFORMATION: Synthetic--GSHR (antisense)
```

<400> SEQUENCE: 96
gctccctcca ccgccacttc ccccgccacc gctgccaccc cctccacatc tggcatctgt    60
aag                                                                 63

<210> SEQ ID NO 97
<211> LENGTH: 66
<212> TYPE: DNA
<213> ORGANISM: Artificial Sequence
<220> FEATURE:
<223> OTHER INFORMATION: Synthetic--GSHF (sense)

<400> SEQUENCE: 97
agtggcggtg gagggagcgg gggcggaggt agtgggggag ggggatcgga ggtgcagctg    60
gtggag                                                              66

<210> SEQ ID NO 98
<211> LENGTH: 62
<212> TYPE: DNA
<213> ORGANISM: Artificial Sequence
<220> FEATURE:
<223> OTHER INFORMATION: Synthetic--GSLR (antisense)

<400> SEQUENCE: 98
gctccctcca ccgccacttc ccccgccacc gctgccaccc cctccggagt ggacacctgt    60
ag                                                                  62

<210> SEQ ID NO 99
<211> LENGTH: 69
<212> TYPE: DNA
<213> ORGANISM: Artificial Sequence
<220> FEATURE:
<223> OTHER INFORMATION: Synthetic--GSLF (sense)

<400> SEQUENCE: 99
agtggcggtg gagggagcgg gggcggaggt agtggaagga gcgacaacca cgatgttgtg    60
atgactcag                                                           69

<210> SEQ ID NO 100
<211> LENGTH: 30
<212> TYPE: DNA
<213> ORGANISM: Artificial Sequence
<220> FEATURE:
<223> OTHER INFORMATION: Synthetic--ER1HF (sense)

<400> SEQUENCE: 100
ggtgtccact ccgaggtgca gctggtggag                                    30

<210> SEQ ID NO 101
<211> LENGTH: 27
<212> TYPE: DNA
<213> ORGANISM: Artificial Sequence
<220> FEATURE:
<223> OTHER INFORMATION: Synthetic--ER1HR (antisense)

<400> SEQUENCE: 101
gatcgagctc acggtgacca gggttcc                                       27

<210> SEQ ID NO 102
<211> LENGTH: 30
<212> TYPE: DNA
<213> ORGANISM: Artificial Sequence
<220> FEATURE:

<223> OTHER INFORMATION: Synthetic--ER1LF (sense)

<400> SEQUENCE: 102
gatgccagat gtgacatcca gatgacccag                                    30

<210> SEQ ID NO 103
<211> LENGTH: 29
<212> TYPE: DNA
<213> ORGANISM: Artificial Sequence
<220> FEATURE:
<223> OTHER INFORMATION: Synthetic--ER1LR (antisense)

<400> SEQUENCE: 103
gatcgaattc ttaacactct ccccctgttg                                    29

<210> SEQ ID NO 104
<211> LENGTH: 30
<212> TYPE: DNA
<213> ORGANISM: Artificial Sequence
<220> FEATURE:
<223> OTHER INFORMATION: Synthetic--ER12LF1 (sense)

<400> SEQUENCE: 104
gatgccagat gtgatgttgt gatgactcag                                    30

<210> SEQ ID NO 105
<211> LENGTH: 18
<212> TYPE: DNA
<213> ORGANISM: Artificial Sequence
<220> FEATURE:
<223> OTHER INFORMATION: Synthetic--ER12LR1 (antisense)

<400> SEQUENCE: 105
tgtcccagat ccactgcc                                                 18

<210> SEQ ID NO 106
<211> LENGTH: 32
<212> TYPE: DNA
<213> ORGANISM: Artificial Sequence
<220> FEATURE:
<223> OTHER INFORMATION: Synthetic--ER12LF2 (sense)

<400> SEQUENCE: 106
ggatctggga cagagttcac tctcacaatc ag                                 32

<210> SEQ ID NO 107
<211> LENGTH: 30
<212> TYPE: DNA
<213> ORGANISM: Artificial Sequence
<220> FEATURE:
<223> OTHER INFORMATION: Synthetic--ER13LF (sense)

<400> SEQUENCE: 107
gatgccagat gtgacatcca gttgacccag                                    30

<210> SEQ ID NO 108
<211> LENGTH: 46
<212> TYPE: DNA
<213> ORGANISM: Artificial Sequence
<220> FEATURE:
<223> OTHER INFORMATION: Synthetic--bnIgG20H1 (sense)

<400> SEQUENCE: 108
gtgttctaga gccgccacca tggaatggag ctgggtcttt ctcttc                  46

```
<210> SEQ ID NO 109
<211> LENGTH: 46
<212> TYPE: DNA
<213> ORGANISM: Artificial Sequence
<220> FEATURE:
<223> OTHER INFORMATION: Synthetic--bnIgG20L1 (sense)

<400> SEQUENCE: 109
gtgtaagctt accatgggtg tgcccactca ggtcctgggg ttgctg            46

<210> SEQ ID NO 110
<211> LENGTH: 29
<212> TYPE: DNA
<213> ORGANISM: Artificial Sequence
<220> FEATURE:
<223> OTHER INFORMATION: Synthetic--SP34HF (sense)

<400> SEQUENCE: 110
gatcgagctc agaggtgcag ctggtggag                               29

<210> SEQ ID NO 111
<211> LENGTH: 30
<212> TYPE: DNA
<213> ORGANISM: Artificial Sequence
<220> FEATURE:
<223> OTHER INFORMATION: Synthetic--SP34HR (antisense)

<400> SEQUENCE: 111
gcccttggtg gaggctgagg agacggtgac                              30

<210> SEQ ID NO 112
<211> LENGTH: 18
<212> TYPE: DNA
<213> ORGANISM: Artificial Sequence
<220> FEATURE:
<223> OTHER INFORMATION: Synthetic--CFCF (sense)

<400> SEQUENCE: 112
gcctccacca agggccca                                           18

<210> SEQ ID NO 113
<211> LENGTH: 30
<212> TYPE: DNA
<213> ORGANISM: Artificial Sequence
<220> FEATURE:
<223> OTHER INFORMATION: Synthetic--MFc7.2R1 (antisense)

<400> SEQUENCE: 113
gatcgaattc ttatttaccc ggagacaggg                              30

<210> SEQ ID NO 114
<211> LENGTH: 30
<212> TYPE: DNA
<213> ORGANISM: Artificial Sequence
<220> FEATURE:
<223> OTHER INFORMATION: Synthetic--SP34LF (sense)

<400> SEQUENCE: 114
ggtgtccact ccgaaatagt ggtgacgcag                              30

<210> SEQ ID NO 115
<211> LENGTH: 32
<212> TYPE: DNA
<213> ORGANISM: Artificial Sequence
<220> FEATURE:
<223> OTHER INFORMATION: Synthetic--SP34LR (antisense)
```

```
<400> SEQUENCE: 115
tgcagccaca gttcgtttga tctccagctt gg                                    32

<210> SEQ ID NO 116
<211> LENGTH: 18
<212> TYPE: DNA
<213> ORGANISM: Artificial Sequence
<220> FEATURE:
<223> OTHER INFORMATION: Synthetic--CFCPAF (sense)

<400> SEQUENCE: 116
cgaactgtgg ctgcacca                                                    18

<210> SEQ ID NO 117
<211> LENGTH: 18
<212> TYPE: DNA
<213> ORGANISM: Artificial Sequence
<220> FEATURE:
<223> OTHER INFORMATION: Synthetic--AAAR (antisense)

<400> SEQUENCE: 117
cccgaggtcg acgctctc                                                    18

<210> SEQ ID NO 118
<211> LENGTH: 46
<212> TYPE: DNA
<213> ORGANISM: Artificial Sequence
<220> FEATURE:
<223> OTHER INFORMATION: Synthetic--bnIgG20H1 (sense)

<400> SEQUENCE: 118
gtgttctaga gccgccacca tggaatggag ctgggtcttt ctcttc                     46

<210> SEQ ID NO 119
<211> LENGTH: 67
<212> TYPE: DNA
<213> ORGANISM: Artificial Sequence
<220> FEATURE:
<223> OTHER INFORMATION: Synthetic--SFPAF (sense)

<400> SEQUENCE: 119
gatcggatcc gggagtggaa ggagcgacaa ccacggcggt ggcggatcag aaatagtggt      60
gacgcag                                                                67

<210> SEQ ID NO 120
<211> LENGTH: 59
<212> TYPE: DNA
<213> ORGANISM: Artificial Sequence
<220> FEATURE:
<223> OTHER INFORMATION: Synthetic--SFF (sense)

<400> SEQUENCE: 120
gatcgagctc aggcggaggt ggctctggcg gtggcggatc agaggtgcag ctggtggag       59

<210> SEQ ID NO 121
<211> LENGTH: 36
<212> TYPE: DNA
<213> ORGANISM: Artificial Sequence
<220> FEATURE:
<223> OTHER INFORMATION: Synthetic--VNFR (antisense)

<400> SEQUENCE: 121
cccgaagttt ccgtgtctcg cacagtaata tacggc                                36
```

```
<210> SEQ ID NO 122
<211> LENGTH: 46
<212> TYPE: DNA
<213> ORGANISM: Artificial Sequence
<220> FEATURE:
<223> OTHER INFORMATION: Synthetic--bnIgG20L1 (sense)

<400> SEQUENCE: 122
gtgtaagctt accatgggtg tgcccactca ggtcctgggg ttgctg                46

<210> SEQ ID NO 123
<211> LENGTH: 36
<212> TYPE: DNA
<213> ORGANISM: Artificial Sequence
<220> FEATURE:
<223> OTHER INFORMATION: Synthetic--VNFF (sense)

<400> SEQUENCE: 123
cacggaaact tcgggagttc ctacgtgtct tacttc                           36

<210> SEQ ID NO 124
<211> LENGTH: 64
<212> TYPE: DNA
<213> ORGANISM: Artificial Sequence
<220> FEATURE:
<223> OTHER INFORMATION: Synthetic--HSPGF (antisense)

<400> SEQUENCE: 124
gatcggatcc gggggatccg gcggaggtgg ctctggcggt ggcggatcag aaatagtggt 60
gacg                                                              64

<210> SEQ ID NO 125
<211> LENGTH: 15
<212> TYPE: DNA
<213> ORGANISM: Artificial Sequence
<220> FEATURE:
<223> OTHER INFORMATION: Synthetic--linker

<400> SEQUENCE: 125
ggggsggggs gggs                                                   15

<210> SEQ ID NO 126
<211> LENGTH: 15
<212> TYPE: DNA
<213> ORGANISM: Artificial Sequence
<220> FEATURE:
<223> OTHER INFORMATION: Synthetic--linker

<400> SEQUENCE: 126
gggssggggs gggs                                                   15

<210> SEQ ID NO 127
<211> LENGTH: 12
<212> TYPE: DNA
<213> ORGANISM: Artificial Sequence
<220> FEATURE:
<223> OTHER INFORMATION: Synthetic--linker

<400> SEQUENCE: 127
gsggggsggg gs                                                     12

<210> SEQ ID NO 128
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 128

Pro Leu Gly Leu Trp Ala
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic

<400> SEQUENCE: 129

Gly Pro Leu Gly Leu Trp Ala
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Gly Pro Leu Gly Leu Trp Ala Gln
1               5

<210> SEQ ID NO 131
<211> LENGTH: 12
<212> TYPE: PRT
<213> ORGANISM: Artificial Sequence
<220> FEATURE:
<223> OTHER INFORMATION: Synthetic

<400> SEQUENCE: 131

Gly Val Pro Asp Leu Gly Arg Phe Gln Thr Phe Glu
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Gly Val Pro Asp Val Gly His Phe Ser Leu Phe Pro
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic

<400> SEQUENCE: 133

Gly Val Pro Asp Val Gly Glu Phe Ser Leu Phe Pro
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic
```

<400> SEQUENCE: 134

Gly Val Pro Asp Val Gly Asn Phe Ser Leu Phe Pro
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic

<400> SEQUENCE: 135

Gly Val Pro Asp Val Gly Arg Phe Ser Leu Phe Pro
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

Gly Val Pro Asp Val Gly His Tyr Ser Leu Phe Pro
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic

<400> SEQUENCE: 137

Gly Val Pro Asp Val Gly Glu Tyr Ser Leu Phe Pro
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

Gly Val Pro Asp Val Gly Asn Tyr Ser Leu Phe Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic

<400> SEQUENCE: 139

Gly Val Pro Asp Val Gly Arg Tyr Ser Leu Phe Pro
1               5                   10

<210> SEQ ID NO 140
<211> LENGTH: 8
<212> TYPE: PRT
<213> ORGANISM: Artificial Sequence
<220> FEATURE:
<223> OTHER INFORMATION: Synthetic--protease cleavage sites for
      urokinase (uPA)

<400> SEQUENCE: 140

Pro Arg Phe Lys Ile Ile Gly Gly
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic--protease cleavage sites for
      urokinase (uPA)

<400> SEQUENCE: 141

Pro Arg Phe Arg Ile Ile Gly Gly
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic--protease cleavage site for TGF-beta

<400> SEQUENCE: 142

Ser Ser Arg His Arg Arg Ala Leu Asp
1               5

<210> SEQ ID NO 143
<211> LENGTH: 14
<212> TYPE: PRT
<213> ORGANISM: Artificial Sequence
<220> FEATURE:
<223> OTHER INFORMATION: Synthetic--protease cleavage site for
      plasminogen

<400> SEQUENCE: 143

Arg Lys Ser Ser Ile Ile Ile Arg Met Arg Asp Val Val Leu
1               5                   10

<210> SEQ ID NO 144
<211> LENGTH: 15
<212> TYPE: PRT
<213> ORGANISM: Artificial Sequence
<220> FEATURE:
<223> OTHER INFORMATION: Synthetic--protease cleavage site for
      staphylokinase:

<400> SEQUENCE: 144

Ser Ser Ser Phe Asp Lys Gly Lys Tyr Lys Lys Gly Asp Asp Ala
1               5                   10                  15

<210> SEQ ID NO 145
<211> LENGTH: 4
<212> TYPE: PRT
<213> ORGANISM: Artificial Sequence
<220> FEATURE:
<223> OTHER INFORMATION: Synthetic--protease cleavage sites for factor
      Xa:

<400> SEQUENCE: 145

Ile Glu Gly Arg
1

<210> SEQ ID NO 146
<211> LENGTH: 4
<212> TYPE: PRT

```
<213> ORGANISM: Artificial Sequence
<220> FEATURE:
<223> OTHER INFORMATION: Synthetic--protease cleavage sites for factor
      Xa

<400> SEQUENCE: 146

Ile Asp Gly Arg
1

<210> SEQ ID NO 147
<211> LENGTH: 7
<212> TYPE: PRT
<213> ORGANISM: Artificial Sequence
<220> FEATURE:
<223> OTHER INFORMATION: Synthetic--protease cleavage sites for factor
      Xa

<400> SEQUENCE: 147

Gly Gly Ser Ile Asp Gly Arg
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic--protease cleavage site for human
      liver collagen:

<400> SEQUENCE: 148

Gly Pro Leu Gly Ile Ala Gly Ile
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic--protease cleavage site for human
      alpha-2M

<400> SEQUENCE: 149

Gly Pro Glu Gly Leu Arg Val Gly
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic--protease cleavage sites for human
      PZP:

<400> SEQUENCE: 150

Tyr Gly Ala Gly Leu Gly Val Val
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic--protease cleavage sites for human
      PZP

<400> SEQUENCE: 151

Ala Gly Leu Gly Val Val Glu Arg
1               5
```

<210> SEQ ID NO 152
<211> LENGTH: 8
<212> TYPE: PRT
<213> ORGANISM: Artificial Sequence
<220> FEATURE:
<223> OTHER INFORMATION: Synthetic--protease cleavage sites for human PZP

<400> SEQUENCE: 152

Ala Gly Leu Gly Ile Ser Ser Thr
1               5

<210> SEQ ID NO 153
<211> LENGTH: 10
<212> TYPE: PRT
<213> ORGANISM: Artificial Sequence
<220> FEATURE:
<223> OTHER INFORMATION: Synthetic--flexible motif

<400> SEQUENCE: 153

Gly Gly Gly Gly Ser Gly Gly Gly Gly Ser
1               5                   10

<210> SEQ ID NO 154
<211> LENGTH: 5
<212> TYPE: PRT
<213> ORGANISM: Artificial Sequence
<220> FEATURE:
<223> OTHER INFORMATION: Synthetic--part of the human IgG1 hinge sequence

<400> SEQUENCE: 154

Cys Pro Pro Cys Pro
1               5

<210> SEQ ID NO 155
<211> LENGTH: 107
<212> TYPE: PRT
<213> ORGANISM: Artificial Sequence
<220> FEATURE:
<223> OTHER INFORMATION: Synthetic

<400> SEQUENCE: 155

Gly Gln Pro Arg Glu Pro Gln Val Tyr Thr Leu Pro Pro Ser Arg Asp
1               5                   10                  15

Glu Leu Thr Lys Asn Gln Val Ser Leu Asp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Ile Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 156
<211> LENGTH: 107
<212> TYPE: PRT
<213> ORGANISM: Artificial Sequence
<220> FEATURE:

<223> OTHER INFORMATION: Synthetic

<400> SEQUENCE: 156

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Phe Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 157
<211> LENGTH: 107
<212> TYPE: PRT
<213> ORGANISM: Artificial Sequence
<220> FEATURE:
<223> OTHER INFORMATION: Synthetic

<400> SEQUENCE: 157

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Leu Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 158
<211> LENGTH: 107
<212> TYPE: PRT
<213> ORGANISM: Artificial Sequence
<220> FEATURE:
<223> OTHER INFORMATION: Synthetic

<400> SEQUENCE: 158

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Met Ser Lys Leu Thr Val Asp Lys Ser Arg Trp Gln Gln Gly

```
                65                  70                  75                  80
Asn Val Phe Ser Cys Ser Val Met His Glu Ala Leu His Asn His Tyr
                    85                  90                  95

Thr Gln Lys Ser Leu Ser Leu Ser Pro Gly Lys
            100                 105

<210> SEQ ID NO 159
<211> LENGTH: 107
<212> TYPE: PRT
<213> ORGANISM: Artificial Sequence
<220> FEATURE:
<223> OTHER INFORMATION: Synthetic

<400> SEQUENCE: 159

Gly Gln Pro Arg Glu Pro Gln Val Tyr Thr Leu Pro Pro Ser Arg Asp
1               5                   10                  15

Glu Leu Thr Lys Asn Gln Val Ser Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 160
<211> LENGTH: 107
<212> TYPE: PRT
<213> ORGANISM: Artificial Sequence
<220> FEATURE:
<223> OTHER INFORMATION: Synthetic

<400> SEQUENCE: 160

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Phe Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 161
<211> LENGTH: 107
<212> TYPE: PRT
<213> ORGANISM: Artificial Sequence
<220> FEATURE:
<223> OTHER INFORMATION: Synthetic

<400> SEQUENCE: 161
```

Gly Gln Pro Arg Glu Pro Gln Val Tyr Thr Leu Pro Pro Ser Arg Asp
1               5                   10                  15

Glu Leu Thr Lys Asn Gln Val Ser Leu Asn Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Leu Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 162
<211> LENGTH: 107
<212> TYPE: PRT
<213> ORGANISM: Artificial Sequence
<220> FEATURE:
<223> OTHER INFORMATION: Synthetic

<400> SEQUENCE: 162

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu His Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 163
<211> LENGTH: 107
<212> TYPE: PRT
<213> ORGANISM: Artificial Sequence
<220> FEATURE:
<223> OTHER INFORMATION: Synthetic

<400> SEQUENCE: 163

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Lys Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr

<210> SEQ ID NO 164
<211> LENGTH: 107
<212> TYPE: PRT
<213> ORGANISM: Artificial Sequence
<220> FEATURE:
<223> OTHER INFORMATION: Synthetic

<400> SEQUENCE: 164

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Ser Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 165
<211> LENGTH: 107
<212> TYPE: PRT
<213> ORGANISM: Artificial Sequence
<220> FEATURE:
<223> OTHER INFORMATION: Synthetic

<400> SEQUENCE: 165

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Gln Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 166
<211> LENGTH: 107
<212> TYPE: PRT
<213> ORGANISM: Artificial Sequence
<220> FEATURE:
<223> OTHER INFORMATION: Synthetic

<400> SEQUENCE: 166

Gly Gln Pro Arg Glu Pro Gln Val Tyr Thr Leu Pro Pro Ser Arg Asp
1               5                   10                  15

```
Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Thr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 167
<211> LENGTH: 107
<212> TYPE: PRT
<213> ORGANISM: Artificial Sequence
<220> FEATURE:
<223> OTHER INFORMATION: Synthetic

<400> SEQUENCE: 167

```
Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Trp Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

```
Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Ala Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
```

<210> SEQ ID NO 169
<211> LENGTH: 107
<212> TYPE: PRT
<213> ORGANISM: Artificial Sequence
<220> FEATURE:
<223> OTHER INFORMATION: Synthetic

<400> SEQUENCE: 169

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Gly Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Gly Gln Pro Arg Glu Pro Gln Val Tyr Thr Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Asn Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50              55                          60

Phe Leu Tyr Ser Lys Leu Thr Val Asp Lys Ser Arg Trp Gln Gln Gly
 65              70                  75                      80

Asn Val Phe Ser Cys Ser Val Met His Glu Ala Leu His Asn His Tyr
                85                  90                      95

Thr Gln Lys Ser Leu Ser Leu Ser Pro Gly Lys
            100                 105

<210> SEQ ID NO 172
<211> LENGTH: 217
<212> TYPE: PRT
<213> ORGANISM: Homo sapiens

<400> SEQUENCE: 172

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65              70                  75                      80

Gln Asp Trp Leu Asn Gly Lys Glu Tyr Lys Cys Lys Val Ser Asn Lys
                85                  90                      95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Leu Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

His Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```